US012673085B2

(12) United States Patent (10) Patent No.: US 12,673,085 B2
Rogers et al. (45) Date of Patent: Jul. 7, 2026

(54) CBM USES

(71) Applicant: OMIDEON LTD, Fife (GB)

(72) Inventors: Graeme Rogers, St. Andrews (GB);
Helen Connaris, St. Andrews (GB)

(73) Assignee: OMIDEON LIMITED, St. Andrews
(GB)

( * ) Notice: Subject to any disclaimer, the term of this
patent is extended or adjusted under 35
U.S.C. 154(b) by 1261 days.

(21) Appl. No.: 17/425,374

(22) PCT Filed: Jan. 24, 2020

(86) PCT No.: PCT/GB2020/050170
§ 371 (c)(1),
(2) Date: Jul. 23, 2021

(87) PCT Pub. No.: WO2020/152479
PCT Pub. Date: Jul. 30, 2020

(65) Prior Publication Data

US 2022/0088120 A1 Mar. 24, 2022

(30) Foreign Application Priority Data

Jan. 25, 2019 (GB) .................................... 1901057

(51) Int. Cl.
*A61K 38/16* (2006.01)
*A61P 35/00* (2006.01)

(52) U.S. Cl.
CPC ............ *A61K 38/164* (2013.01); *A61P 35/00*
(2018.01)

(58) Field of Classification Search
CPC ........ A61K 38/164; A61K 38/43; A61P 35/00
See application file for complete search history.

(56) References Cited

FOREIGN PATENT DOCUMENTS

| | | |
|---|---|---|
| JP | 5917913 B2 | 5/2016 |
| WO | 2018055373 A1 | 3/2018 |
| WO | 2019138222 A1 | 7/2019 |

OTHER PUBLICATIONS

H. Connaris et al, "Prevention of influenza by targeting host receptors using engineered proteins", Proceedings of the National Academy of Sciences, vol. {0} 111, No. {0} 17, Apr. 29, 2014 (Apr. 29, 2014) (Year: 2014).*
Evans et al. Q. J. Med 1999: 92: 299-307 (Year: 1999).*
Komenaka et al., Clinics in Dermatology, 2004, vol. 22, p. 251-265 (Year: 2004).*
Schiffman et al., The New England Journal of Medicine, vol. 353, No. 20, p. 2101-2104, 2005 (Year: 2005).*
Tseng et al. Enzyme and Microbial Technology 41 (2007) 5-12 (Year: 2007).*
Hernandez-Ledesma et al. Peptides, vol. 30, p. 426-430, 2009 (Year: 2009).*
Park et al. Gut Liver 2013;7(6):629-641 (Year: 2013).*
Li et al. Toxins 2016, 8(11), 341-355 (Year: 2016).*
Riberio et al. Biochem J (2016) 473 (14): 2109-2118. (Year: 2016).*
Sokolenko et al. Frontiers in molecular biosciences. Aug. 27, 2018;5:76. (Year: 2018).*
Cuzick et al. The Lancet, vol. 361, p. 296-300, 2003. (Year: 2003).*
UniProt entry A0A2X2YJF2: nanJ sequence; URL: https://www.uniprot.org/uniprotkb/A0A2X2YJF2/entry (Year: 2018) (Year: 2018).*
International Search Report and Written Opinion corresponding to PCT/GB2020/050170 (16 pages).
Ficko-Blean, Elizabeth , et al., "N-Acetylglucosamine Recognition by a Family 32 Carbohydrate-Binding Module from Clostridium perfringens NagH", Journal of Molecular Biology 390(2), 2009, 208-220.
Guillen, Daniel , et al., "Carbohydrate-binding domains: multiplicity of biological roles", Applied Microbiology and Biotechnology 85, 2010, 1241-1249.
Shimizu, Tohru , et al., "Complete genome sequence of Clostridium perfringens, an anaerobic flesh-eater", PNAS 99(2), 2002, 996-1001.
Accession No. WP_003450115 "exo-alpha-sialidase [Clostridium perfringens]" NCBI (2 pages) (May 25, 2013).
Accession No. A0A2X2YJF2 "Exo-alpha-sialidase [Clostridium perfringens]" UniProtKB; accessed Dec. 2023 (4 pages).

* cited by examiner

Primary Examiner — Sean E Aeder
Assistant Examiner — Yie Chia Lee
(74) Attorney, Agent, or Firm — Myers Bigel, P.A.

(57) ABSTRACT

The present disclosure provides molecules which modulate cell growth. These molecules include those that bind carbohydrates and may find application in the treatment and/or prevention of cell proliferation and/or differentiation disorders, cancer and/or it's migration and/or spread.

9 Claims, 16 Drawing Sheets

Figure 1:
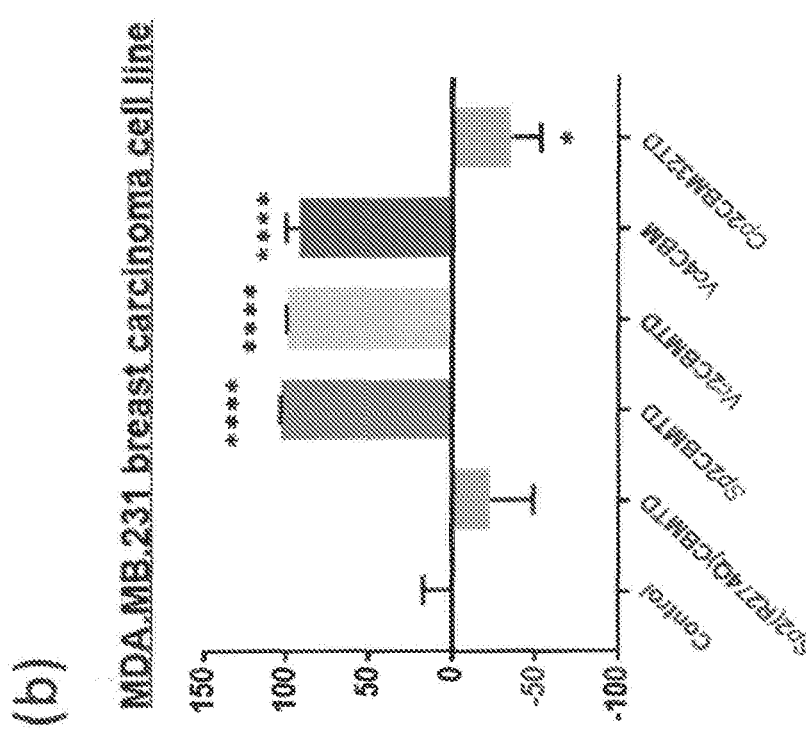
Figure 1:
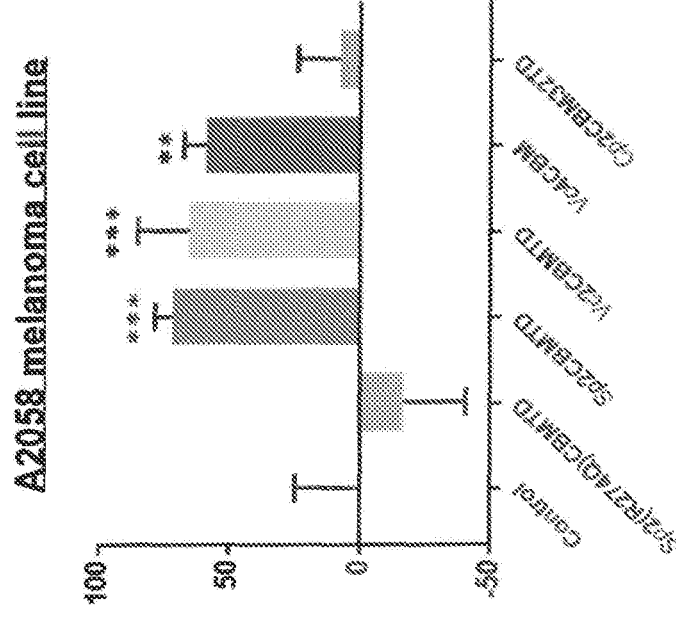
Figure 1:
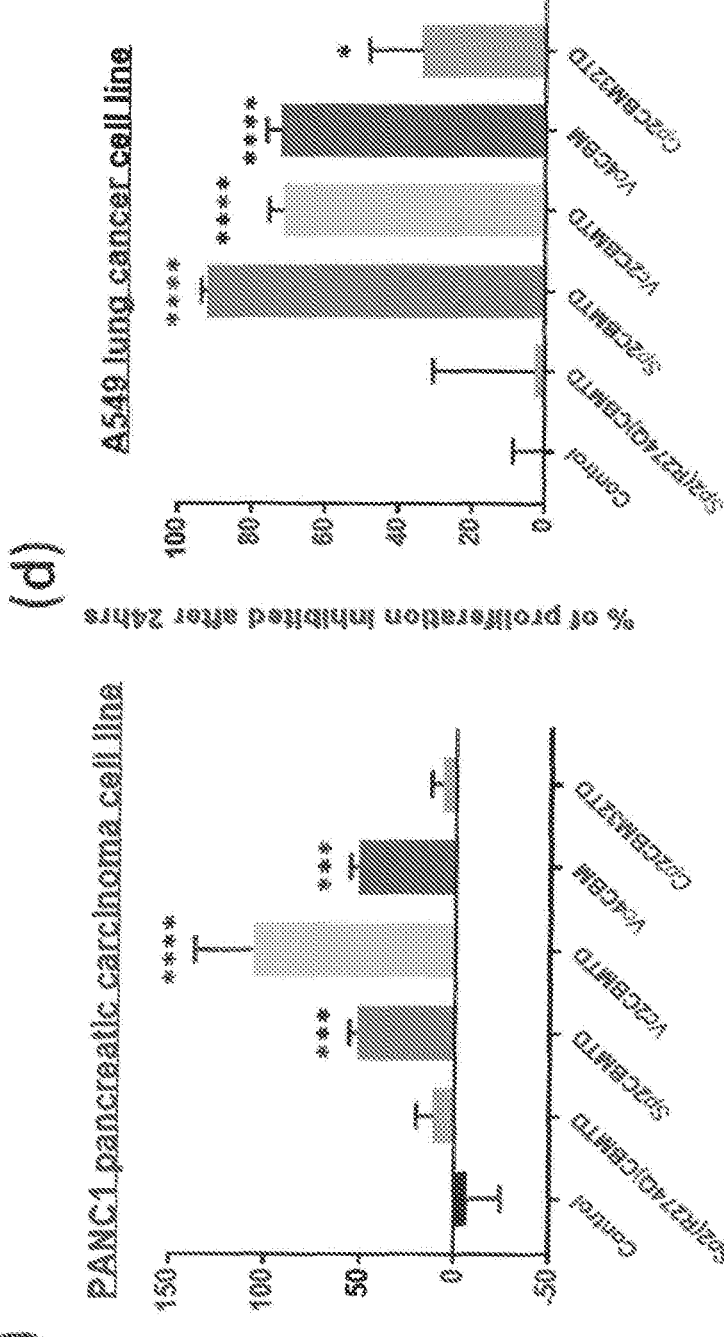

Specification includes a Sequence Listing.

SEQUENCE LISTING

```
<160> NUMBER OF SEQ ID NOS: 27

<210> SEQ ID NO 1
<211> LENGTH: 139
<212> TYPE: PRT
<213> ORGANISM: Clostridium perfringens

<400> SEQUENCE: 1

Ala Ile Ile Glu Thr Ala Ile Pro Gln Ser Glu Met Thr Ala Ser Ala
1               5                   10                  15

Thr Ser Glu Glu Gly Gln Asp Pro Ala Ser Ser Ala Ile Asp Gly Asn
            20                  25                  30

Thr Asn Thr Met Trp His Thr Lys Trp Asn Gly Ser Asp Ala Leu Pro
        35                  40                  45

Gln Ser Leu Ser Val Asn Leu Gly Ser Ser Arg Lys Val Ser Ser Ile
    50                  55                  60

Ala Ile Thr Pro Arg Thr Ser Gly Asn Asn Gly Phe Ile Thr Lys Tyr
65                  70                  75                  80

Glu Ile His Ala Ile Asn Asn Gly Val Glu Thr Leu Val Ala Glu Gly
            85                  90                  95

Thr Trp Glu Glu Asn Asn Leu Val Lys Thr Val Thr Phe Asp Ser Pro
            100                 105                 110

Ile Asp Ala Glu Glu Ile Lys Ile Thr Ala Ile Gln Gly Val Gly Gly
        115                 120                 125

Phe Ala Ser Ile Ala Glu Leu Asn Val Tyr Glu
    130                 135

<210> SEQ ID NO 2
<211> LENGTH: 1173
<212> TYPE: PRT
<213> ORGANISM: Clostridium perfringens

<400> SEQUENCE: 2

Met Lys Ser Lys Lys Ile Ile Ala Thr Leu Val Ala Ser Leu Val Ile
1               5                   10                  15

Ser Asn Met Gly Gly Tyr Leu Val Lys Ala Asn Pro Asn Val Asn His
            20                  25                  30
```

-continued

```
Lys Ala Val Ile Ile Glu Asp Arg Gln Ala Ile Ile Glu Thr Ala Ile
        35                  40                  45

Pro Gln Ser Glu Met Thr Ala Ser Ala Thr Ser Glu Glu Gly Gln Asp
    50                  55                  60

Pro Ala Ser Ser Ala Ile Asp Gly Asn Thr Asn Thr Met Trp His Thr
65                  70                  75                  80

Lys Trp Asn Gly Ser Asp Ala Leu Pro Gln Ser Leu Ser Val Asn Leu
                85                  90                  95

Gly Ser Ser Arg Lys Val Ser Ser Ile Ala Ile Thr Pro Arg Thr Ser
            100                 105                 110

Gly Asn Asn Gly Phe Ile Thr Lys Tyr Glu Ile His Ala Ile Asn Asn
            115                 120                 125

Gly Val Glu Thr Leu Val Ala Glu Gly Thr Trp Glu Glu Asn Asn Leu
        130                 135                 140

Val Lys Thr Val Thr Phe Asp Ser Pro Ile Asp Ala Glu Glu Ile Lys
145                 150                 155                 160

Ile Thr Ala Ile Gln Gly Val Gly Gly Phe Ala Ser Ile Ala Glu Leu
                165                 170                 175

Asn Val Tyr Glu Ile Lys Gly Glu Val Asp Glu Ile Ala Asn Tyr Gly
            180                 185                 190

Asn Leu Lys Ile Thr Lys Glu Glu Glu Arg Leu Asn Ile Thr Arg Asp
            195                 200                 205

Leu Glu Lys Phe Ser Ser Leu Asp Glu Gly Thr Ile Val Thr Arg Phe
        210                 215                 220

Asn Met Asn Asp Thr Ser Ile Gln Ser Leu Ile Gly Leu Ser Asp Gly
225                 230                 235                 240

Asn Lys Ala Asn Asn Tyr Phe Ser Leu Tyr Val Ser Gly Gly Lys Val
                245                 250                 255

Gly Tyr Glu Leu Arg Arg Gln Glu Gly Asn Gly Asp Phe Asn Val His
            260                 265                 270

His Ser Ala Asp Val Thr Phe Asn Lys Gly Ile Asn Thr Leu Ala Leu
            275                 280                 285

Lys Ile Glu Lys Gly Val Gly Ala Lys Ile Phe Leu Asn Gly Ser Leu
        290                 295                 300

Val Lys Thr Val Ser Asp Pro Asn Ile Lys Phe Leu Asn Ala Ile Asn
305                 310                 315                 320

Leu Asn Ser Gly Phe Ile Gly Lys Thr Asp Arg Ala Asn Gly Tyr Asn
                325                 330                 335

Glu Tyr Leu Phe Arg Gly Asn Ile Asp Phe Met Asn Ile Tyr Asp Lys
            340                 345                 350

Pro Val Ser Asp Asn Tyr Leu Leu Arg Lys Thr Gly Glu Thr Lys Ala
            355                 360                 365

Pro Ser Glu Asp Ser Leu Leu Pro Asp Asp Val Tyr Lys Thr Gln Pro
        370                 375                 380

Val Glu Leu Phe Tyr Pro Gly Tyr Leu Glu Ser Arg Gly Tyr Arg Ile
385                 390                 395                 400

Pro Ala Leu Glu Thr Thr Lys Lys Gly Thr Val Leu Ala Ser Ile Asp
                405                 410                 415

Val Arg Asn Asn Gly Asp His Asp Ala Pro Asn Asn Ile Asp Val
                420                 425                 430

Gly Ile Arg Arg Lys Glu Val Asn Gly Glu Trp Glu Glu Gly Lys Val
        435                 440                 445

Ile Leu Asp Tyr Pro Gly Lys Ser Ala Ala Ile Asp Thr Ser Leu Met
```

-continued

```
              450             455             460

Ser Ala Thr Ile Glu Glu Asn Gly Ile Glu Lys Glu Arg Ile Phe Leu
465             470             475             480

Ile Val Thr His Phe Pro Glu Gly Tyr Gly Phe Pro Asn Thr Glu Gly
                485             490             495

Gly Ser Gly Tyr Lys Glu Ile Asp Gly Lys Tyr Tyr Phe Ile Leu Lys
                500             505             510

Asp Ala Gln Asn Asn Glu Tyr Thr Val Arg Glu Asp Gly Ile Val Tyr
                515             520             525

Asn Ser Glu Gly Asn Glu Thr Asp Tyr Val Met Lys Asn Asp Lys Thr
                530             535             540

Leu Ile Gln Asn Gly Glu Glu Val Gly Asn Ala Leu Leu Ser Asn Ser
545             550             555             560

Pro Leu Lys Ala Val Gly Thr Ala His Ile Glu Met Ile Tyr Ser Asp
                565             570             575

Asp Asp Gly Asn Thr Trp Ser Glu Pro Glu Asp Leu Asn Pro Gly Leu
                580             585             590

Lys Lys Glu Trp Met Lys Phe Phe Gly Thr Ala Pro Gly Lys Gly Ile
                595             600             605

Gln Ile Lys Asn Gly Glu His Lys Gly Arg Leu Val Phe Pro Ile Tyr
    610             615             620

Tyr Thr Asn Gln Asn Asn Phe Gln Ser Ser Ala Val Ile Tyr Ser Asp
625             630             635             640

Asp Phe Gly Glu Thr Trp Lys Leu Gly Glu Ser Pro Ile Asp Thr Ala
                645             650             655

Ser Val Ser Ser Glu Thr Val Ser Ser Gly Thr Gln Leu Thr Glu Cys
                660             665             670

Gln Val Val Glu Met Pro Asn Gly Gln Leu Lys Leu Phe Met Arg Asn
                675             680             685

Thr Gly Ser Tyr Thr Arg Ile Ala Thr Ser Phe Asp Gly Gly Ala Thr
    690             695             700

Trp His Asp Glu Val Pro Glu Asp Thr Ser Leu Arg Glu Pro Tyr Cys
705             710             715             720

Gln Leu Ser Val Ile Asn Tyr Ser Gly Lys Ile Asn Gly Lys Asp Ala
                725             730             735

Ile Ile Phe Ser Asn Pro Asp Ala Ser Ser Arg Val Asn Gly Ser Val
                740             745             750

Lys Val Gly Leu Ile Asn Glu Asn Gly Thr Tyr Glu Asn Gly Gln Pro
                755             760             765

Arg Tyr Glu Phe Asp Trp Ile Tyr Asn Lys Thr Val Lys Pro Gly Ser
    770             775             780

Phe Ala Tyr Ser Cys Leu Thr Glu Leu Pro Asp Gly Asn Leu Gly Leu
785             790             795             800

Phe Tyr Glu Gly Glu Gly Ala Gly Arg Met Ala Tyr Thr Glu Phe Asp
                805             810             815

Leu Asn Tyr Leu Lys Phe Asn Ala Ser Glu Asp Ser Pro Ala Ala Thr
                820             825             830

Val Gln Ser Ile Glu Ser Leu Asp Glu Asp Leu Ile Tyr Asn Ala Gly
                835             840             845

Asp Glu Val Ser Ile Lys Val Asn Phe Asn Gln Leu Val Ser Leu Ile
    850             855             860

Gly Asp Arg Lys Ile Thr Leu Asp Ile Gly Gly Val Asp Val Pro Leu
865             870             875             880
```

-continued

```
Asn Met Val Asn Tyr Glu Gly Lys Ser Ser Ala Ile Phe Lys Gly Thr
            885                 890                 895

Ile Pro Glu Gly Ile Asn Pro Gly Asn Tyr Glu Ile Lys Leu Lys Glu
            900                 905                 910

Asn Asn Ala Leu Glu Leu Asn Thr Val Tyr Asn Lys Val Ser Thr Leu
        915                 920                 925

Asn Gly Leu Asp Asn Thr Gly Ile Asn Val Gln Ile Gly Glu Leu Lys
    930                 935                 940

Thr Thr Val Gly Asn Ser Thr Ile Lys Val Asn Glu Glu Val Gln Val
945                 950                 955                 960

Gly Ser Ala Phe Glu Ala Ile Leu Gly Ile Lys Gly Leu Asn Gly Asp
                965                 970                 975

Thr Glu Val Tyr Ser Ala Glu Tyr Leu Phe Glu Tyr Asn Ala Glu Ala
            980                 985                 990

Phe Lys Leu Asn Glu Ile Thr Ser  Phe Ser Asp Ser Leu  Phe Val Lys
        995                 1000                1005

Ser Lys  Glu Val Glu Pro Gly  Lys Val Arg Ile Leu  Val Ala Ser
    1010                1015                1020

Leu Gly  Asn Glu Ile Glu Lys  Asp Ser Glu Leu Val  Lys Val Asn
    1025                1030                1035

Leu Thr  Pro Lys Ile Ser Ser  Glu Leu Glu Val Leu  Gly Leu Thr
    1040                1045                1050

Thr Ala  Leu Val Gly Ala Gly  Asp Gly Asn Thr His  Asp Leu Glu
    1055                1060                1065

Leu Ser  Ser Lys Glu Val Lys  Ile Asn Glu Glu Ala  Ser Gly Glu
    1070                1075                1080

Ile Val  Val Asn Pro Val Gln  Asn Phe Glu Ile Pro  Glu Ile Asn
    1085                1090                1095

Lys Lys  Asn Val Lys Leu Thr  Trp Asn Ala Pro Ile  Thr Thr Glu
    1100                1105                1110

Gly Leu  Glu Gly Tyr Val Ile  Tyr Lys Asp Gly Lys  Lys Leu Ser
    1115                1120                1125

Glu Val  Pro Ala Glu Ser Thr  Glu Phe Val Val Ser  Lys Leu Asn
    1130                1135                1140

Arg His  Thr Ile Tyr Asn Phe  Lys Val Ala Ala Lys  Tyr Ser Asn
    1145                1150                1155

Gly Glu  Leu Ser Ala Lys Glu  Ser Lys Thr Ile Arg  Thr Ala Arg
    1160                1165                1170
```

<210> SEQ ID NO 3
<211> LENGTH: 145
<212> TYPE: PRT
<213> ORGANISM: Streptococcus pneumoniae

<400> SEQUENCE: 3

```
Thr Pro Asp Lys Phe Asn Asp Gly Asn Leu Asn Ile Ala Tyr Ala Lys
1               5                   10                  15

Pro Thr Thr Gln Ser Ser Val Asp Tyr Asn Gly Asp Pro Asn Arg Ala
            20                  25                  30

Val Asp Gly Asn Arg Asn Gly Asn Phe Asn Ser Gly Ser Val Thr His
        35                  40                  45

Thr Arg Ala Asp Asn Pro Ser Trp Trp Glu Val Asp Leu Lys Lys Met
    50                  55                  60

Asp Lys Val Gly Leu Val Lys Ile Tyr Asn Arg Thr Asp Ala Glu Thr
```

-continued

```
65                  70                  75                  80

Gln Arg Leu Ser Asn Phe Asp Val Ile Leu Tyr Asp Asn Asn Arg Asn
                85                  90                  95

Glu Val Ala Lys Lys His Val Asn Asn Leu Ser Gly Glu Ser Val Ser
                100                 105                 110

Leu Asp Phe Lys Glu Lys Gly Ala Arg Tyr Ile Lys Val Lys Leu Leu
                115                 120                 125

Thr Ser Gly Val Pro Leu Ser Leu Ala Glu Val Glu Val Phe Arg Glu
        130                 135                 140

Ser
145

<210> SEQ ID NO 4
<211> LENGTH: 896
<212> TYPE: PRT
<213> ORGANISM: Streptococcus pneumoniae

<400> SEQUENCE: 4

Met Asn Lys Glu Lys Ile Lys Arg Lys Leu Ile Thr Ile Leu Phe Val
1               5                   10                  15

Cys Ile Gly Met Leu Cys Phe Gly Leu Leu Ala Gly Val Lys Ala Asp
                20                  25                  30

Asn Arg Val Gln Met Arg Thr Thr Ile Asn Asn Glu Ser Pro Leu Leu
        35                  40                  45

Leu Ser Pro Leu Tyr Gly Asn Asp Asn Gly Asn Gly Leu Trp Trp Gly
        50                  55                  60

Asn Thr Leu Lys Gly Ala Trp Glu Ala Ile Pro Glu Asp Val Lys Pro
65                  70                  75                  80

Tyr Ala Ala Ile Glu Leu His Pro Ala Lys Val Cys Lys Pro Thr Ser
                85                  90                  95

Cys Ile Pro Arg Asp Thr Lys Glu Leu Arg Glu Trp Tyr Val Lys Met
                100                 105                 110

Leu Glu Glu Ala Gln Ser Leu Asn Ile Pro Val Phe Leu Val Ile Met
        115                 120                 125

Ser Ala Gly Glu Arg Asn Thr Val Pro Pro Glu Trp Leu Asp Glu Gln
        130                 135                 140

Phe Gln Lys Tyr Ser Val Leu Lys Gly Val Leu Asn Ile Glu Asn Tyr
145                 150                 155                 160

Trp Ile Tyr Asn Asn Gln Leu Ala Pro His Ser Ala Lys Tyr Leu Glu
                165                 170                 175

Val Cys Ala Lys Tyr Gly Ala His Phe Ile Trp His Asp His Glu Lys
                180                 185                 190

Trp Phe Trp Glu Thr Ile Met Asn Asp Pro Thr Phe Phe Glu Ala Ser
        195                 200                 205

Gln Lys Tyr His Lys Asn Leu Val Leu Ala Thr Lys Asn Thr Pro Ile
        210                 215                 220

Arg Asp Asp Ala Gly Thr Asp Ser Ile Val Ser Gly Phe Trp Leu Ser
225                 230                 235                 240

Gly Leu Cys Asp Asn Trp Gly Ser Ser Thr Asp Thr Trp Lys Trp Trp
                245                 250                 255

Glu Lys His Tyr Thr Asn Thr Phe Glu Thr Gly Arg Ala Arg Asp Met
                260                 265                 270

Arg Ser Tyr Ala Ser Glu Pro Glu Ser Met Ile Ala Met Glu Met Met
        275                 280                 285
```

```
Asn Val Tyr Thr Gly Gly Gly Thr Val Tyr Asn Phe Glu Cys Ala Ala
    290             295             300

Tyr Thr Phe Met Thr Asn Asp Val Pro Thr Pro Ala Phe Thr Lys Gly
305             310             315             320

Ile Ile Pro Phe Phe Arg His Ala Ile Gln Asn Pro Ala Pro Ser Lys
            325             330             335

Glu Glu Val Val Asn Arg Thr Lys Ala Val Phe Trp Asn Gly Glu Gly
            340             345             350

Arg Ile Ser Ser Leu Asn Gly Phe Tyr Gln Gly Leu Tyr Ser Asn Asp
            355             360             365

Glu Thr Met Pro Leu Tyr Asn Asn Gly Arg Tyr His Ile Leu Pro Val
    370             375             380

Ile His Glu Lys Ile Asp Lys Glu Lys Ile Ser Ser Ile Phe Pro Asn
385             390             395             400

Ala Lys Ile Leu Thr Lys Asn Ser Glu Glu Leu Ser Ser Lys Val Asn
            405             410             415

Tyr Leu Asn Ser Leu Tyr Pro Lys Leu Tyr Glu Gly Asp Gly Tyr Ala
            420             425             430

Gln Arg Val Gly Asn Ser Trp Tyr Ile Tyr Asn Ser Asn Ala Asn Ile
            435             440             445

Asn Lys Asn Gln Gln Val Met Leu Pro Met Tyr Thr Asn Asn Thr Lys
    450             455             460

Ser Leu Ser Leu Asp Leu Thr Pro His Thr Tyr Ala Val Val Lys Glu
465             470             475             480

Asn Pro Asn Asn Leu His Ile Leu Leu Asn Asn Tyr Arg Thr Asp Lys
            485             490             495

Thr Ala Met Trp Ala Leu Ser Gly Asn Phe Asp Ala Ser Lys Ser Trp
            500             505             510

Lys Lys Glu Glu Leu Glu Leu Ala Asn Trp Ile Ser Lys Asn Tyr Ser
            515             520             525

Ile Asn Pro Val Asp Asn Asp Phe Arg Thr Thr Thr Leu Thr Leu Lys
    530             535             540

Gly His Thr Gly His Lys Pro Gln Ile Asn Ile Ser Gly Asp Lys Asn
545             550             555             560

His Tyr Thr Tyr Thr Glu Asn Trp Asp Glu Asn Thr His Val Tyr Thr
            565             570             575

Ile Thr Val Asn His Asn Gly Met Val Glu Met Ser Ile Asn Thr Glu
            580             585             590

Gly Thr Gly Pro Val Ser Phe Pro Thr Pro Asp Lys Phe Asn Asp Gly
            595             600             605

Asn Leu Asn Ile Ala Tyr Ala Lys Pro Thr Thr Gln Ser Ser Val Asp
    610             615             620

Tyr Asn Gly Asp Pro Asn Arg Ala Val Asp Gly Asn Arg Asn Gly Asn
625             630             635             640

Phe Asn Ser Gly Ser Val Thr His Thr Arg Ala Asp Asn Pro Ser Trp
            645             650             655

Trp Glu Val Asp Leu Lys Lys Met Asp Lys Val Gly Leu Val Lys Ile
            660             665             670

Tyr Asn Arg Thr Asp Ala Glu Thr Gln Arg Leu Ser Asn Phe Asp Val
            675             680             685

Ile Leu Tyr Asp Asn Asn Arg Asn Glu Val Ala Lys Lys His Val Asn
    690             695             700

Asn Leu Ser Gly Glu Ser Val Ser Leu Asp Phe Lys Glu Lys Gly Ala
```

-continued

```
705              710             715             720

Arg Tyr Ile Lys Val Lys Leu Leu Thr Ser Gly Val Pro Leu Ser Leu
                725             730             735

Ala Glu Val Glu Val Phe Arg Glu Ser Asp Gly Lys Gln Ser Glu Glu
            740             745             750

Asp Ile Asp Lys Ile Thr Glu Asp Lys Val Val Ser Thr Asn Lys Val
            755             760             765

Ala Thr Gln Ser Ser Thr Asn Tyr Glu Gly Val Ala Ala Leu Ala Val
            770             775             780

Asp Gly Asn Lys Asp Gly Asp Tyr Gly His His Ser Val Thr His Thr
785             790             795             800

Lys Glu Asp Ser Pro Ser Trp Trp Glu Ile Asp Leu Ala Gln Thr Glu
            805             810             815

Glu Leu Glu Lys Leu Ile Ile Tyr Asn Arg Thr Asp Ala Glu Ile Gln
            820             825             830

Arg Leu Ser Asn Phe Asp Ile Ile Ile Tyr Asp Ser Asn Asp Tyr Glu
            835             840             845

Val Phe Thr Gln His Ile Asp Ser Leu Glu Ser Asn Asn Leu Ser Ile
    850             855             860

Asp Leu Lys Gly Leu Lys Gly Lys Lys Val Arg Ile Ser Leu Arg Asn
865             870             875             880

Ala Gly Ile Pro Leu Ser Leu Ala Glu Val Glu Val Tyr Thr Tyr Lys
                885             890             895
```

```
<210> SEQ ID NO 5
<211> LENGTH: 165
<212> TYPE: PRT
<213> ORGANISM: Streptomyces avermitilis

<400> SEQUENCE: 5

Ala Pro Ser Leu Glu Gly Ser Ser Trp Ile Trp Phe Pro Glu Gly Glu
1               5               10              15

Pro Ala Asn Ser Ala Pro Ala Ala Thr Arg Trp Phe Arg Arg Thr Val
                20              25              30

Asp Leu Pro Asp Asp Ile Thr Gly Ala Thr Leu Ala Ile Ser Ala Asp
            35              40              45

Asn Val Tyr Ala Val Ser Val Asp Gly Ala Glu Val Ala Arg Thr Asp
        50              55              60

Leu Glu Ala Asp Asn Glu Gly Trp Arg Arg Pro Ala Val Ile Asp Val
65              70              75              80

Leu Asp His Val His Ser Gly Asn Asn Thr Leu Ala Val Ser Ala Ser
                85              90              95

Asn Ala Ser Val Gly Pro Ala Gly Trp Ile Cys Val Leu Val Leu Thr
            100             105             110

Thr Ala Ser Gly Glu Lys Lys Ile Phe Ser Asp Ala Ser Trp Lys Ser
        115             120             125

Thr Asp His Glu Pro Ala Asp Gly Trp Arg Glu Pro Asp Phe Asp Asp
    130             135             140

Ser Gly Trp Pro Ala Ala Lys Val Ala Ala Ala Trp Gly Ala Gly Pro
145             150             155             160

Trp Gly Arg Val Ala
                165
```

```
<210> SEQ ID NO 6
<211> LENGTH: 1030
```

-continued

```
<212> TYPE: PRT
<213> ORGANISM: Streptomyces avermitilis

<400> SEQUENCE: 6

Met Ser Ala Leu Arg Val Thr Ser Pro Ser Val Glu Tyr Val Gln Arg
1               5                   10                  15

Pro Leu Gly Leu Asp Ala Ala His Pro Arg Leu Ser Trp Pro Met Ala
            20                  25                  30

Ser Ala Ala Pro Gly Arg Arg Gln Ser Ala Tyr Gln Val Arg Val Ala
        35                  40                  45

Ser Ser Ala Ala Gly Leu Ser His Pro Asp Val Trp Asp Ser Gly Lys
    50                  55                  60

Val Val Ser Asp Asp Ser Val Leu Val Pro Tyr Ala Gly Pro Pro Leu
65                  70                  75                  80

Lys Pro Arg Thr Arg Tyr Phe Trp Ser Val Arg Val Trp Asp Ala Asp
                85                  90                  95

Gly Gly Ala Ser Glu Trp Ser Ala Pro Ser Trp Trp Glu Thr Gly Leu
            100                 105                 110

Met Gly Ala Ser Gln Trp Ser Ala Lys Trp Ile Ser Ala Pro Ala Pro
        115                 120                 125

Leu Thr Glu Ala Pro Ser Leu Glu Gly Ser Ser Trp Ile Trp Phe Pro
    130                 135                 140

Glu Gly Glu Pro Ala Asn Ser Ala Pro Ala Ala Thr Arg Trp Phe Arg
145                 150                 155                 160

Arg Thr Val Asp Leu Pro Asp Asp Ile Thr Gly Ala Thr Leu Ala Ile
                165                 170                 175

Ser Ala Asp Asn Val Tyr Ala Val Ser Val Asp Gly Ala Glu Val Ala
            180                 185                 190

Arg Thr Asp Leu Glu Ala Asp Asn Glu Gly Trp Arg Arg Pro Ala Val
            195                 200                 205

Ile Asp Val Leu Asp His Val His Ser Gly Asn Asn Thr Leu Ala Val
    210                 215                 220

Ser Ala Ser Asn Ala Ser Val Gly Pro Ala Gly Trp Ile Cys Val Leu
225                 230                 235                 240

Val Leu Thr Thr Ala Ser Gly Glu Lys Lys Ile Phe Ser Asp Ala Ser
                245                 250                 255

Trp Lys Ser Thr Asp His Glu Pro Ala Asp Gly Trp Arg Glu Pro Asp
            260                 265                 270

Phe Asp Asp Ser Gly Trp Pro Ala Ala Lys Val Ala Ala Ala Trp Gly
            275                 280                 285

Ala Gly Pro Trp Gly Arg Val Ala Pro Val Ala Ser Ala Ala Asn Gln
    290                 295                 300

Leu Arg His Glu Phe Arg Leu Pro His Lys Lys Val Ser Arg Ala Arg
305                 310                 315                 320

Leu Tyr Ala Thr Ala Leu Gly Leu Tyr Glu Ala His Leu Asn Gly Arg
                325                 330                 335

Arg Val Gly Arg Asp Gln Leu Ala Pro Gly Trp Thr Asp Tyr Arg Lys
            340                 345                 350

Arg Val Gln Tyr Gln Thr Tyr Asp Val Thr Ser Ser Val Arg Pro Gly
            355                 360                 365

Ala Asn Ala Leu Ala Ala Tyr Val Ala Pro Gly Trp Tyr Ala Gly Asn
    370                 375                 380

Val Gly Met Phe Gly Pro His Gln Tyr Gly Glu Arg Pro Ala Leu Leu
385                 390                 395                 400
```

```
Ala Gln Leu Glu Val Glu Tyr Ala Asp Gly Thr Ser Glu Arg Ile Thr
            405                 410                 415

Ser Gly Pro Asp Trp Arg Ala Ala Ser Gly Pro Ile Val Ser Ala Asp
            420                 425                 430

Leu Leu Ser Gly Glu Thr Tyr Asp Ala Arg Lys Glu Thr Ala Gly Trp
            435                 440                 445

Thr Ser Pro Gly Phe Asp Asp Arg Ala Trp Leu Ala Val Arg Gly Ala
    450                 455                 460

Asp Asn Asp Val Pro Glu Gln Ile Val Ala Gln Val Asp Gly Pro Val
465                 470                 475                 480

Arg Ile Ala Lys Glu Leu Pro Ala Arg Lys Val Thr Glu Pro Lys Pro
                485                 490                 495

Gly Val Phe Val Leu Asp Leu Gly Gln Asn Met Val Gly Ser Val Arg
            500                 505                 510

Leu Arg Val Ser Gly Asp Ala Gly Thr Thr Val Arg Leu Arg His Ala
            515                 520                 525

Glu Val Leu Asn Pro Asp Gly Thr Ile Tyr Thr Ala Asn Leu Arg Ser
    530                 535                 540

Ala Ala Ala Thr Asp Thr Tyr Thr Leu Lys Gly Gln Gly Glu Glu Thr
545                 550                 555                 560

Tyr Glu Pro Arg Phe Thr Phe His Gly Phe Arg Tyr Val Glu Val Thr
                565                 570                 575

Gly Phe Pro Gly Lys Pro Ser Thr Thr Ser Val Thr Gly Arg Val Met
            580                 585                 590

His Thr Ser Ala Pro Phe Thr Phe Glu Phe Glu Thr Asn Val Pro Met
            595                 600                 605

Leu Asn Lys Leu His Ser Asn Ile Thr Trp Gly Gln Arg Gly Asn Phe
    610                 615                 620

Leu Ser Val Pro Thr Asp Thr Pro Ala Arg Asp Glu Arg Leu Gly Trp
625                 630                 635                 640

Thr Gly Asp Ile Asn Val Phe Ala Pro Thr Ala Ala Tyr Thr Met Glu
                645                 650                 655

Ser Ala Arg Phe Leu Thr Lys Trp Leu Val Asp Leu Arg Asp Ala Gln
            660                 665                 670

Thr Ser Asp Gly Ala Phe Thr Asp Val Ala Pro Ala Val Gly Asn Leu
            675                 680                 685

Gly Asn Gly Val Ala Gly Trp Gly Asp Ala Gly Val Thr Val Pro Trp
    690                 695                 700

Ala Leu Tyr Gln Ala Tyr Gly Asp Arg Gln Val Leu Ala Asp Ala Leu
705                 710                 715                 720

Pro Ser Val His Ala Trp Leu Arg Tyr Leu Glu Lys His Ser Asp Gly
                725                 730                 735

Leu Leu Arg Pro Ala Asp Gly Tyr Gly Asp Trp Leu Asn Val Ser Asp
            740                 745                 750

Glu Thr Pro Lys Asp Val Ile Ala Thr Ala Tyr Phe Ala His Ser Ala
            755                 760                 765

Asp Leu Ala Ala Arg Met Ala Thr Glu Leu Gly Lys Asp Ala Ala Pro
    770                 775                 780

Tyr Thr Asp Leu Phe Thr Arg Ile Arg Lys Ala Phe Gln Thr Ala Tyr
785                 790                 795                 800

Val Ala Ser Asp Gly Lys Val Lys Gly Asp Thr Gln Ser Ala Tyr Val
                805                 810                 815
```

-continued

```
Leu Thr Leu Ser Met Asn Leu Val Pro Asp Ala Leu Arg Lys Ala Ala
            820                 825                 830

Ala Asp Arg Leu Val Ala Leu Ile Glu Ala Lys Asp Trp His Leu Ser
            835                 840                 845

Thr Gly Phe Leu Gly Thr Pro Arg Leu Leu Pro Val Leu Thr Asp Thr
            850                 855                 860

Gly His Thr Asp Val Ala Tyr Arg Leu Leu His Gln Arg Thr Phe Pro
865                 870                 875                 880

Ser Trp Gly Tyr Pro Ile Asp Lys Gly Ser Thr Thr Met Trp Glu Arg
                885                 890                 895

Trp Asp Ser Ile Gln Pro Asp Gly Gly Phe Gln Thr Pro Glu Met Asn
            900                 905                 910

Ser Phe Asn His Tyr Ala Tyr Gly Ser Val Gly Glu Trp Met Tyr Ala
            915                 920                 925

Asn Ile Ala Gly Ile Ala Pro Gly Arg Ala Gly Tyr Arg Gln Val Val
            930                 935                 940

Ile Arg Pro Arg Pro Gly Gly Glu Val Thr Ser Ala Arg Ala Thr Phe
945                 950                 955                 960

Ala Ser Leu His Gly Pro Val Ser Thr Arg Trp Gln Gln Arg Ser Gly
                965                 970                 975

Gly Phe Val Leu Thr Cys Ser Val Pro Pro Asn Thr Thr Ala Glu Val
            980                 985                 990

Trp Ile Pro Ala Asp His Pro Asp  Arg Val Gln His Thr  His Gly Thr
            995                 1000                1005

Phe Val  Arg Ala Glu Asp Gly  Cys Ala Val Phe Glu  Val Gly Ser
    1010                1015                1020

Gly Ser  His Arg Phe Thr Val
    1025                1030

<210> SEQ ID NO 7
<211> LENGTH: 159
<212> TYPE: PRT
<213> ORGANISM: Streptococcus pneumoniae

<400> SEQUENCE: 7

Asn Leu Val Glu Asn Gly Asp Phe Gly Gln Thr Glu Asp Gly Ser Ser
1               5                   10                  15

Pro Trp Thr Gly Ser Lys Ala Gln Gly Trp Ser Ala Trp Val Asp Gln
            20                  25                  30

Lys Asn Ser Ala Asp Ala Ser Thr Arg Val Ile Glu Ala Lys Asp Gly
        35                  40                  45

Ala Ile Thr Ile Ser Ser His Glu Lys Leu Arg Ala Ala Leu His Arg
    50                  55                  60

Met Val Pro Ile Glu Ala Lys Lys Lys Tyr Lys Leu Arg Phe Lys Ile
65                  70                  75                  80

Lys Thr Asp Asn Lys Ile Gly Ile Ala Lys Val Arg Ile Ile Glu Glu
                85                  90                  95

Ser Gly Lys Asp Lys Arg Leu Trp Asn Ser Ala Thr Thr Ser Gly Thr
            100                 105                 110

Lys Asp Trp Gln Thr Ile Glu Ala Asp Tyr Ser Pro Thr Leu Asp Val
            115                 120                 125

Asp Lys Ile Lys Leu Glu Leu Phe Tyr Glu Thr Gly Thr Gly Thr Val
        130                 135                 140

Ser Phe Lys Asp Ile Glu Leu Val Glu Val Ala Asp Gln Leu Ser
145                 150                 155
```

<210> SEQ ID NO 8
<211> LENGTH: 1066
<212> TYPE: PRT
<213> ORGANISM: Streptococcus pneumoniae

<400> SEQUENCE: 8

Met Gln Thr Lys Thr Lys Lys Leu Ile Val Ser Leu Ser Ser Leu Val
1               5                   10                  15

Leu Ser Gly Phe Leu Leu Asn His Tyr Met Thr Ile Gly Ala Glu Glu
                20                  25                  30

Thr Thr Thr Asn Thr Ile Gln Gln Ser Gln Lys Glu Val Gln Tyr Gln
            35                  40                  45

Gln Arg Asp Thr Lys Asn Leu Val Glu Asn Gly Asp Phe Gly Gln Thr
        50                  55                  60

Glu Asp Gly Ser Ser Pro Trp Thr Gly Ser Lys Ala Gln Gly Trp Ser
65                  70                  75                  80

Ala Trp Val Asp Gln Lys Asn Ser Ala Asp Ala Ser Thr Arg Val Ile
                85                  90                  95

Glu Ala Lys Asp Gly Ala Ile Thr Ile Ser Ser His Glu Lys Leu Arg
            100                 105                 110

Ala Ala Leu His Arg Met Val Pro Ile Glu Ala Lys Lys Lys Tyr Lys
        115                 120                 125

Leu Arg Phe Lys Ile Lys Thr Asp Asn Lys Ile Gly Ile Ala Lys Val
        130                 135                 140

Arg Ile Ile Glu Glu Ser Gly Lys Asp Lys Arg Leu Trp Asn Ser Ala
145                 150                 155                 160

Thr Thr Ser Gly Thr Lys Asp Trp Gln Thr Ile Glu Ala Asp Tyr Ser
                165                 170                 175

Pro Thr Leu Asp Val Asp Lys Ile Lys Leu Glu Leu Phe Tyr Glu Thr
            180                 185                 190

Gly Thr Gly Thr Val Ser Phe Lys Asp Ile Glu Leu Val Glu Val Ala
        195                 200                 205

Asp Gln Leu Ser Glu Asp Ser Gln Thr Asp Lys Gln Leu Glu Glu Lys
        210                 215                 220

Ile Asp Leu Pro Ile Gly Lys Lys His Val Phe Ser Leu Ala Asp Tyr
225                 230                 235                 240

Thr Tyr Lys Val Glu Asn Pro Asp Val Ala Ser Val Lys Asn Gly Ile
                245                 250                 255

Leu Glu Pro Leu Lys Glu Gly Thr Thr Asn Val Ile Val Ser Lys Asp
            260                 265                 270

Gly Lys Glu Val Lys Lys Ile Pro Leu Lys Ile Leu Ala Ser Val Lys
        275                 280                 285

Asp Ala Tyr Thr Asp Arg Leu Asp Asp Trp Asn Gly Ile Ile Ala Gly
        290                 295                 300

Asn Gln Tyr Tyr Asp Ser Lys Asn Glu Gln Met Ala Lys Leu Asn Gln
305                 310                 315                 320

Glu Leu Glu Gly Lys Val Ala Asp Ser Leu Ser Ser Ile Ser Ser Gln
            325                 330                 335

Ala Asp Arg Thr Tyr Leu Trp Glu Lys Phe Ser Asn Tyr Lys Thr Ser
        340                 345                 350

Ala Asn Leu Thr Ala Thr Tyr Arg Lys Leu Glu Glu Met Ala Lys Gln
        355                 360                 365

Val Thr Asn Pro Ser Ser Arg Tyr Tyr Gln Asp Glu Thr Val Val Arg

-continued

```
     370             375             380

Thr Val Arg Asp Ser Met Glu Trp Met His Lys His Val Tyr Asn Ser
385             390             395             400

Glu Lys Ser Ile Val Gly Asn Trp Trp Asp Tyr Glu Ile Gly Thr Pro
                405             410             415

Arg Ala Ile Asn Asn Thr Leu Ser Leu Met Lys Glu Tyr Phe Ser Asp
                420             425             430

Glu Glu Ile Lys Lys Tyr Thr Asp Val Ile Glu Lys Phe Val Pro Asp
                435             440             445

Pro Glu His Phe Arg Lys Thr Thr Asp Asn Pro Phe Lys Ala Leu Gly
        450             455             460

Gly Asn Leu Val Asp Met Gly Arg Val Lys Val Ile Ala Gly Leu Leu
465             470             475             480

Arg Lys Asp Asp Gln Glu Ile Ser Ser Thr Ile Arg Ser Ile Glu Gln
                485             490             495

Val Phe Lys Leu Val Asp Gln Gly Glu Gly Phe Tyr Gln Asp Gly Ser
                500             505             510

Tyr Ile Asp His Thr Asn Val Ala Tyr Thr Gly Ala Tyr Gly Asn Val
                515             520             525

Leu Ile Asp Gly Leu Ser Gln Leu Leu Pro Val Ile Gln Lys Thr Lys
        530             535             540

Asn Pro Ile Asp Lys Asp Lys Met Gln Thr Met Tyr His Trp Ile Asp
545             550             555             560

Lys Ser Phe Ala Pro Leu Leu Val Asn Gly Glu Leu Met Asp Met Ser
                565             570             575

Arg Gly Arg Ser Ile Ser Arg Ala Asn Ser Glu Gly His Val Ala Ala
                580             585             590

Val Glu Val Leu Arg Gly Ile His Arg Ile Ala Asp Met Ser Glu Gly
                595             600             605

Glu Thr Lys Gln Cys Leu Gln Ser Leu Val Lys Thr Ile Val Gln Ser
        610             615             620

Asp Ser Tyr Tyr Asp Val Phe Lys Asn Leu Lys Thr Tyr Lys Asp Ile
625             630             635             640

Ser Leu Met Gln Ser Leu Leu Ser Asp Ala Gly Val Ala Ser Val Pro
                645             650             655

Arg Pro Ser Tyr Leu Ser Ala Phe Asn Lys Met Asp Lys Thr Ala Met
                660             665             670

Tyr Asn Ala Glu Lys Gly Phe Gly Phe Gly Leu Ser Leu Phe Ser Ser
                675             680             685

Arg Thr Leu Asn Tyr Glu His Met Asn Lys Glu Asn Lys Arg Gly Trp
        690             695             700

Tyr Thr Ser Asp Gly Met Phe Tyr Leu Tyr Asn Gly Asp Leu Ser His
705             710             715             720

Tyr Ser Asp Gly Tyr Trp Pro Thr Val Asn Pro Tyr Lys Met Pro Gly
                725             730             735

Thr Thr Glu Thr Asp Ala Lys Arg Ala Asp Ser Asp Thr Gly Lys Val
                740             745             750

Leu Pro Ser Ala Phe Val Gly Thr Ser Lys Leu Asp Asp Ala Asn Ala
                755             760             765

Thr Ala Thr Met Asp Phe Thr Asn Trp Asn Gln Thr Leu Thr Ala His
        770             775             780

Lys Ser Trp Phe Met Leu Lys Asp Lys Ile Ala Phe Leu Gly Ser Asn
785             790             795             800
```

```
Ile Gln Asn Thr Ser Thr Asp Thr Ala Ala Thr Thr Ile Asp Gln Arg
              805                 810                 815

Lys Leu Glu Ser Gly Asn Pro Tyr Lys Val Tyr Val Asn Asp Lys Glu
              820                 825                 830

Ala Ser Leu Thr Glu Gln Glu Lys Asp Tyr Pro Glu Thr Gln Ser Val
              835                 840                 845

Phe Leu Glu Ser Phe Asp Ser Lys Lys Asn Ile Gly Tyr Phe Phe Phe
      850                 855                 860

Lys Lys Ser Ser Ile Ser Met Ser Lys Ala Leu Gln Lys Gly Ala Trp
865                 870                 875                 880

Lys Asp Ile Asn Glu Gly Gln Ser Asp Lys Glu Val Glu Asn Glu Phe
              885                 890                 895

Leu Thr Ile Ser Gln Ala His Lys Gln Asn Arg Asp Ser Tyr Gly Tyr
              900                 905                 910

Met Leu Ile Pro Asn Val Asp Arg Ala Thr Phe Asn Gln Met Ile Lys
              915                 920                 925

Glu Leu Glu Ser Ser Leu Ile Glu Asn Asn Glu Thr Leu Gln Ser Val
      930                 935                 940

Tyr Asp Ala Lys Gln Gly Val Trp Gly Ile Val Lys Tyr Asp Asp Ser
945                 950                 955                 960

Val Ser Thr Ile Ser Asn Gln Phe Gln Val Leu Lys Arg Gly Val Tyr
              965                 970                 975

Thr Ile Arg Lys Glu Gly Asp Glu Tyr Lys Ile Ala Tyr Tyr Asn Pro
              980                 985                 990

Glu Thr Gln Glu Ser Ala Pro Asp  Gln Glu Val Phe Lys  Lys Leu Glu
              995                 1000                1005

Gln Ala  Ala Gln Pro Gln Val  Gln Asn Ser Lys Glu  Lys Glu Lys
      1010                1015                1020

Ser Glu  Glu Glu Lys Asn His  Ser Asp Gln Lys Asn  Leu Pro Gln
      1025                1030                1035

Thr Gly  Glu Gly Gln Ser Ile  Leu Ala Ser Leu Gly  Phe Leu Leu
      1040                1045                1050

Leu Gly  Ala Phe Tyr Leu Phe  Arg Arg Gly Lys Asn  Asn
      1055                1060                1065
```

```
<210> SEQ ID NO 9
<211> LENGTH: 5
<212> TYPE: PRT
<213> ORGANISM: Artificial Sequence
<220> FEATURE:
<223> OTHER INFORMATION: Synthetic peptide

<400> SEQUENCE: 9

Ala Leu Asn Gly Ser
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic peptide

<400> SEQUENCE: 10

Leu Gln Ala Leu Gly
1               5
```

```
<210> SEQ ID NO 11
<211> LENGTH: 5
<212> TYPE: PRT
<213> ORGANISM: Artificial Sequence
<220> FEATURE:
<223> OTHER INFORMATION: Synthetic peptide

<400> SEQUENCE: 11

Gly Gly Asn Ser Gly
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic peptide

<400> SEQUENCE: 12

Gly Gly Gly Ser Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic peptide

<400> SEQUENCE: 13

Gly Gly Ser Leu Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic peptide

<400> SEQUENCE: 14

Gly Gly Gly Ser Ala
1               5

<210> SEQ ID NO 15
<211> LENGTH: 10
<212> TYPE: PRT
<213> ORGANISM: Artificial Sequence
<220> FEATURE:
<223> OTHER INFORMATION: Synthetic peptide

<400> SEQUENCE: 15

Ala Leu Asn Gly Ser Gly Gly Gly Ser Gly
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic peptide

<400> SEQUENCE: 16

Leu Gln Ala Leu Gly Gly Gly Gly Ser Leu
1               5                   10

<210> SEQ ID NO 17
```

-continued

```
<211> LENGTH: 15
<212> TYPE: PRT
<213> ORGANISM: Artificial Sequence
<220> FEATURE:
<223> OTHER INFORMATION: Synthetic peptide

<400> SEQUENCE: 17

Ala Leu Asn Gly Ser Gly Gly Gly Ser Gly Gly Gly Gly Ser Gly
1               5                   10                  15

<210> SEQ ID NO 18
<211> LENGTH: 438
<212> TYPE: PRT
<213> ORGANISM: Pseudomonas aeruginosa

<400> SEQUENCE: 18

Met Asn Thr Tyr Phe Asp Ile Pro His Arg Leu Val Gly Lys Ala Leu
1               5                   10                  15

Tyr Glu Ser Tyr Tyr Asp His Phe Gly Gln Met Asp Ile Leu Ser Asp
                20                  25                  30

Gly Ser Leu Tyr Leu Ile Tyr Arg Arg Ala Thr Glu His Val Gly Gly
        35                  40                  45

Ser Asp Gly Arg Val Val Phe Ser Lys Leu Glu Gly Gly Ile Trp Ser
    50                  55                  60

Ala Pro Thr Ile Val Ala Gln Ala Gly Gly Gln Asp Phe Arg Asp Val
65                  70                  75                  80

Ala Gly Gly Thr Met Pro Ser Gly Arg Ile Val Ala Ala Ser Thr Val
                85                  90                  95

Tyr Glu Thr Gly Glu Val Lys Val Tyr Val Ser Asp Asp Ser Gly Val
                100                 105                 110

Thr Trp Val His Lys Phe Thr Leu Ala Arg Gly Gly Ala Asp Tyr Asn
        115                 120                 125

Phe Ala His Gly Lys Ser Phe Gln Val Gly Ala Arg Tyr Val Ile Pro
    130                 135                 140

Leu Tyr Ala Ala Thr Gly Val Asn Tyr Glu Leu Lys Trp Leu Glu Ser
145                 150                 155                 160

Ser Asp Gly Gly Glu Thr Trp Gly Glu Gly Ser Thr Ile Tyr Ser Gly
                165                 170                 175

Asn Thr Pro Tyr Asn Glu Thr Ser Tyr Leu Pro Val Gly Asp Gly Val
                180                 185                 190

Ile Leu Ala Val Ala Arg Val Gly Ser Gly Ala Gly Gly Ala Leu Arg
        195                 200                 205

Gln Phe Ile Ser Leu Asp Asp Gly Gly Thr Trp Thr Asp Gln Gly Asn
    210                 215                 220

Val Thr Ala Gln Asn Gly Asp Ser Thr Asp Ile Leu Val Ala Pro Ser
225                 230                 235                 240

Leu Ser Tyr Ile Tyr Ser Glu Gly Gly Thr Pro His Val Val Leu Leu
                245                 250                 255

Tyr Thr Asn Arg Thr Thr His Phe Cys Tyr Tyr Arg Thr Ile Leu Leu
                260                 265                 270

Ala Lys Ala Val Ala Gly Ser Ser Gly Trp Thr Glu Arg Val Pro Val
        275                 280                 285

Tyr Ser Ala Pro Ala Ala Ser Gly Tyr Thr Ser Gln Val Val Leu Gly
    290                 295                 300

Gly Arg Arg Ile Leu Gly Asn Leu Phe Arg Glu Thr Ser Ser Thr Thr
305                 310                 315                 320
```

Ser Gly Ala Tyr Gln Phe Glu Val Tyr Leu Gly Gly Val Pro Asp Phe
                325                 330                 335

Glu Ser Asp Trp Phe Ser Val Ser Ser Asn Ser Leu Tyr Thr Leu Ser
            340                 345                 350

His Gly Leu Gln Arg Ser Pro Arg Arg Val Val Val Glu Phe Ala Arg
        355                 360                 365

Ser Ser Ser Pro Ser Thr Trp Asn Ile Val Met Pro Ser Tyr Phe Asn
    370                 375                 380

Asp Gly Gly His Lys Gly Ser Gly Ala Gln Val Glu Val Gly Ser Leu
385                 390                 395                 400

Asn Ile Arg Leu Gly Thr Gly Ala Ala Val Trp Gly Thr Gly Tyr Phe
                405                 410                 415

Gly Gly Ile Asp Asn Ser Ala Thr Thr Arg Phe Ala Thr Gly Tyr Tyr
            420                 425                 430

Arg Val Arg Ala Trp Ile
        435

<210> SEQ ID NO 19
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 19

Val Pro Asp Phe Glu Ser Asp Trp Phe Ser Val Ser Ser Asn Ser Leu
1                 5                   10                  15

Tyr Thr Leu Ser His Gly Leu Gln Arg Ser Pro Arg Arg Val Val Val
            20                  25                  30

Glu Phe Ala Arg Ser Ser Ser Pro Ser Thr Trp Asn Ile Val Met Pro
        35                  40                  45

Ser Tyr Phe Asn Asp Gly Gly His Lys Gly Ser Gly Ala Gln Val Glu
    50                  55                  60

Val Gly Ser Leu Asn Ile Arg Leu Gly Thr Gly Ala Ala Val Trp Gly
65                  70                  75                  80

Thr Gly Tyr Phe Gly Gly Ile Asp Asn Ser Ala Thr Thr Arg Phe Ala
                85                  90                  95

Thr Gly Tyr Tyr Arg Val Arg Ala Trp Ile
            100                 105

<210> SEQ ID NO 20
<211> LENGTH: 397
<212> TYPE: PRT
<213> ORGANISM: Artificial Sequence
<220> FEATURE:
<223> OTHER INFORMATION: Synthetic polypeptide

<400> SEQUENCE: 20

Gly Ala Met Ala Ile Ile Glu Thr Ala Ile Pro Gln Ser Glu Met Thr
1                 5                   10                  15

Ala Ser Ala Thr Ser Glu Glu Gly Gln Asp Pro Ala Ser Ser Ala Ile
            20                  25                  30

Asp Gly Asn Thr Asn Thr Met Trp His Thr Lys Trp Asn Gly Ser Asp
        35                  40                  45

Ala Leu Pro Gln Ser Leu Ser Val Asn Leu Gly Ser Ser Arg Lys Val
    50                  55                  60

Ser Ser Ile Ala Ile Thr Pro Arg Thr Ser Gly Asn Asn Gly Phe Ile
65                  70                  75                  80

-continued

```
Thr Lys Tyr Glu Ile His Ala Ile Asn Asn Gly Val Glu Thr Leu Val
                85                  90                  95

Ala Glu Gly Thr Trp Glu Glu Asn Asn Leu Val Lys Thr Val Thr Phe
            100                 105                 110

Asp Ser Pro Ile Asp Ala Glu Glu Ile Lys Ile Thr Ala Ile Gln Gly
        115                 120                 125

Val Gly Gly Phe Ala Ser Ile Ala Glu Leu Asn Val Tyr Glu Gly Gly
    130                 135                 140

Gly Ser Gly Ala Ile Ile Glu Thr Ala Ile Pro Gln Ser Glu Met Thr
145                 150                 155                 160

Ala Ser Ala Thr Ser Glu Glu Gly Gln Asp Pro Ala Ser Ser Ala Ile
                165                 170                 175

Asp Gly Asn Thr Asn Thr Met Trp His Thr Lys Trp Asn Gly Ser Asp
            180                 185                 190

Ala Leu Pro Gln Ser Leu Ser Val Asn Leu Gly Ser Ser Arg Lys Val
        195                 200                 205

Ser Ser Ile Ala Ile Thr Pro Arg Thr Ser Gly Asn Asn Gly Phe Ile
    210                 215                 220

Thr Lys Tyr Glu Ile His Ala Ile Asn Asn Gly Val Glu Thr Leu Val
225                 230                 235                 240

Ala Glu Gly Thr Trp Glu Glu Asn Asn Leu Val Lys Thr Val Thr Phe
                245                 250                 255

Asp Ser Pro Ile Asp Ala Glu Glu Ile Lys Ile Thr Ala Ile Gln Gly
            260                 265                 270

Val Gly Gly Phe Ala Ser Ile Ala Glu Leu Asn Val Tyr Glu Gly Gly
        275                 280                 285

Ser Leu Gly Val Pro Asp Phe Glu Ser Asp Trp Phe Ser Val Ser Ser
    290                 295                 300

Asn Ser Leu Tyr Thr Leu Ser His Gly Leu Gln Arg Ser Pro Arg Arg
305                 310                 315                 320

Val Val Val Glu Phe Ala Arg Ser Ser Ser Pro Ser Thr Trp Asn Ile
                325                 330                 335

Val Met Pro Ser Tyr Phe Asn Asp Gly Gly His Lys Gly Ser Gly Ala
            340                 345                 350

Gln Val Glu Val Gly Ser Leu Asn Ile Arg Leu Gly Thr Gly Ala Ala
        355                 360                 365

Val Trp Gly Thr Gly Tyr Phe Gly Gly Ile Asp Asn Ser Ala Thr Thr
    370                 375                 380

Arg Phe Ala Thr Gly Tyr Tyr Arg Val Arg Ala Trp Ile
385                 390                 395
```

```
<210> SEQ ID NO 21
<211> LENGTH: 410
<212> TYPE: PRT
<213> ORGANISM: Artificial Sequence
<220> FEATURE:
<223> OTHER INFORMATION: Synthetic polypeptide

<400> SEQUENCE: 21
```

```
Gly Ala Met Gly Thr Pro Asp Lys Phe Asn Asp Gly Asn Leu Asn Ile
1               5                   10                  15

Ala Tyr Ala Lys Pro Thr Thr Gln Ser Ser Val Asp Tyr Asn Gly Asp
            20                  25                  30

Pro Asn Arg Ala Val Asp Gly Asn Arg Asn Gly Asn Phe Asn Ser Gly
        35                  40                  45
```

-continued

```
Ser Val Thr His Thr Arg Ala Asp Asn Pro Ser Trp Trp Glu Val Asp
    50                  55                  60

Leu Lys Lys Met Asp Lys Val Gly Leu Val Lys Ile Tyr Asn Arg Thr
65                  70                  75                  80

Asp Ala Glu Thr Gln Arg Leu Ser Asn Phe Asp Val Ile Leu Tyr Asp
                85                  90                  95

Asn Asn Arg Asn Glu Val Ala Lys Lys His Val Asn Asn Leu Ser Gly
                100                 105                 110

Glu Ser Val Ser Leu Asp Phe Lys Glu Lys Gly Ala Arg Tyr Ile Lys
        115                 120                 125

Val Lys Leu Leu Thr Ser Gly Val Pro Leu Ser Leu Ala Glu Val Glu
    130                 135                 140

Val Phe Arg Glu Ser Gly Gly Gly Ser Ala Thr Pro Asp Lys Phe Asn
145                 150                 155                 160

Asp Gly Asn Leu Asn Ile Ala Tyr Ala Lys Pro Thr Thr Gln Ser Ser
                165                 170                 175

Val Asp Tyr Asn Gly Asp Pro Asn Arg Ala Val Asp Gly Asn Arg Asn
                180                 185                 190

Gly Asn Phe Asn Ser Gly Ser Val Thr His Thr Arg Ala Asp Asn Pro
        195                 200                 205

Ser Trp Trp Glu Val Asp Leu Lys Lys Met Asp Lys Val Gly Leu Val
    210                 215                 220

Lys Ile Tyr Asn Arg Thr Asp Ala Glu Thr Gln Arg Leu Ser Asn Phe
225                 230                 235                 240

Asp Val Ile Leu Tyr Asp Asn Asn Arg Asn Glu Val Ala Lys Lys His
                245                 250                 255

Val Asn Asn Leu Ser Gly Glu Ser Val Ser Leu Asp Phe Lys Glu Lys
                260                 265                 270

Gly Ala Arg Tyr Ile Lys Val Lys Leu Leu Thr Ser Gly Val Pro Leu
        275                 280                 285

Ser Leu Ala Glu Val Glu Val Phe Arg Glu Ser Gly Gly Ser Leu Gly
    290                 295                 300

Val Pro Asp Phe Glu Ser Asp Trp Phe Ser Val Ser Ser Asn Ser Leu
305                 310                 315                 320

Tyr Thr Leu Ser His Gly Leu Gln Arg Ser Pro Arg Arg Val Val Val
                325                 330                 335

Glu Phe Ala Arg Ser Ser Ser Pro Ser Thr Trp Asn Ile Val Met Pro
                340                 345                 350

Ser Tyr Phe Asn Asp Gly Gly His Lys Gly Ser Gly Ala Gln Val Glu
        355                 360                 365

Val Gly Ser Leu Asn Ile Arg Leu Gly Thr Gly Ala Ala Val Trp Gly
    370                 375                 380

Thr Gly Tyr Phe Gly Gly Ile Asp Asn Ser Ala Thr Thr Arg Phe Ala
385                 390                 395                 400

Thr Gly Tyr Tyr Arg Val Arg Ala Trp Ile
                405                 410
```

<210> SEQ ID NO 22
<211> LENGTH: 449
<212> TYPE: PRT
<213> ORGANISM: Artificial Sequence
<220> FEATURE:
<223> OTHER INFORMATION: Synthetic polypeptide

<400> SEQUENCE: 22

-continued

```
Gly Ala Met Ala Pro Ser Leu Glu Gly Ser Ser Trp Ile Trp Phe Pro
1               5                   10                  15

Glu Gly Glu Pro Ala Asn Ser Ala Pro Ala Ala Thr Arg Trp Phe Arg
                20                  25                  30

Arg Thr Val Asp Leu Pro Asp Asp Ile Thr Gly Ala Thr Leu Ala Ile
            35                  40                  45

Ser Ala Asp Asn Val Tyr Ala Val Ser Val Asp Gly Ala Glu Val Ala
        50                  55                  60

Arg Thr Asp Leu Glu Ala Asp Asn Glu Gly Trp Arg Arg Pro Ala Val
65                  70                  75                  80

Ile Asp Val Leu Asp His Val His Ser Gly Asn Asn Thr Leu Ala Val
                85                  90                  95

Ser Ala Ser Asn Ala Ser Val Gly Pro Ala Gly Trp Ile Cys Val Leu
            100                 105                 110

Val Leu Thr Thr Ala Ser Gly Glu Lys Lys Ile Phe Ser Asp Ala Ser
            115                 120                 125

Trp Lys Ser Thr Asp His Glu Pro Ala Asp Gly Trp Arg Glu Pro Asp
        130                 135                 140

Phe Asp Asp Ser Gly Trp Pro Ala Ala Lys Val Ala Ala Ala Trp Gly
145                 150                 155                 160

Ala Gly Pro Trp Gly Arg Val Ala Gly Gly Gly Ser Gly Ala Pro Ser
                165                 170                 175

Leu Glu Gly Ser Ser Trp Ile Trp Phe Pro Glu Gly Glu Pro Ala Asn
            180                 185                 190

Ser Ala Pro Ala Ala Thr Arg Trp Phe Arg Arg Thr Val Asp Leu Pro
            195                 200                 205

Asp Asp Ile Thr Gly Ala Thr Leu Ala Ile Ser Ala Asp Asn Val Tyr
        210                 215                 220

Ala Val Ser Val Asp Gly Ala Glu Val Ala Arg Thr Asp Leu Glu Ala
225                 230                 235                 240

Asp Asn Glu Gly Trp Arg Arg Pro Ala Val Ile Asp Val Leu Asp His
                245                 250                 255

Val His Ser Gly Asn Asn Thr Leu Ala Val Ser Ala Ser Asn Ala Ser
            260                 265                 270

Val Gly Pro Ala Gly Trp Ile Cys Val Leu Val Leu Thr Thr Ala Ser
            275                 280                 285

Gly Glu Lys Lys Ile Phe Ser Asp Ala Ser Trp Lys Ser Thr Asp His
        290                 295                 300

Glu Pro Ala Asp Gly Trp Arg Glu Pro Asp Phe Asp Asp Ser Gly Trp
305                 310                 315                 320

Pro Ala Ala Lys Val Ala Ala Ala Trp Gly Ala Gly Pro Trp Gly Arg
                325                 330                 335

Val Ala Gly Gly Ser Leu Gly Val Pro Asp Phe Glu Ser Asp Trp Phe
            340                 345                 350

Ser Val Ser Ser Asn Ser Leu Tyr Thr Leu Ser His Gly Leu Gln Arg
            355                 360                 365

Ser Pro Arg Arg Val Val Val Glu Phe Ala Arg Ser Ser Ser Pro Ser
        370                 375                 380

Thr Trp Asn Ile Val Met Pro Ser Tyr Phe Asn Asp Gly Gly His Lys
385                 390                 395                 400

Gly Ser Gly Ala Gln Val Glu Val Gly Ser Leu Asn Ile Arg Leu Gly
                405                 410                 415
```

```
Thr Gly Ala Ala Val Trp Gly Thr Gly Tyr Phe Gly Gly Ile Asp Asn
            420                     425                     430

Ser Ala Thr Thr Arg Phe Ala Thr Gly Tyr Tyr Arg Val Arg Ala Trp
        435                     440                     445

Ile

<210> SEQ ID NO 23
<211> LENGTH: 437
<212> TYPE: PRT
<213> ORGANISM: Artificial Sequence
<220> FEATURE:
<223> OTHER INFORMATION: Synthetic polypeptide

<400> SEQUENCE: 23

Gly Ala Met Glu Asn Leu Val Glu Asn Gly Asp Phe Gly Gln Thr Glu
1               5                   10                  15

Asp Gly Ser Ser Pro Trp Thr Gly Ser Lys Ala Gln Gly Trp Ser Ala
            20                  25                  30

Trp Val Asp Gln Lys Asn Ser Ala Asp Ala Ser Thr Arg Val Ile Glu
        35                  40                  45

Ala Lys Asp Gly Ala Ile Thr Ile Ser Ser His Glu Lys Leu Arg Ala
    50                  55                  60

Ala Leu His Arg Met Val Pro Ile Glu Ala Lys Lys Lys Tyr Lys Leu
65                  70                  75                  80

Arg Phe Lys Ile Lys Thr Asp Asn Lys Ile Gly Ile Ala Lys Val Arg
                85                  90                  95

Ile Ile Glu Glu Ser Gly Lys Asp Lys Arg Leu Trp Asn Ser Ala Thr
            100                 105                 110

Thr Ser Gly Thr Lys Asp Trp Gln Thr Ile Glu Ala Asp Tyr Ser Pro
        115                 120                 125

Thr Leu Asp Val Asp Lys Ile Lys Leu Glu Leu Phe Tyr Glu Thr Gly
    130                 135                 140

Thr Gly Thr Val Ser Phe Lys Asp Ile Glu Leu Val Glu Val Ala Asp
145                 150                 155                 160

Gln Leu Ser Gly Gly Gly Ser Gly Asn Leu Val Glu Asn Gly Asp Phe
                165                 170                 175

Gly Gln Thr Glu Asp Gly Ser Ser Pro Trp Thr Gly Ser Lys Ala Gln
            180                 185                 190

Gly Trp Ser Ala Trp Val Asp Gln Lys Asn Ser Ala Asp Ala Ser Thr
        195                 200                 205

Arg Val Ile Glu Ala Lys Asp Gly Ala Ile Thr Ile Ser Ser His Glu
    210                 215                 220

Lys Leu Arg Ala Ala Leu His Arg Met Val Pro Ile Glu Ala Lys Lys
225                 230                 235                 240

Lys Tyr Lys Leu Arg Phe Lys Ile Lys Thr Asp Asn Lys Ile Gly Ile
                245                 250                 255

Ala Lys Val Arg Ile Ile Glu Glu Ser Gly Lys Asp Lys Arg Leu Trp
            260                 265                 270

Asn Ser Ala Thr Thr Ser Gly Thr Lys Asp Trp Gln Thr Ile Glu Ala
        275                 280                 285

Asp Tyr Ser Pro Thr Leu Asp Val Asp Lys Ile Lys Leu Glu Leu Phe
    290                 295                 300

Tyr Glu Thr Gly Thr Gly Thr Val Ser Phe Lys Asp Ile Glu Leu Val
305                 310                 315                 320

Glu Val Ala Asp Gln Leu Ser Gly Gly Ser Leu Gly Val Pro Asp Phe
```

-continued

```
                    325             330             335
Glu Ser Asp Trp Phe Ser Val Ser Ser Asn Ser Leu Tyr Thr Leu Ser
            340             345             350
His Gly Leu Gln Arg Ser Pro Arg Arg Val Val Val Glu Phe Ala Arg
            355             360             365
Ser Ser Ser Pro Ser Thr Trp Asn Ile Val Met Pro Ser Tyr Phe Asn
        370             375             380
Asp Gly Gly His Lys Gly Ser Gly Ala Gln Val Glu Val Gly Ser Leu
385             390             395             400
Asn Ile Arg Leu Gly Thr Gly Ala Ala Val Trp Gly Thr Gly Tyr Phe
                405             410             415
Gly Gly Ile Asp Asn Ser Ala Thr Thr Arg Phe Ala Thr Gly Tyr Tyr
            420             425             430
Arg Val Arg Ala Trp
        435

<210> SEQ ID NO 24
<211> LENGTH: 781
<212> TYPE: PRT
<213> ORGANISM: Vibrio cholerae

<400> SEQUENCE: 24

Met Arg Phe Lys Asn Val Lys Lys Thr Ala Leu Met Leu Ala Met Phe
1               5               10              15
Gly Met Ala Thr Ser Ser Asn Ala Ala Leu Phe Asp Tyr Asn Ala Thr
            20              25              30
Gly Asp Thr Glu Phe Asp Ser Pro Ala Lys Gln Gly Trp Met Gln Asp
        35              40              45
Asn Thr Asn Asn Gly Ser Gly Val Leu Thr Asn Ala Asp Gly Met Pro
    50              55              60
Ala Trp Leu Val Gln Gly Ile Gly Gly Arg Ala Gln Trp Thr Tyr Ser
65              70              75              80
Leu Ser Thr Asn Gln His Ala Gln Ala Ser Ser Phe Gly Trp Arg Met
                85              90              95
Thr Thr Glu Met Lys Val Leu Ser Gly Gly Met Ile Thr Asn Tyr Tyr
            100             105             110
Ala Asn Gly Thr Gln Arg Val Leu Pro Ile Ile Ser Leu Asp Ser Ser
            115             120             125
Gly Asn Leu Val Val Glu Phe Glu Gly Gln Thr Gly Arg Thr Val Leu
        130             135             140
Ala Thr Gly Thr Ala Ala Thr Glu Tyr His Lys Phe Glu Leu Val Phe
145             150             155             160
Leu Pro Gly Ser Asn Pro Ser Ala Ser Phe Tyr Phe Asp Gly Lys Leu
                165             170             175
Ile Arg Asp Asn Ile Gln Pro Thr Ala Ser Lys Gln Asn Met Ile Val
            180             185             190
Trp Gly Asn Gly Ser Ser Asn Thr Asp Gly Val Ala Ala Tyr Arg Asp
            195             200             205
Ile Lys Phe Glu Ile Gln Gly Asp Val Ile Phe Arg Gly Pro Asp Arg
        210             215             220
Ile Pro Ser Ile Val Ala Ser Ser Val Thr Pro Gly Val Val Thr Ala
225             230             235             240
Phe Ala Glu Lys Arg Val Gly Gly Gly Asp Pro Gly Ala Leu Ser Asn
                245             250             255
```

-continued

```
Thr Asn Asp Ile Ile Thr Arg Thr Ser Arg Asp Gly Gly Ile Thr Trp
            260             265             270

Asp Thr Glu Leu Asn Leu Thr Glu Gln Ile Asn Val Ser Asp Glu Phe
            275             280             285

Asp Phe Ser Asp Pro Arg Pro Ile Tyr Asp Pro Ser Ser Asn Thr Val
            290             295             300

Leu Val Ser Tyr Ala Arg Trp Pro Thr Asp Ala Ala Gln Asn Gly Asp
305             310             315             320

Arg Ile Lys Pro Trp Met Pro Asn Gly Ile Phe Tyr Ser Val Tyr Asp
                325             330             335

Val Ala Ser Gly Asn Trp Gln Ala Pro Ile Asp Val Thr Asp Gln Val
            340             345             350

Lys Glu Arg Ser Phe Gln Ile Ala Gly Trp Gly Gly Ser Glu Leu Tyr
            355             360             365

Arg Arg Asn Thr Ser Leu Asn Ser Gln Gln Asp Trp Gln Ser Asn Ala
            370             375             380

Lys Ile Arg Ile Val Asp Gly Ala Ala Asn Gln Ile Gln Val Ala Asp
385             390             395             400

Gly Ser Arg Lys Tyr Val Val Thr Leu Ser Ile Asp Glu Ser Gly Gly
                405             410             415

Leu Val Ala Asn Leu Asn Gly Val Ser Ala Pro Ile Ile Leu Gln Ser
            420             425             430

Glu His Ala Lys Val His Ser Phe His Asp Tyr Glu Leu Gln Tyr Ser
            435             440             445

Ala Leu Asn His Thr Thr Thr Leu Phe Val Asp Gly Gln Gln Ile Thr
            450             455             460

Thr Trp Ala Gly Glu Val Ser Gln Glu Asn Asn Ile Gln Phe Gly Asn
465             470             475             480

Ala Asp Ala Gln Ile Asp Gly Arg Leu His Val Gln Lys Ile Val Leu
                485             490             495

Thr Gln Gln Gly His Asn Leu Val Glu Phe Asp Ala Phe Tyr Leu Ala
            500             505             510

Gln Gln Thr Pro Glu Val Glu Lys Asp Leu Glu Lys Leu Gly Trp Thr
            515             520             525

Lys Ile Lys Thr Gly Asn Thr Met Ser Leu Tyr Gly Asn Ala Ser Val
            530             535             540

Asn Pro Gly Pro Gly His Gly Ile Thr Leu Thr Arg Gln Gln Asn Ile
545             550             555             560

Ser Gly Ser Gln Asn Gly Arg Leu Ile Tyr Pro Ala Ile Val Leu Asp
                565             570             575

Arg Phe Phe Leu Asn Val Met Ser Ile Tyr Ser Asp Asp Gly Gly Ser
            580             585             590

Asn Trp Gln Thr Gly Ser Thr Leu Pro Ile Pro Phe Arg Trp Lys Ser
            595             600             605

Ser Ser Ile Leu Glu Thr Leu Glu Pro Ser Glu Ala Asp Met Val Glu
            610             615             620

Leu Gln Asn Gly Asp Leu Leu Leu Thr Ala Arg Leu Asp Phe Asn Gln
625             630             635             640

Ile Val Asn Gly Val Asn Tyr Ser Pro Arg Gln Gln Phe Leu Ser Lys
                645             650             655

Asp Gly Gly Ile Thr Trp Ser Leu Leu Glu Ala Asn Asn Ala Asn Val
                660             665             670

Phe Ser Asn Ile Ser Thr Gly Thr Val Asp Ala Ser Ile Thr Arg Phe
```

```
        675              680              685
```

Glu Gln Ser Asp Gly Ser His Phe Leu Leu Phe Thr Asn Pro Gln Gly
    690              695              700

Asn Pro Ala Gly Thr Asn Gly Arg Gln Asn Leu Gly Leu Trp Phe Ser
705              710              715              720

Phe Asp Glu Gly Val Thr Trp Lys Gly Pro Ile Gln Leu Val Asn Gly
                725              730              735

Ala Ser Ala Tyr Ser Asp Ile Tyr Gln Leu Asp Ser Glu Asn Ala Ile
            740              745              750

Val Ile Val Glu Thr Asp Asn Ser Asn Met Arg Ile Leu Arg Met Pro
            755              760              765

Ile Thr Leu Leu Lys Gln Lys Leu Thr Leu Ser Gln Asn
    770              775              780

<210> SEQ ID NO 25
<211> LENGTH: 191
<212> TYPE: PRT
<213> ORGANISM: Vibrio cholerae

<400> SEQUENCE: 25

Leu Phe Asp Tyr Asn Ala Thr Gly Asp Thr Glu Phe Asp Ser Pro Ala
1               5               10              15

Lys Gln Gly Trp Met Gln Asp Asn Thr Asn Asn Gly Ser Gly Val Leu
                20              25              30

Thr Asn Ala Asp Gly Met Pro Ala Trp Leu Val Gln Gly Ile Gly Gly
            35              40              45

Arg Ala Gln Trp Thr Tyr Ser Leu Ser Thr Asn Gln His Ala Gln Ala
    50              55              60

Ser Ser Phe Gly Trp Arg Met Thr Thr Glu Met Lys Val Leu Ser Gly
65              70              75              80

Gly Met Ile Thr Asn Tyr Tyr Ala Asn Gly Thr Gln Arg Val Leu Pro
                85              90              95

Ile Ile Ser Leu Asp Ser Ser Gly Asn Leu Val Val Glu Phe Glu Gly
                100             105             110

Gln Thr Gly Arg Thr Val Leu Ala Thr Gly Thr Ala Ala Thr Glu Tyr
            115             120             125

His Lys Phe Glu Leu Val Phe Leu Pro Gly Ser Asn Pro Ser Ala Ser
    130             135             140

Phe Tyr Phe Asp Gly Lys Leu Ile Arg Asp Asn Ile Gln Pro Thr Ala
145             150             155             160

Ser Lys Gln Asn Met Ile Val Trp Gly Asn Gly Ser Ser Asn Thr Asp
                165             170             175

Gly Val Ala Ala Tyr Arg Asp Ile Lys Phe Glu Ile Gln Gly Asp
            180             185             190

<210> SEQ ID NO 26
<211> LENGTH: 1035
<212> TYPE: PRT
<213> ORGANISM: Streptococcus pneumoniae

<400> SEQUENCE: 26

Met Ser Tyr Phe Arg Asn Arg Asp Ile Asp Ile Glu Arg Asn Ser Met
1               5               10              15

Asn Arg Ser Val Gln Glu Arg Lys Cys Arg Tyr Ser Ile Arg Lys Leu
                20              25              30

Ser Val Gly Ala Val Ser Met Ile Val Gly Ala Val Val Phe Gly Thr
```

-continued

```
              35                    40                    45

Ser Pro Val Leu Ala Gln Glu Gly Ala Ser Glu Gln Pro Leu Ala Asn
    50                    55                    60

Glu Thr Gln Leu Ser Gly Glu Ser Ser Thr Leu Thr Asp Thr Glu Lys
65                    70                    75                    80

Ser Gln Pro Ser Ser Glu Thr Glu Leu Ser Gly Asn Lys Gln Glu Gln
                  85                    90                    95

Glu Arg Lys Asp Lys Gln Glu Glu Lys Ile Pro Arg Asp Tyr Tyr Ala
              100                   105                   110

Arg Asp Leu Glu Asn Val Glu Thr Val Ile Glu Lys Glu Asp Val Glu
              115                   120                   125

Thr Asn Ala Ser Asn Gly Gln Arg Val Asp Leu Ser Ser Glu Leu Asp
              130                   135                   140

Lys Leu Lys Lys Leu Glu Asn Ala Thr Val His Met Glu Phe Lys Pro
145                   150                   155                   160

Asp Ala Lys Ala Pro Ala Phe Tyr Asn Leu Phe Ser Val Ser Ser Ala
                  165                   170                   175

Thr Lys Lys Asp Glu Tyr Phe Thr Met Ala Val Tyr Asn Asn Thr Ala
              180                   185                   190

Thr Leu Glu Gly Arg Gly Ser Asp Gly Lys Gln Phe Tyr Asn Asn Tyr
              195                   200                   205

Asn Asp Ala Pro Leu Lys Val Lys Pro Gly Gln Trp Asn Ser Val Thr
    210                   215                   220

Phe Thr Val Glu Lys Pro Thr Ala Glu Leu Pro Lys Gly Arg Val Arg
225                   230                   235                   240

Leu Tyr Val Asn Gly Val Leu Ser Arg Thr Ser Leu Arg Ser Gly Asn
                  245                   250                   255

Phe Ile Lys Asp Met Pro Asp Val Thr His Val Gln Ile Gly Ala Thr
              260                   265                   270

Lys Arg Ala Asn Asn Thr Val Trp Gly Ser Asn Leu Gln Ile Arg Asn
              275                   280                   285

Leu Thr Val Tyr Asn Arg Ala Leu Thr Pro Glu Glu Val Gln Lys Arg
    290                   295                   300

Ser Gln Leu Phe Lys Arg Ser Asp Leu Glu Lys Lys Leu Pro Glu Gly
305                   310                   315                   320

Ala Ala Leu Thr Glu Lys Thr Asp Ile Phe Glu Ser Gly Arg Asn Gly
              325                   330                   335

Lys Pro Asn Lys Asp Gly Ile Lys Ser Tyr Arg Ile Pro Ala Leu Leu
              340                   345                   350

Lys Thr Asp Lys Gly Thr Leu Ile Ala Gly Ala Asp Glu Arg Arg Leu
              355                   360                   365

His Ser Ser Asp Trp Gly Asp Ile Gly Met Val Ile Arg Arg Ser Glu
    370                   375                   380

Asp Asn Gly Lys Thr Trp Gly Asp Arg Val Thr Ile Thr Asn Leu Arg
385                   390                   395                   400

Asp Asn Pro Lys Ala Ser Asp Pro Ser Ile Gly Ser Pro Val Asn Ile
                  405                   410                   415

Asp Met Val Leu Val Gln Asp Pro Glu Thr Lys Arg Ile Phe Ser Ile
              420                   425                   430

Tyr Asp Met Phe Pro Glu Gly Lys Gly Ile Phe Gly Met Ser Ser Gln
              435                   440                   445

Lys Glu Glu Ala Tyr Lys Lys Ile Asp Gly Lys Thr Tyr Gln Ile Leu
    450                   455                   460
```

-continued

```
Tyr Arg Glu Gly Glu Lys Gly Ala Tyr Thr Ile Arg Glu Asn Gly Thr
465                 470                 475                 480

Val Tyr Thr Pro Asp Gly Lys Ala Thr Asp Tyr Arg Val Val Val Asp
                485                 490                 495

Pro Val Lys Pro Ala Tyr Ser Asp Lys Gly Asp Leu Tyr Lys Gly Asn
                500                 505                 510

Gln Leu Leu Gly Asn Ile Tyr Phe Thr Thr Asn Lys Thr Ser Pro Phe
                515                 520                 525

Arg Ile Ala Lys Asp Ser Tyr Leu Trp Met Ser Tyr Ser Asp Asp Asp
                530                 535                 540

Gly Lys Thr Trp Ser Ala Pro Gln Asp Ile Thr Pro Met Val Lys Ala
545                 550                 555                 560

Asp Trp Met Lys Phe Leu Gly Val Gly Pro Gly Thr Gly Ile Val Leu
                565                 570                 575

Arg Asn Gly Pro His Lys Gly Arg Ile Leu Ile Pro Val Tyr Thr Thr
                580                 585                 590

Asn Asn Val Ser His Leu Asn Gly Ser Gln Ser Ser Arg Ile Ile Tyr
                595                 600                 605

Ser Asp Asp His Gly Lys Thr Trp His Ala Gly Glu Ala Val Asn Asp
                610                 615                 620

Asn Arg Gln Val Asp Gly Gln Lys Ile His Ser Ser Thr Met Asn Asn
625                 630                 635                 640

Arg Arg Ala Gln Asn Thr Glu Ser Thr Val Val Gln Leu Asn Asn Gly
                645                 650                 655

Asp Val Lys Leu Phe Met Arg Gly Leu Thr Gly Asp Leu Gln Val Ala
                660                 665                 670

Thr Ser Lys Asp Gly Gly Val Thr Trp Glu Lys Asp Ile Lys Arg Tyr
                675                 680                 685

Pro Gln Val Lys Asp Val Tyr Val Gln Met Ser Ala Ile His Thr Met
                690                 695                 700

His Glu Gly Lys Glu Tyr Ile Ile Leu Ser Asn Ala Gly Gly Pro Lys
705                 710                 715                 720

Arg Glu Asn Gly Met Val His Leu Ala Arg Val Glu Glu Asn Gly Glu
                725                 730                 735

Leu Thr Trp Leu Lys His Asn Pro Ile Gln Lys Gly Glu Phe Ala Tyr
                740                 745                 750

Asn Ser Leu Gln Glu Leu Gly Asn Gly Glu Tyr Gly Ile Leu Tyr Glu
                755                 760                 765

His Thr Glu Lys Gly Gln Asn Ala Tyr Thr Leu Ser Phe Arg Lys Phe
                770                 775                 780

Asn Trp Asp Phe Leu Ser Lys Asp Leu Ile Ser Pro Thr Glu Ala Lys
785                 790                 795                 800

Val Lys Arg Thr Arg Glu Met Gly Lys Gly Val Ile Gly Leu Glu Phe
                805                 810                 815

Asp Ser Glu Val Leu Val Asn Lys Ala Pro Thr Leu Gln Leu Ala Asn
                820                 825                 830

Gly Lys Thr Ala Arg Phe Met Thr Gln Tyr Asp Thr Lys Thr Leu Leu
                835                 840                 845

Phe Thr Val Asp Ser Glu Asp Met Gly Gln Lys Val Thr Gly Leu Ala
                850                 855                 860

Glu Gly Ala Ile Glu Ser Met His Asn Leu Pro Val Ser Val Ala Gly
865                 870                 875                 880
```

-continued

```
Thr Lys Leu Ser Asn Gly Met Asn Gly Ser Glu Ala Ala Val His Glu
                885                 890                 895

Val Pro Glu Tyr Thr Gly Pro Leu Gly Thr Ser Gly Glu Glu Pro Ala
                900                 905                 910

Pro Thr Val Glu Lys Pro Glu Tyr Thr Gly Pro Leu Gly Thr Ser Gly
                915                 920                 925

Glu Glu Pro Ala Pro Thr Val Glu Lys Pro Glu Tyr Thr Gly Pro Leu
        930                 935                 940

Gly Thr Ala Gly Glu Glu Ala Ala Pro Thr Val Glu Lys Pro Glu Phe
945                 950                 955                 960

Thr Gly Gly Val Asn Gly Thr Glu Pro Ala Val His Glu Ile Ala Glu
                965                 970                 975

Tyr Lys Gly Ser Asp Ser Leu Val Thr Leu Thr Thr Lys Glu Asp Tyr
                980                 985                 990

Thr Tyr Lys Ala Pro Leu Ala Gln  Gln Ala Leu Pro Glu  Thr Gly Asn
                995                 1000                1005

Lys Glu  Ser Asp Leu Leu Ala  Ser Leu Gly Leu Thr  Ala Phe Phe
    1010                 1015                1020

Leu Gly  Leu Phe Thr Leu Gly  Lys Lys Arg Glu Gln
    1025                 1030                1035

<210> SEQ ID NO 27
<211> LENGTH: 185
<212> TYPE: PRT
<213> ORGANISM: Streptococcus pneumoniae

<400> SEQUENCE: 27

Val Ile Glu Lys Glu Asp Val Glu Thr Asn Ala Ser Asn Gly Gln Arg
1               5                   10                  15

Val Asp Leu Ser Ser Glu Leu Asp Lys Leu Lys Lys Leu Glu Asn Ala
                20                  25                  30

Thr Val His Met Glu Phe Lys Pro Asp Ala Lys Ala Pro Ala Phe Tyr
                35                  40                  45

Asn Leu Phe Ser Val Ser Ser Ala Thr Lys Lys Asp Glu Tyr Phe Thr
        50                  55                  60

Met Ala Val Tyr Asn Asn Thr Ala Thr Leu Glu Gly Arg Gly Ser Asp
65                  70                  75                  80

Gly Lys Gln Phe Tyr Asn Asn Tyr Asn Asp Ala Pro Leu Lys Val Lys
                85                  90                  95

Pro Gly Gln Trp Asn Ser Val Thr Phe Thr Val Glu Lys Pro Thr Ala
                100                 105                 110

Glu Leu Pro Lys Gly Arg Val Arg Leu Tyr Val Asn Gly Val Leu Ser
                115                 120                 125

Arg Thr Ser Leu Arg Ser Gly Asn Phe Ile Lys Asp Met Pro Asp Val
        130                 135                 140

Thr His Val Gln Ile Gly Ala Thr Lys Arg Ala Asn Asn Thr Val Trp
145                 150                 155                 160

Gly Ser Asn Leu Gln Ile Arg Asn Leu Thr Val Tyr Asn Arg Ala Leu
                165                 170                 175

Thr Pro Glu Glu Val Gln Lys Arg Ser
                180                 185
```

CBM USES

RELATED APPLICATIONS

This application is a 35 U.S.C. § 371 national stage of PCT Application No. PCT/GB2020/050170, filed on Jan. 24, 2020, which claims priority from United Kingdom Patent Application No. 1901057.8, filed on Jan. 25, 2019, the contents of which are incorporated herein by reference. The above-referenced PCT International Application was published in the English language as International Publication No. WO 2020/152479 A1 on Jul. 30, 2020.

STATEMENT REGARDING ELECTRONIC FILING OF A SEQUENCE LISTING

A Sequence Listing in ASCII text format, submitted under 37 C.F.R. § 1.821, entitled 9013-196_ST25.txt, 81,963 bytes in size, generated on Aug. 3, 2021 and filed via EFS-Web, is provided in lieu of a paper copy. This Sequence Listing is incorporated by reference into the specification for its disclosures.

FIELD OF THE INVENTION

The present invention provides uses, methods and compositions for the treatment of cancer.

BACKGROUND OF THE INVENTION

Some lectins, which are glycoproteins of non-immune origin, exhibit an ability to induce apoptosis in malignant cells and thus demonstrate anti-cancer properties. This phenomenon occurs, in part, through the interaction of these lectins with specific glycan receptors on immune cells (Yau et al., 2015).

One such lectin is Viscumin from mistletoe, which is a toxin that binds to cellular receptors that are glycosylated with α2,6 sialyllactose (Muthing et al., 2002). Viscumin is a 57 kDa heterodimer, comprising of two subunits A and B. The A subunit exerts its toxic effect by disabling ribosomes, thereby interrupting protein production, whereas the B subunit exhibits glycan binding function. The lectin demonstrates picomolar cytotoxicity in vitro and in vivo, and has a recommended dose upper limit of 6 µg/kg in clinical trial subjects (half-life of 13 mins) (Zwierzina et al., 2011).

Another plant lectin that has demonstrated an ability to prevent cell migration and growth (and hence an anti-cancer property) is the *Maackia amurensis* seed lectin, or MASL (Ochoa-Alvarez et al., 2012; Astarita et al., 2012). This lectin is also cytotoxic exhibiting nanomolar potency (~300 nM), and exerts its effects through the binding of podoplanin, an α2,3 sialylated mucin-type transmembrane glycoprotein, that is overexpressed in a variety of human cancers (Kato et al., 2005; Schacht et al., 2005; Shibahara et al., 2006).

WO2018/055373 describes the use of sialic acid binding molecules, including carbohydrate binding modules, in methods of modulating cell growth and in the treatment and/or prevention of cell proliferation and/or differentiation disorders.

The treatment of cell proliferation and differentiation disorders, including, for example cancer, demands the provision of additional molecules that are well tolerated in their hosts and have therapeutic potential.

SUMMARY OF THE INVENTION

The present disclosure is based on the finding that a class of sugar (carbohydrate)-binding proteins known as carbohydrate-binding modules (CBMs) may modulate aspects of cell growth and/or cell activity.

Accordingly, the disclosure provides various uses, including medical uses of molecules comprising the CBMs described herein.

CBMs are often found as part of a larger enzyme (for example, a carbohydrate-active enzyme such as a glycosidase) where their role is to bind a carbohydrate ligand and direct the catalytic domain of the enzyme towards its substrate.

The disclosure specifically concerns those CBMs which belong to the groups known as (i) carbohydrate binding module Family 32 (CBM32);
(ii) carbohydrate binding module Family 47 (CBM47)
(iii) carbohydrate binding module Family 67 (CBM67)
(iv) carbohydrate binding module Family 70 (CBM70)

In this regard, the disclosure relates to the finding that CBMs from all of the CBM families described above (CBM families (i)-(iv)) modulate aspects of cell growth and/or cell activity.

The terms "CBM32", "CBM47", "CBM67" and "CBM70" as used herein may refer to compounds, compositions or molecules which comprise one or more carbohydrate binding module(s) and which are classed as belonging to the carbohydrate binding module families 32, 47, 67 and/or 70. The term "CBM32" as used herein may embrace and/or encompass those carbohydrate binding modules designated as belonging to the CBM32 family in the Carbohydrate Active Enzymes database (freely accessible on the internet). Additionally, the terms "CBM47", "CBM67" and "CBM70" as used herein may embrace and/or encompass those carbohydrate binding modules designated as belonging to the CBM47, CBM67 and CBM70 families in the Carbohydrate Active Enzymes database (freely accessible on the internet).

The disclosure may embrace the use of molecules, for example, larger molecules, which comprise a CBM, for example, a CBM32, a CBM47, a CBM67 and a CBM70. By way of (non-limiting) example, the molecules of this disclosure may not only exhibit an ability to bind sialic acid but may also have one or more other functions. For example, the molecules may have enzymatic activity.

In some instances, the CBM for the various uses described herein, may not be provided as part of, or comprised within, a molecule (for example a fusion protein) with enzymatic (for example, sialidase) activity.

It should be noted that throughout this specification, the terms "comprise", "comprising" and/or "comprises" is/are used to denote that aspects and embodiments of this invention "comprise" a particular feature or features. It should be understood that this/these terms may also encompass aspects and/or embodiments which "consist essentially of" or "consist of" the relevant feature or features.

As such, within the context of this disclosure a "CBM32", "CBM47", "CBM67" and/or "CBM70" may comprise, consist essentially of or consist of, one or more molecules classed as belonging to the carbohydrate binding module families 32, 47, 67 and/or 70. The terms "CBM32", "CBM47", "CBM67" and/or "CBM70" may embrace fragments or portions of native, wild type or reference CBM32s, CBM47s, CBM67s and/or CBM70s—any such fragments or portions should be functional, that is to say, they retain the carbohydrate binding ability of a native, wild type or reference CBM32, CBM47, CBM67 and/or CBM70 from which they are derived.

Useful CBM32s may be derived from any suitable source. For example, CBM32s for use may be obtained from microorganisms, including, for example, bacteria of the genera *Cellvibrio, Yersinia, Micromonospora, Streptococcus, Bifidobacteria* and *Clostridium*. For example, useful CBM32s may be obtained or derived from, for example, *Cellvibrio mixtus, Yersinia enterolitica, Clostridium perfringens, Clostridium thermocellum, Streptococcus pneumoniae, Bifidobacterium longum* and *Micromonospora viridifaciens*. Further details concerning the source, structure and function of the CBM32 family can be found within the Carbohydrate Active Enzymes database (freely available on the internet).

An exemplary CBM32 sequence is provided by SEQ ID NO: 1 below:

```
                                        SEQ ID NO: 1
AIIETAIPQSEMTASATSEEGQDPASSAIDGNTNTMW

HTKWNGSDALPQSLSVNLGSSRKVSSIAITPRTSGNN

GFITKYEIHAINNGVETLVAEGTWEENNLVKTVTFDS

PIDAEEIKITAIQGVGGFASIAELNVYE
```

Accordingly, a CBM for use may comprise, consist essentially or consist of a CBM having the sequence of SEQ ID NO: 1 or a carbohydrate binding portion thereof.

A carbohydrate binding fragment of SEQ ID NO: 1 may comprise anywhere between about 5, 6, 7, 8, 9 or 10 (consecutive or contiguous) amino acids to about 138 (consecutive or contiguous) amino acids from SEQ ID NO: 1. Suitable fragments may comprise about 11, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130 or about 135 (consecutive or contiguous) amino acids from SEQ ID NO: 1.

CBM32 or a protein comprising, consisting essentially or consisting of SEQ ID NO: 1 may bind, for example, galactose, N-acetylgalactosamine (GalNAc), N-acetylglucosamine (GlcNAc) and/or lactose. Accordingly, any fragment for use may also bind galactose, N-acetylgalactosamine (GalNAc), N-acetylglucosamine (GlcNAc) and/or lactose. One of skill will appreciate that the binding affinity of any given CBM32 molecule may depend on the precise CBM32 subtype; by way of further examples, some CBM32s have shown affinity for a variety of ligands (examples include type II blood group H-trisaccharide (Fucal-2Galb1-4GlcNAc), N-acetyl-D-lactosamine (LacNAc), galactose, lacto-N-biose, disaccharide GlcNAc-α-1,4-Gal (which may be referred to as an N-acetylglucosamine linked alpha 1,4 to galactose), and/or GlcNAc). It should also be noted that multiple CBM32 subtypes may be derived from a single organism; these different CBM subtypes may exhibit the same, similar or different binding specificities. For example, *Clostridium perfringens* contains two sialidases NanJ and NanH; NanJ contains one galactose-specific CBM32; NanH contains four putative CBM32s with different binding selectivity—for example, the CBM32 encoded by NanH binds GlcNAc. As used herein, the term CBM32 embraces all CBM32 variants, derivatives and sub-types.

SEQ ID NO: 1 is derived from the sequence deposited in the UniProt database under ID No: A0A2X2YJF2. This sequence is reproduced as SEQ ID NO: 2 below (SEQ ID NO: 1 appears as residues 42-180—shown in bold in the sequence below):

```
                                        SEQ ID NO: 2
MKSKKIIATL VASLVISNMG GYLVKANPNV

NHKAVIIEDR QAIIETAIPQ SEMTASATSE

EGQDPASSAI DGNTNTMWHT KWNGSDALPQ

SLSVNLGSSR KVSSIAITPR TSGNNGFITK

YEIHAINNGV ETLVAEGTWE ENNLVKTVTF

DSPIDAEEIK ITAIQGVGGF ASIAELNVYE

IKGEVDEIAN YGNLKITKEE ERLNITRDLE

KFSSLDEGTI VTRFNMNDTS IQSLIGLSDG

NKANNYFSLY VSGGKVGYEL RRQEGNGDFN

VHHSADVTFN KGINTLALKI EKGVGAKIFL

NGSLVKTVSD PNIKFLNAIN LNSGFIGKTD

RANGYNEYLF RGNIDFMNIY DKPVSDNYLL

RKTGETKAPS EDSLLPDDVY KTQPVELFYP

GYLESRGYRI PALETTKKGT VLASIDVRNN

GDHDAPNNNI DVGIRRKEVN GEWEEGKVIL

DYPGKSAAID TSLMSATIEE NGIEKERIFL

IVTHFPEGYG FPNTEGGSGY KEIDGKYYFI

LKDAQNNEYT VREDGIVYNS EGNETDYVMK

NDKTLIQNGE EVGNALLSNS PLKAVGTAHI

EMIYSDDDGN TWSEPEDLNP GLKKEWMKFF

GTAPGKGIQI KNGEHKGRLV FPIYYTNQNN

FQSSAVIYSD DFGETWKLGE SPIDTASVSS

ETVSSGTQLT ECQVVEMPNG QLKLFMRNTG

SYTRIATSFD GGATWHDEVP EDTSLREPYC

QLSVINYSGK INGKDAIIFS NPDASSRVNG

SVKVGLINEN GTYENGQPRY EFDWIYNKTV

KPGSFAYSCL TELPDGNLGL FYEGEGAGRM

AYTEFDLNYL KFNASEDSPA ATVQSIESLD

EDLIYNAGDE VSIKVNFNQL VSLIGDRKIT

LDIGGVDVPL NMVNYEGKSS AIFKGTIPEG

INPGNYEIKL KENNALELNT VYNKVSTLNG

LDNTGINVQI GELKTTVGNS TIKVNEEVQV

GSAFEAILGI KGLNGDTEVY SAEYLFEYNA

EAFKLNEITS FSDSLFVKSK EVEPGKVRIL

VASLGNEIEK DSELVKVNLT PKISSELEVL

GLTTALVGAG DGNTHDLELS SKEVKINEEA

SGEIVVNPVQ NFEIPEINKK NVKLTWNAPI

TTEGLEGYVI YKDGKKLSEV PAESTEFVVS

KLNRHTIYNF KVAAKYSNGE LSAKESKTIR

TAR
```

SEQ ID NOS 1 and 2 are derived from *Clostridium perfringens*.

A CBM for use in the various aspects of this disclosure may comprise one, two, three, four or more CBM32s.

A CBM for use may comprise one, two, three, four or more proteins comprising SEQ ID NO: 1 or a carbohydrate binding fragment thereof.

One of skill will appreciate that useful CBM32s may comprise sequences which exhibit some degree (for example, 99%, 95%, 90%, 85%, 80%, 75%, 70%, 65% or 60%) of sequence identity or homology with the CBM32 sequences of SEQ ID NOS: 1 and 2. All such variant or divergent sequences are to be embraced within the scope of this disclosure and by the term "CBM32". Identical and/or homologous CBM32 sequences may have carbohydrate binding function.

CBM47s may be derived from any suitable source. For example, CBM47s for use may be obtained from microorganisms, including, for example, bacteria of the genera *Acinetobacter, Bathymodiolus, Campylobacter, Planctomycetes, Streptococcus* and *Streptomyces*. For example, useful CBM47s may be obtained or derived from, for example, *Streptococcus mitis* or *Streptococcus pneumoniae*. Further details concerning potential sources and the structure and function of the CBM47 family can be found within the Carbohydrate Active Enzymes database (freely available on the internet).

An exemplary CBM47 sequence is provided by SEQ ID NO: 3 below:

```
                              SEQ ID NO: 3
TPDKFNDGNLNIAYAKPTTQSSVDYNGDPNRAVDGNR

NGNFNSGSVTHTRADNPSWWEVDLKKMDKVGLVKIYN

RTDAETQRLSNFDVILYDNNRNEVAKKHVNNLSGESV

SLDFKEKGARYIKVKLLTSGVPLSLAEVEVFRES
```

Accordingly, a CBM for use may comprise, consist essentially or consist of a CBM having the sequence of SEQ ID NO: 3 or a carbohydrate binding portion thereof.

A carbohydrate binding fragment of SEQ ID NO: 3 may comprise anywhere between about 5, 6, 7, 8, 9 or 10 (consecutive or contiguous) amino acids to about 144 (consecutive or contiguous) amino acids from SEQ ID NO: 3. Suitable fragments may comprise about 11, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130 or about 135, about 140 or about 143 (consecutive or contiguous) amino acids from SEQ ID NO: 3.

CBM47 or a protein comprising, consisting essentially or consisting of SEQ ID NO: 3 may bind L-fucose, fucosyl-lactose, H-trisaccharide and/or Lewis$^y$ antigen. Accordingly, any fragment for use may also bind L-fucose, fucosyllactose, H-trisaccharide and/or Lewis$^y$ antigen.

SEQ ID NO: 3 is derived from the sequence deposited in the UniProt database under ID No: A0A1Q2T229. This sequence is reproduced as SEQ ID NO: 4 below (SEQ ID NO: 3 appears as residues 601-745—shown in bold in the sequence below):

```
                              SEQ ID NO: 4
MNKEKIKRKL ITILFVCIGM LCFGLLAGVK

ADNRVQMRTT INNESPLLLS PLYGNDNGNG
```

```
LWWGNTLKGA WEAIPEDVKP YAAIELHPAK

VCKPTSCIPR DTKELREWYV KMLEEAQSLN

IPVFLVIMSA GERNTVPPEW LDEQFQKYSV

LKGVLNIENY WIYNNQLAPH SAKYLEVCAK

YGAHFIWHDH EKWFWETIMN DPTFFEASQK

YHKNLVLATK NTPIRDDAGT DSIVSGFWLS

GLCDNWGSST DTWKWWEKHY TNTFETGRAR

DMRSYASEPE SMIAMEMMNV YTGGGTVYNF

ECAAYTFMTN DVPTPAFTKG IIPFFRHAIQ

NPAPSKEEVV NRTKAVFWNG EGRISSLNGF

YQGLYSNDET MPLYNNGRYH ILPVIHEKID

KEKISSIFPN AKILTKNSEE LSSKVNYLNS

LYPKLYEGDG YAQRVGNSWY IYNSNANINK

NQQVMLPMYT NNTKSLSLDL TPHTYAVVKE

NPNNLHILLN NYRTDKTAMW ALSGNFDASK

SWKKEELELA NWISKNYSIN PVDNDFRTTT

LTLKGHTGHK PQINISGDKN HYTYTENWDE

NTHVYTITVN HNGMVEMSIN TEGTGPVSFP

TPDKFNDGNL NIAYAKPTTQ SSVDYNGDPN

RAVDGNRNGN FNSGSVTHTR ADNPSWWEVD

LKKMDKVGLV KIYNRTDAET QRLSNFDVIL

YDNNRNEVAK KHVNNLSGES VSLDFKEKGA

RYIKVKLLTS GVPLSLAEVE VFRESDGKQS

EEDIDKITED KVVSTNKVAT QSSTNYEGVA

ALAVDGNKDG DYGHHSVTHT KEDSPSWWEI

DLAQTEELEK LIIYNRTDAE IQRLSNFDII

IYDSNDYEVF TQHIDSLESN NLSIDLKGLK

GKKVRISLRN AGIPLSLAEV EVYTYK
```

SEQ ID NOS 3 and 4 are derived from *Streptococcus pneumoniae*.

A CBM for use in the various aspects of this disclosure may comprise one, two, three, four or more CBM47s.

A CBM for use may comprise one, two, three, four or more proteins comprising SEQ ID NO: 3 or a carbohydrate binding fragment thereof.

One of skill will appreciate that useful CBM47s may comprise sequences which exhibit some degree (for example, 99%, 95%, 90%, 85%, 80%, 75%, 70%, 65% or 60%) of sequence identity or homology with the CBM47 Sequences of SEQ ID NOS: 3 and 4. All such variant or divergent sequences are to be embraced within the scope of this disclosure and by the term "CBM47". Identical and/or homologous CBM47 sequences may have carbohydrate binding function.

CBM67s may be derived from any suitable source. For example, CBM67s for use may be obtained from microorganisms, including, for example, bacteria of the genera *Bacillus, Paenibacillus, Planctomycetes* and *Streptomyces*. For example, a useful CBM67s may be obtained or derived from, for example, *Streptomyces avermitilis*. Further details concerning potential sources and the structure and function of the CBM67 family can be found within the Carbohydrate Active Enzymes database (freely available on the internet).

An exemplary CBM67 sequence is provided by SEQ ID NO: 5 below:

```
                                  SEQ ID NO: 5
APSLEGSSWIWFPEGEPANSAPAATRWFRRTVDLPD

DITGATLAISADNVYAVSVDGAEVARTDLEADNEGW

RRPAVIDVLDHVHSGNNTLAVSASNASVGPAGWICV

LVLTTASGEKKIFSDASWKSTDHEPADGWREPDFDD

SGWPAAKVAAAWGAGPWGRVA
```

Accordingly, a CBM for use may comprise, consist essentially or consist of a CBM having the sequence of SEQ ID NO: 5 or a carbohydrate binding portion thereof.

A carbohydrate binding fragment of SEQ ID NO: 5 may comprise anywhere between about 5, 6, 7, 8, 9 or 10 (consecutive or contiguous) amino acids to about 164 (consecutive or contiguous) amino acids from SEQ ID NO: 5. Suitable fragments may comprise about 11, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135 about 140, about 145, about 150, about 155, about 160 or about 163 (consecutive or contiguous) amino acids from SEQ ID NO: 5.

CBM67 or a protein comprising, consisting essentially or consisting of SEQ ID NO: 5 may bind L-rhamnose. Accordingly, any fragment for use may also bind L-rhamnose.

SEQ ID NO: 5 is derived from the sequence deposited in the UniProt database under ID No: Q82PP4. This sequence is reproduced as SEQ ID NO: 6 below (SEQ ID NO: 5 appears as residues 132-296—shown in bold in the sequence below):

```
                                  SEQ ID NO: 6
MSALRVTSPS VEYVQRPLGL DAAHPRLSWP

MASAAPGRRQ SAYQVRVASS AAGLSHPDVW

DSGKVVSDDS VLVPYAGPPL KPRTRYFWSV

RVWDADGGAS EWSAPSWWET GLMGASQWSA

KWISAPAPLT EAPSLEGSSW IWFPEGEPAN

SAPAATRWFR RTVDLPDDIT GATLAISADN

VYAVSVDGAE VARTDLEADN EGWRRPAVID

VLDHVHSGNN TLAVSASNAS VGPAGWICVL

VLTTASGEKK IFSDASWKST DHEPADGWRE

PDFDDSGWPA AKVAAAWGAG PWGRVAPVAS

AANQLRHEFR LPHKKVSRAR LYATALGLYE

AHLNGRRVGR DQLAPGWTDY RKRVQYQTYD

VTSSVRPGAN ALAAYVAPGW YAGNVGMFGP
```

-continued
```
HQYGERPALL AQLEVEYADG TSERITSGPD

WRAASGPIVS ADLLSGETYD ARKETAGWTS

PGFDDRAWLA VRGADNDVPE QIVAQVDGPV

RIAKELPARK VTEPKPGVFV LDLGQNMVGS

VRLRVSGDAG TTVRLRHAEV LNPDGTIYTA

NLRSAAATDT YTLKGQGEET YEPRFTFHGF

RYVEVTGFPG KPSTTSVTGR VMHTSAPFTF

EFETNVPMLN KLHSNITWGQ RGNFLSVPTD

TPARDERLGW TGDINVFAPT AAYTMESARF

LTKWLVDLRD AQTSDGAFTD VAPAVGNLGN

GVAGWGDAGV TVPWALYQAY GDRQVLADAL

PSVHAWLRYL EKHSDGLLRP ADGYGDWLNV

SDETPKDVIA TAYFAHSADL AARMATELGK

DAAPYTDLFT RIRKAFQTAY VASDGKVKGD

TQSAYVLTLS MNLVPDALRK AAADRLVALI

EAKDWHLSTG FLGTPRLLPV LTDTGHTDVA

YRLLHQRTFP SWGYPIDKGS TTMWERWDSI

QPDGGFQTPE MNSFNHYAYG SVGEWMYANI

AGIAPGRAGY RQVVIRPRPG GEVTSARATF

ASLHGPVSTR WQQRSGGFVL TCSVPPNTTA

EVWIPADHPD RVQHTHGTFV RAEDGCAVFE

VGSGSHRFTV
```

SEQ ID NOS 5 and 6 are derived from *Streptomyces avermitilis*.

A CBM for use in the various aspects of this disclosure may comprise one, two, three, four or more CBM67s.

A CBM for use may comprise one, two, three, four or more proteins comprising SEQ ID NO: 5 or a carbohydrate binding fragment thereof.

One of skill will appreciate that useful CBM67s may comprise sequences which exhibit some degree (for example 99%, 95%, 90%, 85%, 80%, 75%, 70%, 65% or 60%) of sequence identity or homology with the CBM67 Sequences of SEQ ID NOS: 5 and 6. All such variant or divergent sequences are to be embraced within the scope of this disclosure and by the term "CBM67". Identical and/or homologous CBM67 sequences may have carbohydrate binding function.

CBM70s may be derived from any suitable source. For example, CBM70s for use may be obtained from microorganisms, including, for example, bacteria of the genera *Bacillus, Paenibacillus, Planctomycetes* and *Streptococcus*. For example, a useful CBM70s may be obtained or derived from, for example, *Streptomyces pneumoniae*. Further details concerning potential sources and the structure and function of the CBM70 family can be found within the Carbohydrate Active Enzymes database (freely available on the internet).

An exemplary CBM70 sequence is provided by SEQ ID NO: 7 below:

```
                                  SEQ ID NO: 7
NLVENGDFGQTEDGSSPWTGSKAQGWSAWVDQKNSA

DASTRVIEAKDGAITISSHEKLRAALHRMVPIEAKK

KYKLRFKIKTDNKIGIAKVRIIEESGKDKRLWNSAT

TSGTKDWQTIEADYSPTLDVDKIKLELFYETGTGTV

SFKDIELVEVADQLS
```

Accordingly, a CBM for use may comprise, consist essentially or consist of a CBM having the sequence of SEQ ID NO: 7 or a carbohydrate binding portion thereof.

A carbohydrate binding fragment of SEQ ID NO: 7 may comprise anywhere between about 5, 6, 7, 8, 9 or 10 (consecutive or contiguous) amino acids to about 158 (consecutive or contiguous) amino acids from SEQ ID NO: 7. Suitable fragments may comprise about 11, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155 or about 157 (consecutive or contiguous) amino acids from SEQ ID NO: 7.

CBM70 or a protein comprising, consisting essentially or consisting of SEQ ID NO: 7 may bind hyaluronan. Accordingly, any fragment for use may also bind hyaluronan.

SEQ ID NO: 7 is derived from the sequence deposited in the UniProt database under ID No: Q54873. This sequence is reproduced as SEQ ID NO: 8 below (SEQ ID NO: 7 appears as residues 54-212—shown in bold in the sequence below):

```
                                  SEQ ID NO: 8
MQTKTKKLIV  SLSSLVLSGF  LLNHYMTIGA

EETTTNTIQQ  SQKEVQYQQR  DTKNLVENGD

FGQTEDGSSP  WTGSKAQGWS  AWVDQKNSAD

ASTRVIEAKD  GAITISSHEK  LRAALHRMVP

IEAKKKYKLR  FKIKTDNKIG  IAKVRIIEES

GKDKRLWNSA  TTSGTKDWQT  IEADYSPTLD

VDKIKLELFY  ETGTGTVSFK  DIELVEVADQ

LSEDSQTDKQ  LEEKIDLPIG  KKHVFSLADY

TYKVENPDVA  SVKNGILEPL  KEGTTNVIVS

KDGKEVKKIP  LKILASVKDA  YTDRLDDWNG

IIAGNQYYDS  KNEQMAKLNQ  ELEGKVADSL

SSISSQADRT  YLWEKFSNYK  TSANLTATYR

KLEEMAKQVT  NPSSRYYQDE  TVVRTVRDSM

EWMHKHVYNS  EKSIVGNWWD  YEIGTPRAIN

NTLSLMKEYF  SDEEIKKYTD  VIEKFVPDPE

HFRKTTDNPF  KALGGNLVDM  GRVKVIAGLL

RKDDQEISST  IRSIEQVFKL  VDQGEGFYQD

GSYIDHTNVA  YTGAYGNVLI  DGLSQLLPVI

QKTKNPIDKD  KMQTMYHWID  KSFAPLLVNG
```

```
-continued
ELMDMSRGRS  ISRANSEGHV  AAVEVLRGIH

RIADMSEGET  KQCLQSLVKT  IVQSDSYYDV

FKNLKTYKDI  SLMQSLLSDA  GVASVPRPSY

LSAFNKMDKT  AMYNAEKGFG  FGLSLFSSRT

LNYEHMNKEN  KRGWYTSDGM  FYLYNGDLSH

YSDGYWPTVN  PYKMPGTTET  DAKRADSDTG

KVLPSAFVGT  SKLDDANATA  TMDFTNWNQT

LTAHKSWFML  KDKIAFLGSN  IQNTSTDTAA

TTIDQRKLES  GNPYKVYVND  KEASLTEQEK

DYPETQSVFL  ESFDSKKNIG  YFFFKKSSIS

MSKALQKGAW  KDINEGQSDK  EVENEFLTIS

QAHKQNRDSY  GYMLIPNVDR  ATFNQMIKEL

ESSLIENNET  LQSVYDAKQG  VWGIVKYDDS

VSTISNQFQV  LKRGVYTIRK  EGDEYKIAYY

NPETQESAPD  QEVFKKLEQA  AQPQVQNSKE

KEKSEEEKNH  SDQKNLPQTG  EGQSILASLG

FLLLGAFYLF  RRGKNN
```

SEQ ID NOS 7 and 8 are derived from *Streptococcus pneumoniae*.

A CBM for use in the various aspects of this disclosure may comprise one, two, three, four or more CBM70s.

A CBM for use may comprise one, two, three, four or more proteins comprising SEQ ID NO: 7 or a carbohydrate binding fragment thereof.

One of skill will appreciate that useful CBM70s may comprise sequences which exhibit some degree (for example 99%, 95%, 90%, 85%, 80%, 75%, 70%, 65% or 60%) of sequence identity or homology with the CBM70 Sequences of SEQ ID NOS: 7 and 8. All such variant or divergent sequences are to be embraced within the scope of this disclosure and by the term "CBM70". Identical and/or homologous CBM70 sequences may have carbohydrate binding function.

To summarise, a molecule for use in the various aspects and embodiments of this disclosure may comprise one or more CBM(s), for example, one or more CBM32(s), one or more CBM47(s), one or more CBM67(s) and/or one or more CBM70(s).

Molecules for use may comprise a single CBM selected from the group consisting of:

a single CBM32;

a single CBM47;

a single CBM67; and a single CBM70.

Molecules for use may comprise a single CBM selected from the group consisting of:

a single CpCBM32;

a single SpCBM47;

a single SaCBM67; and a single SpCBM70.

Where "Cp" means *Clostridium perfringens*—thus "CpCBM32" denotes that the CBM32 moiety is derived from *Clostridium perfringens*; "Sp" means *Streptococcus pneumoniae*—thus "SpCBM47" and "SpCBM70" denotes that the CBM47 and/or CBM70 moieties are derived from

*Streptococcus pneumoniae*; and "SaCBM67" denotes that the CBM67 moiety is derived from *Streptomyces avermitilis*.

A CBM for use may comprise a plurality or multiple (i.e. two or more) CBMs. Molecules which comprise a plurality of CBMs may be termed "multivalent CBMs". A multivalent CBM may, for example, comprise two or more CpCBMs, two or more SpCBMs, two or more SaCBMs as described above. A multivalent CBM may comprise a mixture of different CBMs, for example one or more CpCBM(s) with one or more Sp/SaCBM(s).

Multivalent CBM molecules, (for example, a molecule comprising two or more CpCBM32 moieties) may be prepared as constructs comprising multiple CBMs linked by amino acid/peptide linkers. Each CBM may be linked to another by, for example, peptides comprising 5, 10 or 15 amino acids. By way of example, any one or more of the following peptides may be used to link two or more CBMs to produce a multivalent CBM:

```
(i) 5 amino acid linkers:
                          (SEQ ID NO: 9)
ALNGS (SEQ ID NO: 10)
LQALG (SEQ ID NO: 11)
GGNSG (SEQ ID NO: 12)
GGGSG (SEQ ID NO: 13)
GGSLG (SEQ ID NO: 14)
GGGSA (ii) 10 amino acid linkers:
                          (SEQ ID NO: 15)
ALNGSGGGSG (SEQ ID NO: 16)
LQALGGGGSL (iii)
15 amino acid linkers:
                          (SEQ ID NO: 17)
ALNGSGGGSGGGGSG
```

Thus, the various aspects and embodiments of this disclosure (uses, CBMs for use, methods and medicaments) may exploit molecules which comprise, consist of or consist essentially of CBMs selected from the group consisting of:

(i) one or more CpCBM32(s);
(ii) one or more SpCBM47(s);
(iii) one or more SaCBM67(s); and
(iv) one or more SpCBM70(s).

The molecules for use may further comprise an oligomerisation domain. Suitable oligomerisation domains may exhibit an ability to self-associate to form multimer structures, for example, trimers. An oligomerisation domain for use may comprise any molecule with the above-mentioned oligomerisation properties or any functional fragment thereof. For example, one or more (for example two) CBM molecules may be bound, coupled or fused to an oligomerisation domain—the resulting CBM molecule::oligomerisation domain "fusion" may then be used (with one or more other such "fusions") as a molecule for modulating cell growth and/or activity and/or for treating or preventing any of the diseases and/or conditions disclosed herein.

Suitable oligomerisation domains may be derived from, for example, *Pseudomonas aeruginosa* pseudaminidase. An exemplary *Pseudomonas aeruginosa* pseudaminidase sequence amino acid sequence has been deposited under accession number PA0579 and is reproduced below as SEQ ID NO: 18 (438 amino acids).

```
MNTYFDIPHR  LVGKALYESY  YDHFGQMDIL

SDGSLYLIYR  RATEHVGGSD  GRVVFSKLEG

GIWSAPTIVA  QAGGQDFRDV  AGGTMPSGRI

VAASTVYETG  EVKVYVSDDS  GVTWVHKFTL

ARGGADYNFA  HGKSFQVGAR  YVIPLYAATG

VNYELKWLES  SDGGETWGEG  STIYSGNTPY

NETSYLPVGD  GVILAVARVG  SGAGGALRQF

ISLDDGGTWT  DQGNVTAQNG  DSTDILVAPS

LSYIYSEGGT  PHVVLLYTNR  TTHFCYYRTI

LLAKAVAGSS  GWTERVPVYS  APAASGYTSQ

VVLGGRRILG  NLFRETSSTT  SGAYQFEVYL

GGVPDFESDW  FSVSSNSLYT  LSHGLQRSPR

RVVVEFARSS  SPSTWNIVMP  SYFNDGGHKG

SGAQVEVGSL  NIRLGTGAAV  WGTGYFGGID

NSATTRFATG  YYRVRAWI
```

The oligomerisation domain of SEQ ID NO: 18 is from amino acid residue 333 to 438 (grey highlight)—this sequence may be SEQ ID NO: 19.

Thus an oligomerisation domain for use may comprise from about residue 250, 275, 300, 310, 320, 333, 340 to 350 (i.e. from about residue 250 to about residue 350 including from about any residue therebetween) to about residue 400, 410, 420, 430 or 438 (i.e. to about any residue from about residue 400 residue 438 including to about any residue therebetween) of the *P. aeruginosa* pseudaminidase trimerisation domain (PaTD) provided by SEQ ID NO: 18. For example, a useful molecule may exploit an oligomerisation domain comprising residues 333 to 438 of SEQ ID NO: 18.

Further molecules for use in the various aspects and embodiments of this disclosure are described below.

One molecule for use is designated "Cp2CBM32TD"—this construct comprises a Cp2CBM32 unit which itself comprises 2 CBM32 molecules (shown in bold) derived from *Clostridium perfringens*, where the 2 copies of CBM32 are linked in tandem by a short peptide linker molecule (dashed underlined). The construct further comprises a trimerisation domain (TD: underlined) which is itself fused to one of the two CBM32s via another short linker moiety (bold underlined). The sequence of an exemplary Cp2CBM32TD is provided below as SEQ ID NO: 20.

```
                                 SEQ ID NO: 20
GAMAIIETAIPQSEMTASATSEEGQDPASSAIDG

NTNTMWHTKWNGSDALPQSLSVNLGSSRKVSSIA

ITPRTSGNNGFITKYEIHAINNGVETLVAEGTWE

ENNLVKTVTFDSPIDAEEIKITAIQGVGGFASIA
```

```
-continued
ELNVYEGGGSGAIIETAIPQSEMTASATSEEGQD

PASSAIDGNTNTMWHTKWNGSDALPQSLSVNLGS

SRKVSSIAITPRTSGNNGFITKYEIHAINNGVET

LVAEGTWEENNLVKTVTFDSPIDAEEIKITAIQG

VGGFASIAELNVYEGGSLGVPDFESDWFSVSSNS

LYTLSHGLQRSPRRVVVEFARSSSPSTWNIVMPS

YFNDGGHKGSGAQVEVGSLNIRLGTGAAVWGTGY

FGGIDNSATTRFATGYYRVRAWI
```

One molecule for use is designated "Sp2CBM47TD"—this construct a Sp2CBM47 unit which itself comprises 2 CBM47 molecules (shown in bold) derived from *Streptococcus pneumoniae*, where the 2 copies of CBM47 are linked in tandem by a short peptide linker molecule (dashed underlined). The construct further comprises a trimerisation domain (TD: underlined) which is itself fused to one of the two CBM47s via another short linker moiety (bold underlined). The sequence of an exemplary Sp2CBM47TD is provided below as SEQ ID NO: 21.

```
                                   SEQ ID NO: 21
GAMGTPDKFNDGNLNIAYAKPTTQSSVDYNGDPN

RAVDGNRNGNFNSGSVTHTRADNPSWWEVDLKKM

DKVGLVKIYNRTDAETQRLSNFDVILYDNNRNEV

AKKHVNNLSGESVSLDFKEKGARYIKVKLLTSGV

PLSLAEVEVFRESGGSLGTPDKFNDGNLNIAYAK

PTTQSSVDYNGDPNRAVDGNRNGNFNSGSVTHTR

ADNPSWWEVDLKKMDKVGLVKIYNRTDAETQRLS

NFDVILYDNNRNEVAKKHVNNLSGESVSLDFKEK

GARYIKVKLLTSGVPLSLAEVEVFRESGGSLGVP

DFESDWFSVSSNSLYTLSHGLQRSPRRVVVEFAR

SSSPSTWNIVMPSYFNDGGHKGSGAQVEVGSLNI

RLGTGAAVWGTGYFGGIDNSATTRFATGYYRVRA

WI
```

One molecule for use is designated "Sa2CBM67TD"—this construct comprises a Sa2CBM67 unit which itself comprises 2 CBM67 molecules (grey highlight) derived from *Streptococcus avermitilis*, where the 2 copies of CBM67 are linked in tandem by a short peptide linker molecule (dashed underlined). The construct further comprises a trimerisation domain (TD: underlined) which is itself fused to one of the two CBM67s via another short linker moiety (bold underlined). The sequence of an exemplary Sa2CBM67TD is provided below as SEQ ID NO: 22.

```
                                   SEQ ID NO: 22
GAMAPSLEGSSWIWFPEGEPANSAPAATRWFRRT

VDLPDDITGATLAISADNVYAVSVDGAEVARTDL

EADNEGWRRPAVIDVLDHVHSGNNTLAVSASNAS

VGPAGWICVLVLTTASGEKKIFSDASWKSTDHEP
```

```
-continued
ADGWREPDFDDSGWPAAKVAAAWGAGPWGRVA

GGGSGAPSLEGSSWIWFPEGEPANSAPAATRWF

RRTVDLPDDITGATLAISADNVYAVSVDGAEVAR

TDLEADNEGWRRPAVIDVLDHVHSGNNTLAVSAS

NASVGPAGWICVLVLTTASGEKKIFSDASWKSTD

HEPADGWREPDFDDSGWPAAKVAAAWGAGPWGRV

AGGSLGVPDFESDWFSVSSNSLYTLSHGLQRSPR

RVVVEFARSSSPSTWNIVMPSYFNDGGHKGSGAQ

VEVGSLNIRLGTGAAVWGTGYFGGIDNSATTRFA

TGYYRVRAWI
```

One molecule for use is designated "Sp2CBM70TD"—this construct comprises a Sp2CBM70 unit which itself comprises 2 CBM70 molecules (shown in bold) derived from *Streptococcus pneumoniae*, where the 2 copies of CBM70 are linked in tandem by a short peptide linker molecule (dashed underlined). The construct further comprises a trimerisation domain (TD: underlined) which is itself fused to one of the two CBM70s via another short linker moiety (bold underlined). The sequence of an exemplary Sp2CBM70TD is provided below as SEQ ID NO: 23.

```
                                   SEQ ID NO: 23
GAMENLVENGDFGQTEDGSSPWTGSKAQGWSAWV

DQKNSADASTRVIEAKDGAITISSHEKLRAALHR

MVPIEAKKKYKLRFKIKTDNKIGIAKVRIIEESG

KDKRLWNSATTSGTKDWQTIEADYSPTLDVDKIK

LELFYETGTGTVSFKDIELVEVADQLSGGGSGNL

VENGDFGQTEDGSSPWTGSKAQGWSAWVDQKNSA

DASTRVIEAKDGAITISSHEKLRAALHRMVPIEA

KKKYKLRFKIKTDNKIGIAKVRIIEESGKDKRLW

NSATTSGTKDWQTIEADYSPTLDVDKIKLELFYE

TGTGTVSFKDIELVEVADQLSGGSLGVPDFESDW

FSVSSNSLYTLSHGLQRSPRRVVVEFARSSSPST

WNIVMPSYFNDGGHKGSGAQVEVGSLNIRLGTGA

AVWGTGYFGGIDNSATTRFATGYYRVRAWI
```

In a first aspect, the various molecules disclosed herein may be for use in therapy. Further, the various molecules disclosed herein may be for use as medicaments. In the context of this aspect, the reader should understand that the "molecules disclosed herein" at least include the following:

(i) molecules comprising one or more CBM32(s);
    (ii) molecules comprising one or more CBM47(s);
    (iii) molecules comprising one or more CBM67(s);
    (iv) molecules comprising one or more CBM70(s);
    (v) molecules comprising Cp2CBM32TD;
    (vi) molecules comprising Sp2CBM47TD;
    (vii) molecules comprising Sa2CBM67TD; and
    (viii) molecules comprising Sp2CBM70TD;

In one aspect, there is provided a molecule comprising a CBM32 for use in a method of modulating cell growth and/or cell activity. The molecule comprising CBM32 may comprise or be Cp2CBM32TD.

In another aspect, there is provided a molecule comprising a CBM47 for use in a method of modulating cell growth and/or cell activity. The molecule comprising CBM47 may comprise or be Sp2CBM47TD.

In a further aspect, there is provided a molecule comprising a CBM67 for use in a method of modulating cell growth and/or cell activity. The molecule comprising CBM67 may comprise or be Sa2CBM67TD.

Additionally, there is provided a molecule comprising a CBM70 for use in a method of modulating cell growth and/or cell activity. The molecule comprising CBM70 may comprise or be Sp2CBM70TD.

Another aspect, provides a method of modulating cell growth and/or activity, said method comprising contacting a cell with a molecule comprising CBM32. The method may be an in vitro method. The molecule comprising CBM32 may comprise or be Cp2CBM32TD.

An additional aspect provides a method of modulating cell growth and/or activity, said method comprising contacting a cell with a molecule comprising CBM47. The method may be an in vitro method. The molecule comprising CBM47 may comprise or be Sp2CBM47TD.

A further aspect provides a method of modulating cell growth and/or activity, said method comprising contacting a cell with a molecule comprising CBM67. The method may be an in vitro method. The molecule comprising CBM67 may comprise or be Sa2CBM67TD.

Another aspect provides a method of modulating cell growth and/or activity, said method comprising contacting a cell with a molecule comprising CBM70. The method may be an in vitro method. The molecule comprising CBM70 may comprise or be Sp2CBM70TD.

As stated, a "molecule comprising a CBM32", a "molecule comprising a CBM47", a "molecule comprising a CBM67" and/or a "molecule comprising a CBM70"—may consist essentially of the respective CBM32, CBM47, CBM67 or CBM70 or may consist of the respective CBM32, CBM47, CBM67 or CBM70.

The CBM32, CBM47, CBM67 or CBM70 component of a molecule referred to in the above aspects may comprise the complete wild-type CBM32, CBM47, CBM67 or CBM70 sequences (as provided by each of SEQ ID NOS: 1-8 above). Additionally, or alternatively, the various aspects of this disclosure may exploit a carbohydrate binding fragment of any of the CBM32, 47, 67 or 70 sequences disclosed herein (including the sequences of SEQ ID NOS: 1-8).

It should be noted that the term CBM32, CBM47, CBM67 or CBM70 further embraces recombinant molecules generated from reference CBM32, CBM47, CBM67 or CBM70 sequences (including SEQ ID NOS: 1-8). Again, these recombinant molecules can comprise full length CBM32, CBM47, CBM67 or CBM70 sequences or carbohydrate binding fragments thereof.

For convenience, the term CBM32/47/67/70 will be used to refer to all of the above described CBM molecules (which molecules comprise, consist essentially of, or consist of one or more CBM32(s), one or more CBM47(s), one or more CBM67(s) or one or more CBM70(s) or carbohydrate binding fragments of any of these.

The term "modulating" may embrace any increase or decrease in one or more aspects of cell growth and/or activity. In other words, a molecule described herein (for example, a molecule comprising one or more CBM32/47/

67/70(s)) may either inhibit certain aspects of cell growth and/or activity or may induce or stimulate other aspects of cell growth and/or activity.

The terms "growth" and "activity" as applied to cells may embrace processes and/or phenomena associated with one or more of cell proliferation, cell viability, cell migration, cell metabolism, cell differentiation and/or cell morphology/phenotype. The terms "growth" and/or "activity" may further include the response of a cell to certain exogenous and/or endogenous factors or stimuli including, for example, responses to certain compounds of the immune system, cytokines, chemokines and one or more environmental factors (light, temperature, pressure, mechanical stress and the like). Thus, the CBM32/47/67/70 molecules disclosed herein may be used to modulate (inhibit, decrease or increase) levels of cell responsiveness.

Given that CBM32/47/67/70 have been shown to modulate cell growth and activity (as described above), it will be appreciated that these molecules may be put to a number of related medical and veterinary applications and uses.

For example, a molecule comprising one or more CBM32/47/67/70(s) may be applied to the treatment and/or prevention of a disease or condition in which aberrant cell growth, and/or aberrant cell activity is a factor.

Disclosed herein is a molecule comprising a CBM32/47/67/70 for use in treating and/or preventing a disease and/or condition caused, contributed to and/or characterised by aberrant cell growth and/or activity. The molecule comprising a CBM32/47/67/70 may be selected from the group consisting of:

(i) a molecule comprising one or more CpCBM32(s);
(ii) a molecule comprising one or more SpCBM47(s);
(iii) a molecule comprising one or more SaCBM67(s);
(iv) a molecule comprising one or more SpCBM70(s);
(v) a molecule comprising Cp2CBM32TD;
(vi) a molecule comprising Sp2CBM47TD;
(vii) a molecule comprising Sa2CBM67TD; and
(viii) a molecule comprising Sp2CBM70TD.

Further, disclosed is the use of a molecule comprising a CBM32/47/67/70 for the manufacture of a medicament for the treatment and/or prevention of a disease and/or condition caused, contributed to and/or characterised by aberrant cell growth and/or activity.

The molecule comprising a CBM32/47/67/70 may be selected from the group consisting of:

(i) a molecule comprising one or more CpCBM32(s);
(ii) a molecule comprising one or more SpCBM47(s);
(iii) a molecule comprising one or more SaCBM67(s);
(iv) a molecule comprising one or more SpCBM70(s);
(v) a molecule comprising Cp2CBM32TD;
(vi) a molecule comprising Sp2CBM47TD;
(vii) a molecule comprising Sa2CBM67TD; and
(viii) a molecule comprising Sp2CBM70TD.

The disclosure also provides a method of treating and/or preventing a disease and/or condition caused, contributed to and/or characterised by aberrant cell growth and/or activity, said method comprising the step of administering a therapeutically effective amount of a molecule comprising a CBM32/47/67/70 to a subject in need thereof. The molecule comprising a CBM32/47/67/70 may be selected from the group consisting of:

(i) a molecule comprising one or more CpCBM32(s);
(ii) a molecule comprising one or more SpCBM47(s);
(iii) a molecule comprising one or more SaCBM67(s);
(iv) a molecule comprising one or more SpCBM70(s);
(v) a molecule comprising Cp2CBM32TD;
(vi) a molecule comprising Sp2CBM47TD;

(vii) a molecule comprising Sa2CBM67TD; and (viii) a molecule comprising Sp2CBM70TD.

Diseases which are caused, contributed to or characterised by aberrant cell growth and/or activity may include, for example cell proliferation disorders including, those referred to or classified as benign or malignant conditions. For example, the term "cell proliferation disorders" may include those diseases and/or conditions collectively referred to as "cancer". The term "cancer" may include, but is not limited to, those cancers referred to as forms of breast cancer, colon cancer, lung cancer, ovarian cancer, glioma and melanoma. In particular, the term cancer (or cell proliferation disorder) may relate to colon cancer, lung cancer and ovarian cancer.

The term "cancer" may also include those diseases and/or conditions collectively referred to as "leukaemia" (both chronic and acute) and any cancer affecting a mucosal/mucosal associated surface or tissue.

As such, a molecule comprising a CBM32/47/67/70 described herein may find application in the treatment and/or prevention of cancer. The molecule comprising a CBM32/47/67/70 may be selected from the group consisting of:

(i) a molecule comprising one or more CpCBM32(s);

(ii) a molecule comprising one or more SpCBM47(s);

(iii) a molecule comprising one or more SaCBM67(s);

(iv) a molecule comprising one or more SpCBM70(s);

(v) a molecule comprising Cp2CBM32TD;

(vi) a molecule comprising Sp2CBM47TD;

(vii) a molecule comprising Sa2CBM67TD; and (viii) a molecule comprising Sp2CBM70TD.

Thus, there is provided a molecule comprising a CBM32/47/67/70 for use in treating and/or preventing cancer. The molecule comprising a CBM32/47/67/70 may be selected from the group consisting of:

(i) a molecule comprising one or more CpCBM32(s);

(ii) a molecule comprising one or more SpCBM47(s);

(iii) a molecule comprising one or more SaCBM67(s);

(iv) a molecule comprising one or more SpCBM70(s);

(v) a molecule comprising Cp2CBM32TD;

(vi) a molecule comprising Sp2CBM47TD;

(vii) a molecule comprising Sa2CBM67TD; and (viii) a molecule comprising Sp2CBM70TD.

Additionally, there is provided use of a molecule comprising a CBM32/47/67/70 for the manufacture of a medicament for the treatment and/or prevention of cancer. The molecule comprising a CBM32/47/67/70 may be selected from the group consisting of:

(i) a molecule comprising one or more CpCBM32(s);

(ii) a molecule comprising one or more SpCBM47(s);

(iii) a molecule comprising one or more SaCBM67(s);

(iv) a molecule comprising one or more SpCBM70(s);

(v) a molecule comprising Cp2CBM32TD;

(vi) a molecule comprising Sp2CBM47TD;

(vii) a molecule comprising Sa2CBM67TD; and (viii) a molecule comprising Sp2CBM70TD.

Also provided is a method of treating and/or preventing cancer, said method comprising the step of administering a therapeutically effective amount of a molecule comprising a CBM32/47/67/70 to a subject in need thereof. The molecule comprising a CBM32/47/67/70 may be selected from the group consisting of:

(i) a molecule comprising one or more CpCBM32(s);

(ii) a molecule comprising one or more SpCBM47(s);

(iii) a molecule comprising one or more SaCBM67(s);

(iv) a molecule comprising one or more SpCBM70(s);

(v) a molecule comprising Cp2CBM32TD;

(vi) a molecule comprising Sp2CBM47TD;

(vii) a molecule comprising Sa2CBM67TD; and (viii) a molecule comprising Sp2CBM70TD.

In addition to the general finding that molecules comprising a CBM32/47/67/70 may be useful in the treatment and/or prevention of cancer, molecules comprising one or more CBM32(s) may find particular application in the treatment and/or prevention of a number of specific cancers.

Accordingly, the disclosure further provides a molecule comprising one or more CBM32(s) for use in the treatment and/or prevention of a cancer selected from the group consisting of:

(a) ovarian cancer;

(b) lung cancer;

(c) colon cancer; and (d) breast cancer.

In view of the above, the disclosure provides:

(i) a molecule comprising one or more CBM32(s) for use in treating and/or preventing a cancer;

(ii) the use of a molecule comprising one or more CBM32 (s) in the manufacture of a medicament for the treatment and/or prevention of a cancer; and (iii) a method of treating and/or preventing a cancer by administering a therapeutically effective amount of a molecule comprising one or more CBM32(s) to a subject in need thereof, wherein for each of (i), (ii) and (iii) the cancer is one or more selected from the group consisting of:

(a) ovarian cancer;

(b) lung cancer;

(c) colon cancer; and (d) breast cancer.

In other words, in addition to being useful in the treatment and/or prevention of each of these individual cancers, each of the CBM32s disclosed herein may find use in the treatment and/or prevention of two, three or all four of the cancers (a) to (d).

Suitable CBM32s for use in treating and/or preventing any one, two, three or all four of the cancers (a) to (d) may include any of those CBM32s disclosed herein. By way of example only, in some cases, the molecule for use in such methods may be selected from the group consisting of:

(i) a molecule comprising one, two or more CBM32(s);

(ii) a molecule comprising one, two or more CpCBM32 (s);

(iii) a molecule comprising one, two or more peptides comprising a sequence of SEQ ID NO: 1, 2, or a carbohydrate binding portion thereof; and (iv) a molecule comprising CpCBM32TD.

Whilst the inventors have identified that CBM32s have general efficacy against a wide range of cancers, in some instances, a molecule comprising one or more CBM32(s) may not demonstrate the same level of efficacy against certain specific cancer types. Thus, in relation to a molecule comprising one or more CBM32(s), the treatment and/or prevention of cancer may exclude the treatment of one or more cancers selected from melanoma, pancreatic cancer and glioma.

The disclosure further provides a molecule comprising a CBM32 and/or a CBM40 for use in treating and/or preventing a refractory (or resistant) cancer.

In addition to the CBM32s already described herein, an exemplary CBM40 for use may comprise the sialic acid binding domain of *Vibrio cholerae* NanH sialidase (VcCBM: a CBM40) and/or the equivalent (or homologous) domain from *Streptococcus pneumoniae* NanA sialidase (SpCBM: also a CBM40). Of course, similar or homologous sialic acid binding modules present in other organisms are to be encompassed within the scope of the terms "CBM" and "CBM40". An exemplary *Vibrio cholerae* NanH sialidase amino acid sequence is deposited under accession number A5F7A4 and is reproduced below as SEQ ID NO: 23 (781 amino acids).

```
MRFKNVKKTA LMLAMFGMAT SSNAALFDYN

ATGDTEFDSP AKQGWMQDNT NNGSGVLTNA

DGMPAWLVQG IGGRAQWTYS LSTNQHAQAS

SFGWRMTTEM KVLSGGMITN YYANGTQRVL

PIISLDSSGN LVVEFEGQTG RTVLATGTAA

TEYHKFELVF LPGSNPSASF YFDGKLIRDN

IQPTASKQNM IVWGNGSSNT DGVAAYRDIK

FEIQGDVIFR GPDRIPSIVA SSVTPGVVTA

FAEKRVGGGD PGALSNTNDI ITRTSRDGGI

TWDTELNLTE QINVSDEFDF SDPRPIYDPS

SNTVLVSYAR WPTDAAQNGD RIKPWMPNGI

FYSVYDVASG NWQAPIDVTD QVKERSFQIA

GWGGSELYRR NTSLNSQQDW QSNAKIRIVD

GAANQIQVAD GSRKYVVTLS IDESGGLVAN

LNGVSAPIIL QSEHAKVHSF HDYELQYSAL

NHTTTLFVDG QQITTWAGEV SQENNIQFGN

ADAQIDGRLH VQKIVLTQQG HNLVEFDAFY

LAQQTPEVEK DLEKLGWTKI KTGNTMSLYG

NASVNPGPGH GITLTRQQNI SGSQNGRLIY

PAIVLDRFFL NVMSIYSDDG GSNWQTGSTL

PIPFRWKSSS ILETLEPSEA DMVELQNGDL

LLTARLDFNQ IVNGVNYSPR QQFLSKDGGI

TWSLLEANNA NVFSNISTGT VDASITRFEQ

SDGSHFLLFT NPQGNPAGTN GRQNLGLWFS

FDEGVTWKGP IQLVNGASAY SDIYQLDSEN

AIVIVETDNS NMRILRMPIT LLKQKLTLSQ

N
```

The CBM region of SEQ ID NO: 24 is from amino acid residue 25 to 216—this sequence may be SEQ ID NO: 25.

An exemplary *Streptococcus pneumoniae* NanA sialidase amino acid sequence has been deposited under accession number P62575 and is reproduced below as SEQ ID NO: 26 (1035 amino acids).

```
MSYFRNRDID IERNSMNRSV QERKCRYSIR

KLSVGAVSMI VGAVVFGTSP VLAQEGASEQ

PLANETQLSG ESSTLTDTEK SQPSSETELS

GNKQEQERKD KQEEKIPRDY YARDLENVET

VIEKEDVETN ASNGQRVDLS SELDKLKKLE
```

```
-continued
NATVHMEFKP DAKAPAFYNL FSVSSATKKD

EYFTMAVYNN TATLEGRGSD GKQFYNNYND

APLKVKPGQW NSVTFTVEKP TAELPKGRVR

LYVNGVLSRT SLRSGNFIKD MPDVTHVQIG

ATKRANNTVW GSNLQIRNLT VYNRALTPEE

VQKRSQLFKR SDLEKKLPEG AALTEKTDIF

ESGRNGKPNK DGIKSYRIPA LLKTDKGTLI

AGADERRLHS SDWGDIGMVI RRSEDNGKTW

GDRVTITNLR DNPKASDPSI GSPVNIDMVL

VQDPETKRIF SIYDMFPEGK GIFGMSSQKE

EAYKKIDGKT YQILYREGEK GAYTIRENGT

VYTPDGKATD YRVVVDPVKP AYSDKGDLYK

GNQLLGNIYF TTNKTSPFRI AKDSYLWMSY

SDDDGKTWSA PQDITPMVKA DWMKFLGVGP

GTGIVLRNGP HKGRILIPVY TTNNVSHLNG

SQSSRIIYSD DHGKTWHAGE AVNDNRQVDG

QKIHSSTMNN RRAQNTESTV VQLNNGDVKL

FMRGLTGDLQ VATSKDGGVT WEKDIKRYPQ

VKDVYVQMSA IHTMHEGKEY IILSNAGGPK

RENGMVHLAR VEENGELTWL KHNPIQKGEF

AYNSLQELGN GEYGILYEHT EKGQNAYTLS

FRKFNWDFLS KDLISPTEAK VKRTREMGKG

VIGLEFDSEV LVNKAPTLQL ANGKTARFMT

QYDTKTLLFT VDSEDMGQKV TGLAEGAIES

MHNLPVSVAG TKLSNGMNGS EAAVHEVPEY

TGPLGTSGEE PAPTVEKPEY TGPLGTSGEE

PAPTVEKPEY TGPLGTAGEE AAPTVEKPEF

TGGVNGTEPA VHEIAEYKGS DSLVTLTTKE

DYTYKAPLAQ QALPETGNKE SDLLASLGLT

AFFLGLFTLG KKREQ
```

The CBM region of SEQ ID NO: 26 is from amino acid residue 121 to 305—this sequence may be SEQ ID NO: 27.

Thus, molecules for use in the treatment of refractory cancer may comprise a protein or peptide having the sequence of SEQ ID NO: 24 or 25 or a sialic acid binding fragment thereof. For example, a useful sialic acid binding molecule may comprise a proteinaceous moiety encoded by the sialic acid binding domain of the nanH gene (encoding sialidase) of *V. cholerae* (as provided by SEQ ID NO: 24) or an equivalent or homologous gene present in another organism (for example, the equivalent/homologous nanA sialidase gene of *S. pneumoniae*: see SEQ ID NO: 26). A CBM40 for use in the treatment of refractory cancer may comprise from about residue 1, 5, 10, 15, 25 or 30 (i.e. from 1-30 or from any amino acid residue there between) to about residue 150, 175, 200, 210, 216, 220-781 (to any residue from 150 to 781 including any residue therebetween) of the *V. cholerae* sialidase molecule of SEQ ID NOS: 24 or 25. For example, a CBM40 for use in the treatment of refractory cancer may comprise a peptide having a sequence corresponding to residue 25 to about residue 216 of SEQ ID NO: 24 above.

A further suitable CBM40 for use in the treatment of refractory cancer may comprise a protein or peptide having the sequence of SEQ ID NO: 26 or 27 or a sialic acid binding fragment thereof. For example, a useful may comprise a proteinaceous moiety encoded by the sialic acid binding domain of the *Streptococcus pneumoniae* nanA gene (encoding sialidase). A CBM40 for use in the treatment of cancer may comprise from about residue 80, 90, 100, 110, 120, 121 to 130 (i.e. from any of about residues 80 to 130 including any residue therebetween) to about residue 250, 275, 300, 305, 310, 320-1035 (i.e. to any residue from about 250-1035 including to about any residue therebetween) of the *S. pneumoniae* sialidase molecule of SEQ ID NOS: 26 or 27. For example, a CBM40 for use may comprise a peptide having a sequence corresponding to residue 121 to about residue 305 of SEQ ID NO: 26 above.

One of skill will appreciate that useful CBM40s may comprise sequences which exhibit some degree (for example, 99%, 95%, 90%, 85%, 80%, 75%, 70%, 65% or 60%) sequence identity or homology with the CBM40 sequences of SEQ ID NOS: 24, 25, 26 and 27. All such variant or divergent sequences are to be embraced within the scope of this disclosure and by the term "CBM40". Identical and/or homologous CBM40 sequences may have carbohydrate binding function.

A molecule for use in the treatment of refractory cancer may comprise one or more CBM40s. A molecule may comprise a single or individual CBM40—for example, a single VcCBM40 or a single SpCBM40. Alternatively, a molecule for use may comprise a plurality or multiple (i.e. two or more) CBM40s. Molecules which comprise a plurality of CBMs may be termed "multivalent" molecules or CBMs. A multivalent CBM may, for example, comprise two or more VcCBM40s or two or more SpCBM40s. A multivalent CBM may comprise a mixture of different CBMs, for example, one or more VcCBMs with one or more SpCBMs.

The molecule comprising a CBM32 and/or a CBM40 for use in the treatment of refractory (or resistant) cancer may be selected from the group consisting of:

(i) a molecule comprising one or more CpCBM32(s);
(ii) a molecule comprising Cp2CBM32TD;
(iii) a molecule comprising Vc2CBM40TD; and
(iv) a molecule comprising Sp2CBM40TD.

Additionally, the disclosure provides the use of a molecule comprising a CBM32 and/or CBM40 for the manufacture of a medicament for the treatment of a refractory (or resistant) cancer. The molecule comprising a CBM32 and/or CBM40 may be selected from the group consisting of:

(i) a molecule comprising one or more CpCBM32(s);
(ii) a molecule comprising Cp2CBM32TD;
(iii) a molecule comprising Vc2CBM40TD; and
(iv) a molecule comprising Sp2CBM40TD.

Also disclosed is a method of treating a refractory (or resistant) cancer, said method comprising administering a subject in need thereof a therapeutically effective amount of a molecule comprising a CBM32 and/or CBM40. The molecule comprising a CBM32 and/or CBM40 may be selected from the group consisting of:

(i) a molecule comprising one or more CpCBM32(s);
(ii) a molecule comprising Cp2CBM32TD;
(iii) a molecule comprising Vc2CBM40TD; and
(iv) a molecule comprising Sp2CBM40TD.

A subject in need thereof or indeed a subject to be administered a molecule disclosed herein or a medicament comprising the same, may be any subject suffering (or suspected as suffering) from (i) a cell proliferation disorder, (ii) cancer, (iii) any other disease and/or condition described herein; (iv) a disease or condition caused, contributed to or characterised by aberrant cell growth and/or activity; (v) one or more cancers selected from the group consisting of (a) breast cancer, (b) colon cancer, (c) lung cancer, (d) ovarian cancer, (e) glioma and (f) melanoma; (vi) one or more cancers selected from the group consisting of (a) lung cancer, (b) colon cancer and (c) ovarian cancer; and/or (v) a refractory (or resistant) cancer.

Additionally, or alternatively, any subject may be a subject predisposed or susceptible to (i) a cell proliferation disorder, (ii) cancer, (iii) any other disease and/or condition described herein; (iv) a disease or condition caused, contributed to or characterised by aberrant cell growth and/or activity; (v) one or more cancers selected from the group consisting of: (a) breast cancer; (b) colon cancer; (c) lung cancer; (d) ovarian cancer; (e) glioma and (f) melanoma; or (vi) one or more cancers selected from the group consisting of (a) lung cancer, (b) colon cancer; and (c) ovarian cancer.

Refractory or resistant cancers may include cancers that do not respond to first line or preferred medicaments (including standard or preferred chemotherapeutic or radiotherapeutic options). Refractory or resistant cancers may include those cancers that are resistant to (or do not respond to) cisplatin. The term refractory cancer or resistant cancer may embrace refractory or resistant ovarian cancer. The terms refractory (ovarian) cancer and resistant (ovarian) cancer may include ovarian cancers that are resistant to cisplatin.

Accordingly, the disclosure provides (i) a molecule comprising one or more CpCBM32(s); (ii) a molecule comprising Cp2CBM32TD; (iii) a molecule comprising Vc2CBM40TD; and/or (iv) a molecule comprising Sp2CBM40TD, for use in the treatment of refractory (or resistant) ovarian cancer.

It should be understood that any of the treatments described herein, may involve the use of one or more molecules of this disclosure to treat, ameliorate or reduce, one or more symptoms of the various diseases and disorders described herein. By way of example, the symptoms of a disease such as cancer may include, for example, the presence of tumours and/or cell masses. As such, the molecules described herein may be used to modulate (for example stop, retard, inhibit or reduce) tumour formation and/or the metastasis thereof. The molecules may also be used to reduce the overall size of a tumour. Certain tumours, including those that are large and/or aggressive, are often easier to surgically remove if they have first been reduced in size. Typically, chemo- and/or radiotherapy-based treatments might be used to reduce the size of a tumour but treatments such as this may be replaced by and/or supplemented with treatments based upon the use of a molecule comprising a CBM32/47/67/70. As stated, molecules comprising a CBM32/47/67/70 exhibit an ability to modulate cell growth and/or activity and therefore, without wishing to be bound by theory, the mechanism underpinning the ability of any one of the disclosed molecules to affect the size of a tumour may be rooted in the cell proliferation, differentiation and/or metabolism modulating effects of the molecule.

In view of the above, the successful treatment of a tumour may therefore be characterised by a reduction in tumour size, a reduction in an observed or detectable/detected level of tumour metastasis, angiogenesis within tumorigenic tissue and/or tissue invasion.

A molecule of this disclosure may be for use in methods of modulating (for example inhibiting, restricting or reducing) tumour growth, development and/or metastasis in subjects in need thereof. The molecules described herein may be formulated as compositions for use in modulating tumour growth, development and/or metastasis or used in the manufacture of medicaments for achieving the same. This disclosure also provides a molecule comprising a CBM32/47/67/70 for use in treating a tumour. Further, described is the use of a molecule comprising a CBM32/47/67/70 for the manufacture of a medicament for treating a tumour. Also, the disclosure provides a method of treating a tumour, said method comprising administering a molecule comprising a CBM32/47/67/70 to a subject (or tumorigenic tissue) in need thereof.

As defined earlier, the term "a subject in need thereof" may embrace any subject suspected as having a tumour or diagnosed with a tumour and/or subjects that are identified as being predisposed and/or susceptible to tumours. The term "tumours" may include refractory or resistant tumours. The term tumours may include refractory or resistant ovarian cancer tumours.

The present disclosure therefore provides various applications for molecules comprising a CBM32/47/67/70 and which have been identified as modulators of cell growth and/or activity. Any given molecule (comprising a CBM32/47/67/70) may be identified as a modulator of cell growth and/or activity via the various experiments and assays described in the examples section of this patent application. For example, the cell wound scratch assay is one example of an assay that may be adapted to determine whether any given "test" molecule exhibits the necessary ability to modulate cell growth, cell migration and/or activity. Additionally, or alternatively, a BrdU cell proliferation assay may be used to determine any effect of a test agent (for example, a molecule comprising a CBM32/47/67/70) on cell proliferation, growth and/or activity. Briefly, cells may be cultured in a medium supplemented with BrdU—as cells grow and proliferate, the BrdU is incorporated into de novo-synthesized DNA as a substitute for thymidine. This labels progeny cells and the amount of BrdU incorporation can be used as a measure or indicator of cell proliferation/growth. BrdU detection may be achieved by the use of antibodies with specificity or affinity for BrdU.

In other cases, a metabolic-based assay, such as a Cell-Titer-Glo® 2.0 Assay (CTG®2.0) may be used to determine any effect of a test agent (for example, a molecule comprising a CBM32/47/67/70) on cell proliferation, growth and/or activity. In such assays, an amount of ATP (adenosine triphosphate) may be assessed to determine a number of metabolically active cells (and so may provide a measure of viable cells). The number of viable cells following treatment with a test agent may be used as a measure or indicator of cell proliferation/growth.

Alternatively or additionally, a DNA-staining based assay such as a CyQUANT® Direct Cell Proliferation Assay may be used to determine any effect of a test agent (for example, a molecule comprising a CBM32/47/67/70) on cell proliferation, growth and/or activity. In such assays, the number of viable cells may be determined using a DNA stain, e.g. a cell-permeant DNA-binding dye. Again, the number of viable cells following treatment with a test agent may be used as a measure or indicator of cell proliferation/growth.

Thus, the disclosure could relate to those molecules which, via a cell activity modulation assay (for example, a cell wound scratch assay), exhibit an ability to modulate cell growth and/or activity. To this end, the disclosure further provides a method of identifying molecules (including molecules comprising a CBM32/47/67/70) for use in methods of modulating cell growth and/or activity or for the various medical and/or veterinary applications described herein, said method comprising subjecting a test compound to an assay capable of reporting an effect of the test compound on cell growth and/or activity, wherein the test compound is a molecule comprising a CBM32/47/67/70 and if the assay reports that the compound has an effect on any aspect of cell growth and/or activity, the compound may be useful in the treatment and/or prevention of diseases and/or conditions of the type described herein. The assay which is capable of reporting an effect of the test compound on cell growth and/or activity may be a cell wound scratch assay, BrdU type, a CellTiter-Glo® 2.0 type and/or a CyQUANT® Direct Cell Proliferation assay as described herein.

Molecules which comprise a CBM32/47/67/70, may find further application as molecules which may be conjugated, bound or joined to or associated with, other entities for the purpose of targeting or delivering that entity to some tissue or cell.

Molecules of this type may be otherwise known as "therapeutic warheads" or "conjugates". Without wishing to be bound by theory, the presence of ligands for the various CBMs which may be comprised within the molecules of this disclosure (for example CBM32, CBM47, CBM67 and/or CBM70) in certain cell receptors and membrane bound molecules, may allow the various molecules described herein to be exploited as a means to deliver conjugated heterologous molecules (that is, a molecule distinct from and different to the molecule comprising a CBM32/47/67/70) to said cells or tissues comprising said cells. Such, conjugated molecules may be useful in the treatment of cancer, where the molecules described herein (which molecules exhibit affinity for carbohydrates expressed on the surface of cells) may be used to direct therapeutic and/or cytotoxic moieties thereto.

By way of example, a molecule as described herein (including any of the CBM32/47/67/70 molecules) may be conjugated to one or more (for example, two, three, four or more) moieties which are, for example, therapeutic and/or cytotoxic. Thus, the disclosure relates to CBM32/47/67/70 molecule conjugates.

CBM32/47/67/70 molecule conjugates may comprise a CBM32/47/67/70 molecule of this disclosure conjugated (joined, bound or otherwise associated with) to a heterologous moiety. The heterologous moiety may comprise a therapeutic and/or cytotoxic moiety which may be conjugated to some part of the CBM32/47/67/70 molecule.

For example, the heterologous moiety may be conjugated to one or both ends of the CBM32/47/67/70 molecule. The heterologous moiety may be additionally or alternately conjugated (or even fused) to an internal portion of the CBM32/47/67/70 molecule. It will be appreciated that however the heterologous moiety is to be conjugated to the CBM32/47/67/70 molecule, the molecule (nor its conjugation) should not (substantially) interfere with or ablate or reduce the carbohydrate binding property of the CBM32/47/67/70 molecule.

As stated, the heterologous moiety may be a drug useful in the treatment of a disease which affects a cell or tissue expressing a receptor which comprises the ligand for any one of the CBM32, CBM47, CBM67 or CBM70 molecules. For example, the drug may be a chemotherapeutic drug for use in the treatment of cancer and the like. The heterologous moiety may be a cytotoxic moiety capable of killing or inducing apoptosis in, a cell. The heterologous moiety may comprise a molecule which is able to recruit specific cells to or into a particular tissue. For example, the heterologous moiety may be, for example, a T cell receptor (TCR) which may be used as a means to recruit T cells to, for example a tumour or cancerous tissue.

The present disclosure may provide compositions for use in the various uses, medicaments and methods described herein. As such, any of the molecules comprising a CBM32/47/67/70 described herein may be formulated for use.

For convenience, and with reference to the section below describing compositions, formulations and the like, it should be noted that both molecules comprising a CBM32/47/67/10 as described herein and any conjugates comprising the same (for example, CBM32/47/67/70::drug conjugates/fusions) shall be included under the general term "molecule comprising a CBM32/47/67/70".

A molecule comprising a CBM32/47/67/70 may be formulated for use and as a therapeutic or pharmaceutical composition. The various compositions may comprise one or more of the molecules described herein and any given treatment may require the administration (together, concurrently or separately) of one or more of these compositions. It should be noted that a composition according to this disclosure may further comprise one or more other therapeutic moieties—for example, molecules, small molecules, antibodies, oligonucleotides and the like useful in the treatment of one or more diseases and/or conditions. Additionally, or alternatively, a molecule comprising a CBM32/47/67/70 may be administered together with one or more other (different) therapeutic entities—wherein the one or more other (different) therapeutic entities may be used for the treatment of the same or a different disease. The term "administered together" embraces administration of a CBM32/47/67/70 before, after and/or at the same time as the administration of the one or more other therapeutic entities.

The molecules described herein may be formulated for enteral (including oral), parenteral and/or topical administration and one of skill will appreciate that the precise formulation may vary depending on the route of administration.

Pharmaceutical compositions according to the present invention may be prepared conventionally, comprising substances that are customarily used in pharmaceuticals as described in, for example, Remington's The Sciences and Practice of Pharmacy, 22nd Edition (Pharmaceutical Press 2012) and/or Handbook of Pharmaceutical Excipients, 7th edition (compiled by Rowe et al, Pharmaceutical Press, 2012)—the entire content of all of these documents and references being incorporated by reference.

A therapeutic or pharmaceutical composition of this disclosure (that is a composition comprising a molecule comprising a CBM32/47/67/70 and for use in any of the medicaments or methods described herein—including the methods of or medicaments for, modulating cell growth and/or activity and/or treating cancer) may be formulated together with one or more pharmaceutically acceptable excipients, carriers, adjuvants and buffers. The compositions can be administered, e.g. orally (including mucosally), parentally, intraperitoneally, enterally, intramuscularly, subcutaneously, intravenously or via any other routes useful to achieve the desired effect (in this case effects which include, modulation of cell growth/activity, treatment or prevention of diseases/conditions associated with the same and/or cancer and/or modulation of tumour growth). As stated, depending on the chosen route of administration, the exact composition of the formulation may vary.

A therapeutic or pharmaceutical formulation comprising a molecule comprising a CBM32/47/67/70 and for administration to a subject may be coated, encapsulated or enveloped in a material which protects the molecule from the action of enzymes, acids and other natural compounds/conditions (including, for example, compounds (including antibodies), cells and processes of the immune system) which may inactivate or denature the compound and/or its carbohydrate binding properties.

Among the various standard and conventional excipients that may be available for use in compositions comprising the molecules described herein, are those pharmaceutically acceptable organic or inorganic carrier substances which are suitable for parenteral, enteral, oral (including mucosal) and other routes of administration that do not deleteriously react with the molecule(s) comprising a CBM32/47/67/70.

Where molecules comprising a CBM32/47/67/70 are to be formulated for parental administration, the compositions may be sterile.

The composition may comprise an oil-based or aqueous solution, a suspension and/or an emulsion.

In other embodiments, the composition may take the form of an implant, such as for example a (dissolvable or biodegradable) film, pessary or implant (including suppositories).

The pharmaceutical preparations comprising the molecules described herein may be mixed with stabilizers, wetting agents, emulsifiers, salts (for use in influencing osmotic pressure), buffers and/or other substances that do not react deleteriously with the active compounds.

One or more of the molecules described herein may be formulated for and administered, orally. As stated, oral administration would include mucosal administration which would itself would include administration intranasally and/or by inhalation.

Compositions for use may include solid dosage forms which are suitable for oral administration. These may include, for example capsules, tablets, pills, powders, and granules. In any given solid dosage form, a molecule comprising a CBM32/47/67/70 (or any conjugate comprising the same) may be admixed with at least one inert pharmaceutically-acceptable excipient. Examples of suitable excipients will be known to one of skill in this field but may include, for example fillers or extenders, humectants, wetting agents, binders, disintegrating agents, solution retarders, absorption accelerators, adsorbents, lubricants or mixtures thereof. A tablet, pill or capsule may further comprise a buffering agent. Solid dosage forms such as tablets, dragees, capsules, pills and/or granules also can be prepared with coatings and shells, such as coatings which protect against the gastrointestinal environment and/or stomach acid.

A solid dosage form may contain opacifying agents and can also be formulated so as to ensure the delayed release of the active agent (in this case a molecule comprising a CBM32/47/67/70 or a conjugate comprising the same) in or to a specific part of the intestinal tract.

Solid compositions for oral administration can be formulated in a unit dosage form, each dosage containing an appropriate dose of a molecule comprising a CBM32/47/67/70 (or conjugate comprising the same). The exact amount of a molecule comprising a CBM32/47/67/70 (or conjugate comprising the same) contained within any given solid dosage form will vary depending on the intended use. A solid composition may contain a "unit dose"—a unit dose containing a quantity of a molecule comprising a CBM32/47/67/70 (or conjugate containing the same) calculated to produce the desired effect (for example modulation of cell growth and/or activity) over the course of a treatment period.

Liquid dosage forms for oral administration may (as stated) include emulsions, solutions, suspensions, syrups, and elixirs. In addition to the compound or composition, the liquid dosage forms may contain inert diluents commonly used in the art, such as water or other solvents, solubilizing agents and emulsifiers.

Any of the disclosed molecules may be used in any suitable amount. As stated, the acid molecules may be formulated for oral, mucosal or parenteral administration and as such, the precise formulation may depend on the intended route of administration. The amount of a molecule comprising a CBM32/47/67/70 present in any given dose may be in the region of 0.1 µg-1000 µg. For example, amounts of about 0.1 µg, 0.2 µg, 0.3 µg, 0.4 µg, 0.5 µg, 1 µg, 10 µg, 20 µg, 25 µg, 50 µg, 100 µg, 200 µg, 300 µg, 400 µg, 500 µg, 600 µg, 700 µg, 800 µg or 900 µg. The selected amount of the CBM32/47/67/70 molecule may be formulated in a specific volume of a pharmaceutically acceptable excipient, diluent and/or buffer. The volume of excipient, diluent or buffer may be about 10 µL to 5 mL. For example, the required amount of CBM32/47/67/70 molecule may be combined (or formulated) with about 15 µL, 20 µL, 25 µL, 30 µL, 35 µL, 40 µL, 45 µL, 50 µL, 55 µL, 60 µL, 65 µL, 70 µL, 75 µL, 80 µL, 85 µL, 90 µL, 95 µL, 100 µL, 200 µL, 250 µL, 300 µL, 400 µL, 500 µL, 600 µL, 700 µL, 800 µL, 900 µL, 1 mL, 2 mL, 3 mL or 4 mL. For example, 100 µg CBM32/47/67/70 molecule may be combined with about 250 µL of excipient to yield a final concentration of 400 µg/mL. Doses at concentrations of about 0.1 µg/mL-1 mg/mL may be used including, for example, doses at 5 µg/mL, 10 µg/mL, 20 µg/mL, 25 µg/mL, 50 µg/mL, 100 µg/mL, 200 µg/mL, 300 µg/mL, 500 µg/mL, 600 µg/mL, 700 µg/mL, 800 µg/mL or 900 µg/mL.

In use, a dose of a CBM32/47/67/70 molecule, administered as part of the treatment and/or prevention of a cell proliferation and/or differentiation disorder (for example, cancer), may be administered multiple times over a number of days, weeks months or years. For example, after an initial (or first) administration, a dose of a CBM32/47/67/70 molecule may be administered again at about (+/−1 or 2 days) 3, 4, 5, 6, 7, 17, 21, 28 and/or 35 days later. On any given day, a specific dose of a CBM32/47/67/70 molecule may be administered 1, 2, 3 or more times. Each time, the CBM32/47/67/70 molecule may be administered (by whatever route is considered best to affect a suitable treatment or to induce prophylaxis against the development of a cell proliferation and/or differentiation disorder.

DETAILED DESCRIPTION

The present invention will now be described in detail by reference to the following Figures which show:

FIG. 1: Proliferation data (BrdU incorporation assay). Different cancer cell lines (Melanoma ((a), A2058), Breast ((b), MDA.MB.231), Pancreatic ((c), PANC1) and Lung ((d), A549) were treated with Cp2CBM32TD (400 µg/mL), PBS (control), sialic acid binding CBM40 agents (Sp2CBMTD (400 µg/mL), Vc2CBMTD (400 µg/mL) or Vc4CBM (400 µg/mL)) or sialic acid binding null CBM40 mutant (Sp2(R274Q)CBMTD (400 µg/mL)) and left for 24 hours. The cells were then incubated with BrdU for 2-6 hrs. An ELISA assay was performed to measure the quantity of BrdU incorporated into the DNA. This assay is a standard assay to measure cell growth/proliferation. A two-way ANOVA was used to show statistical significance vs the control group (p of <0.0001 represented by **, p of <0.001 represented by *, p of <0.01 represented by ** and p of <0.1 represented by *)

Figure 2:
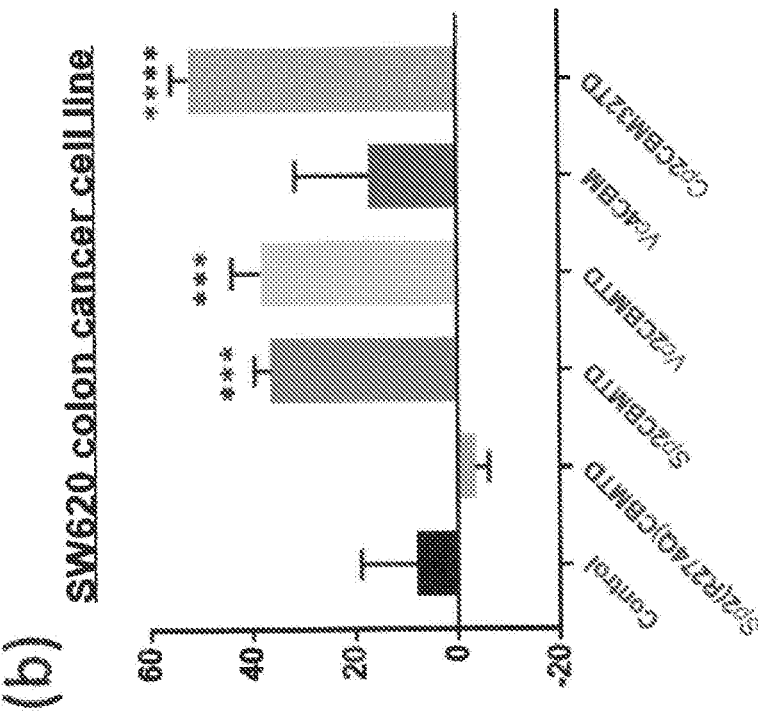
Figure 2:
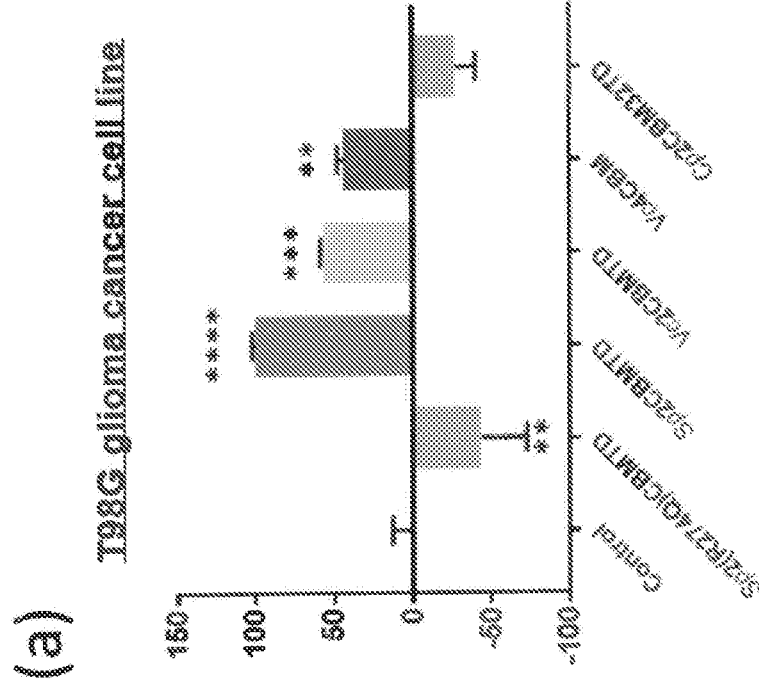
Figure 2:
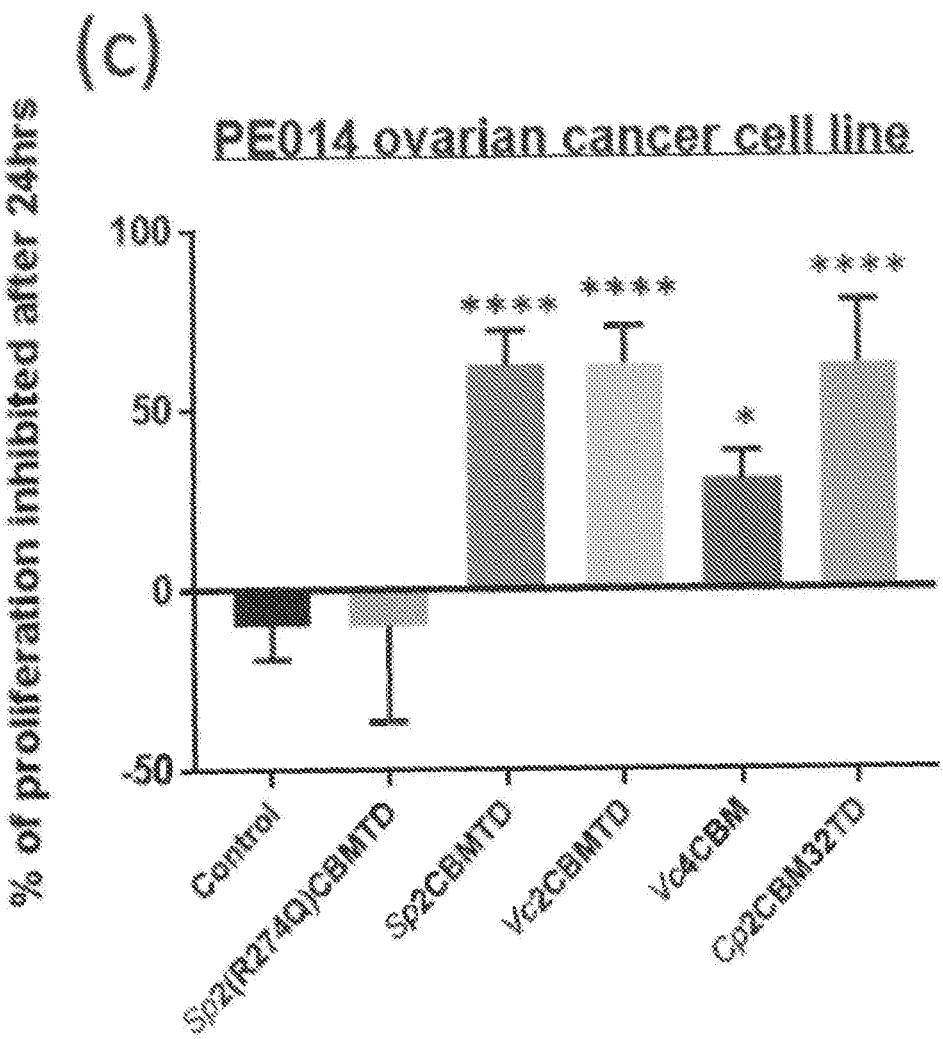

FIG. 2: Proliferation data (BrdU incorporation assay). Different cancer cell lines ((a), Glioma (T98G), Colon ((b), SW620) and Ovarian ((c), PE014)) were treated with Cp2CBM32TD (400 µg/mL), PBS (control), sialic acid binding CBM40 agents (Sp2CBMTD (400 µg/mL), Vc2CBMTD (400 µg/mL) or Vc4CBM (400 µg/mL)) or sialic acid binding null CBM40 mutant (Sp2(R274Q) CBMTD (400 µg/mL)) and left for 24 hours. The cells were then subject to a BrdU assay and incubated for 2-6 hrs. An ELISA assay was performed to measure the quantity of BrdU incorporated into the DNA. This assay is a standard assay to measure cell growth/proliferation. A two-way ANOVA was used to show statistical significance vs the control group (p of <0.0001 represented by **, p of <0.001 represented by *, p of <0.01 represented by ** and p of <0.1 represented by *).

Figure 3:
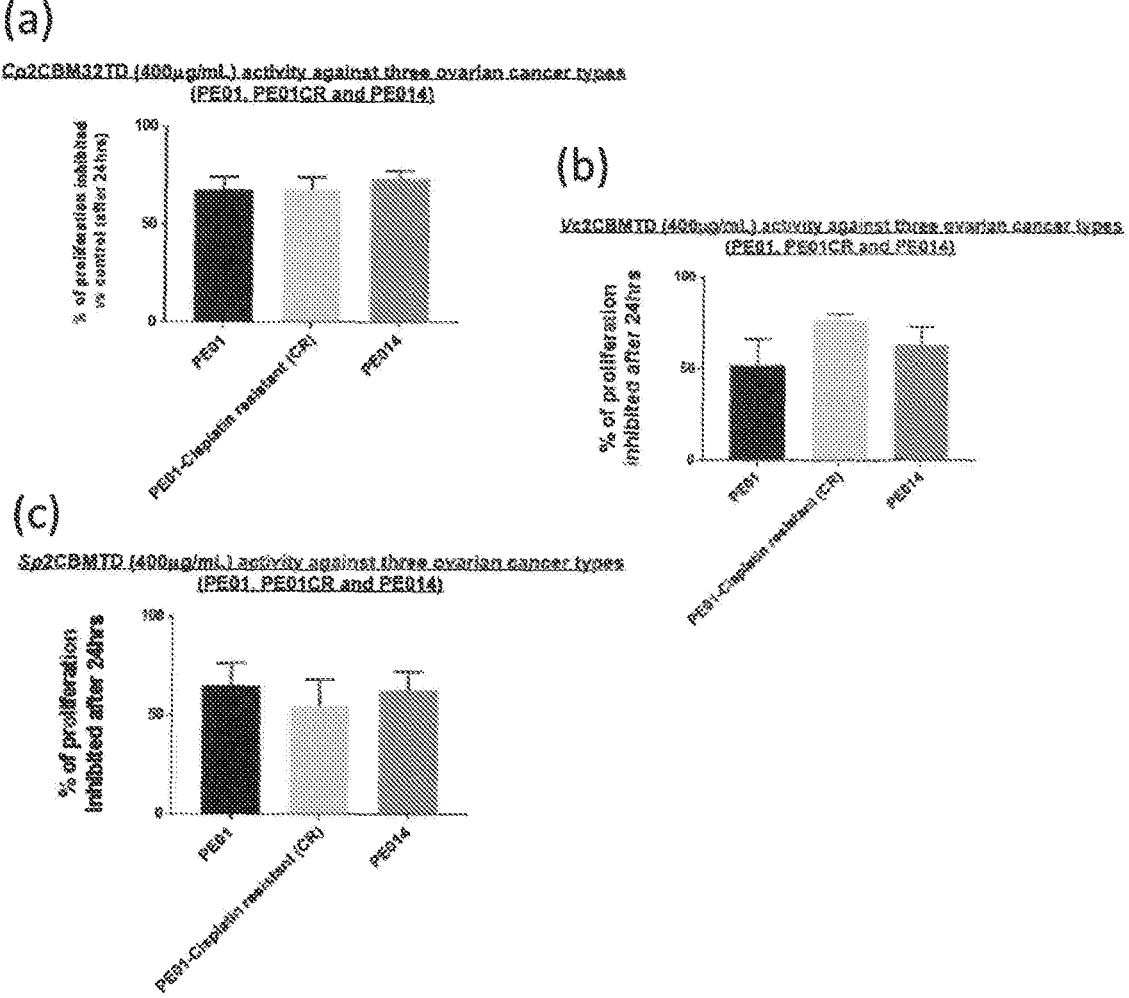

FIG. 3: Percentage inhibition of cell proliferation in human-derived metastatic ovarian cancer cell lines PE01, PE01 cisplatin-resistant (PE01-CR) and PE014. (a) using Cp2CBM32TD (GalNAc/galactose/lactose binding CBM from Clostridium perfringens) against three ovarian cell lines, including a cisplatin-resistant form (PE01-CR). (b) using Vc2CBMTD against three ovarian cell lines (PE01, PE01-CR, PE014). (c) using Sp2CBMTD against three ovarian cell lines (PE01, PE01-CR, PE014).

Figure 4:
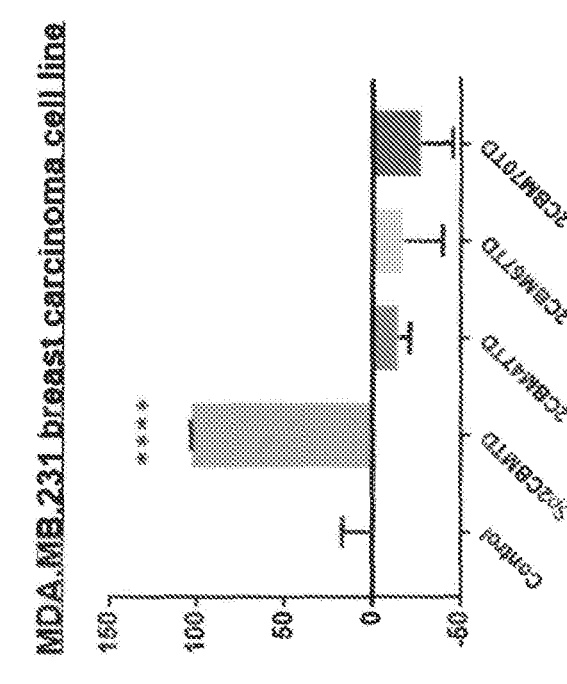
Figure 4:
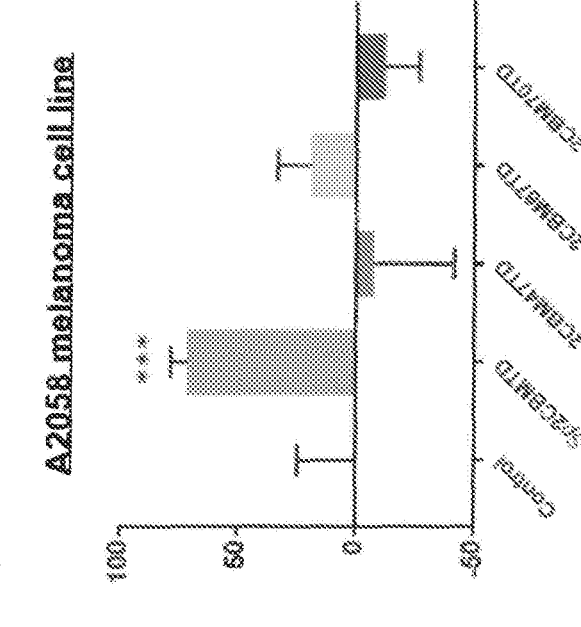
Figure 4:
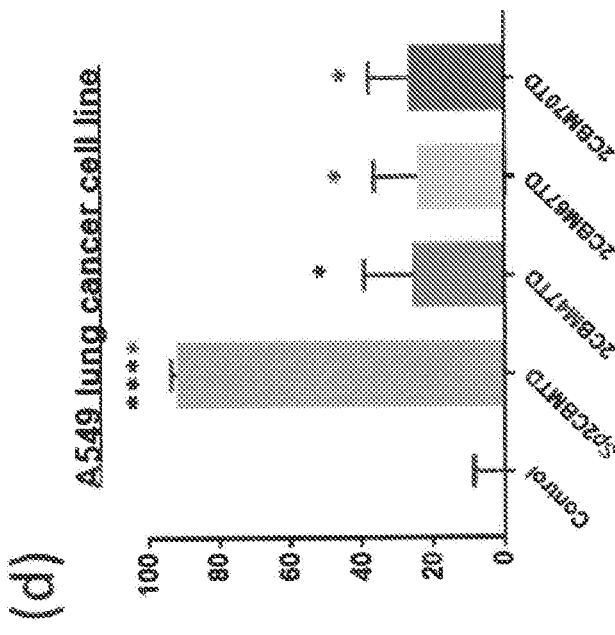
Figure 4:
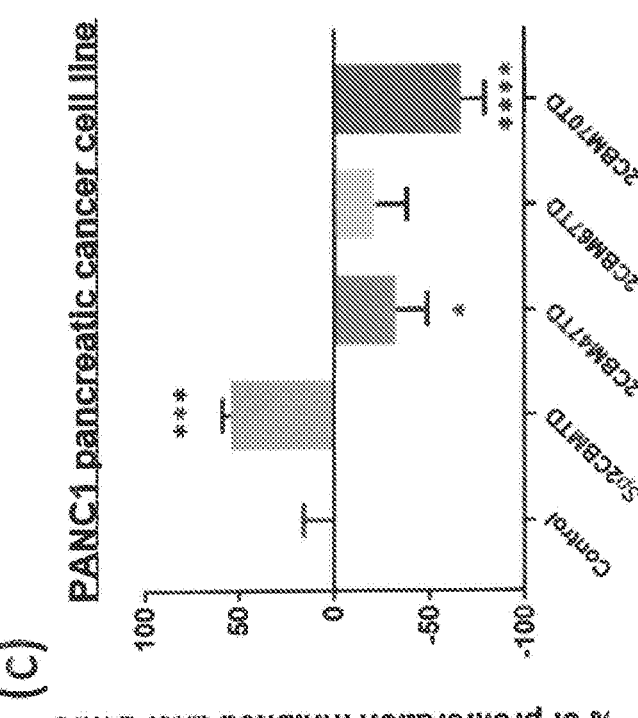

FIG. 4: Proliferation data (BrdU incorporation assay). Different cancer cell lines (Melanoma ((a), A2058), Breast ((b), MDA.MB.231), Pancreatic ((c), PANC1) and Lung ((d), A549) were treated with 2CBM47TD (400 µg/mL), 2CBM67TD (400 µg/mL), 2CBM70TD (400 µg/mL), PBS (control) or sialic acid binding CBM40 agent Sp2CBMTD (400 µg/mL) and left for 24 hours. The cells were then incubated with BrdU for 2-6 hrs. An ELISA assay was performed to measure the quantity of BrdU incorporated into the DNA. This assay is a standard assay to measure cell growth/proliferation. A two-way ANOVA was used to show statistical significance vs the control group (p of <0.0001 represented by **, p of <0.001 represented by *, p of <0.01 represented by ** and p of <0.1 represented by *).

Figure 5:
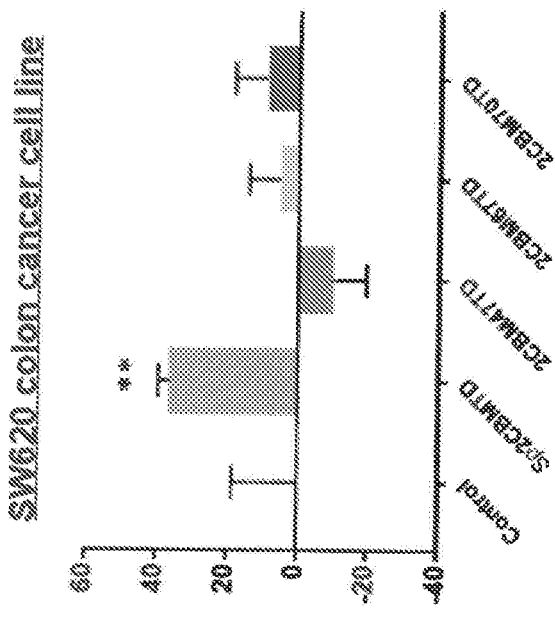
Figure 5:
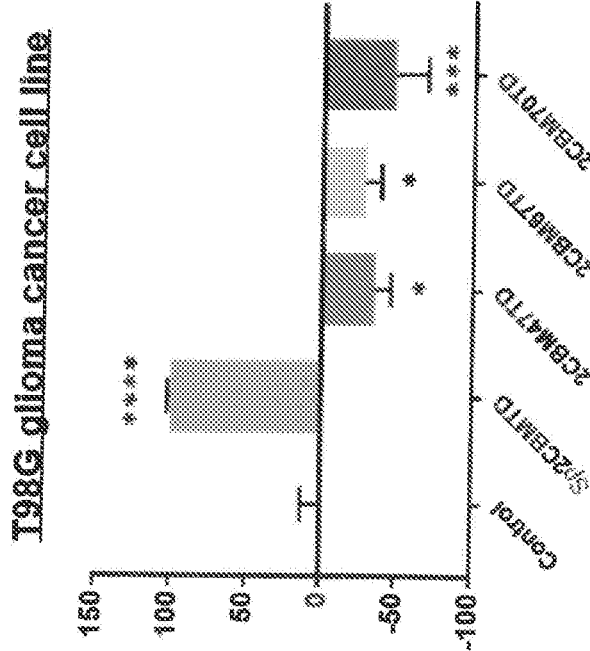
Figure 5:
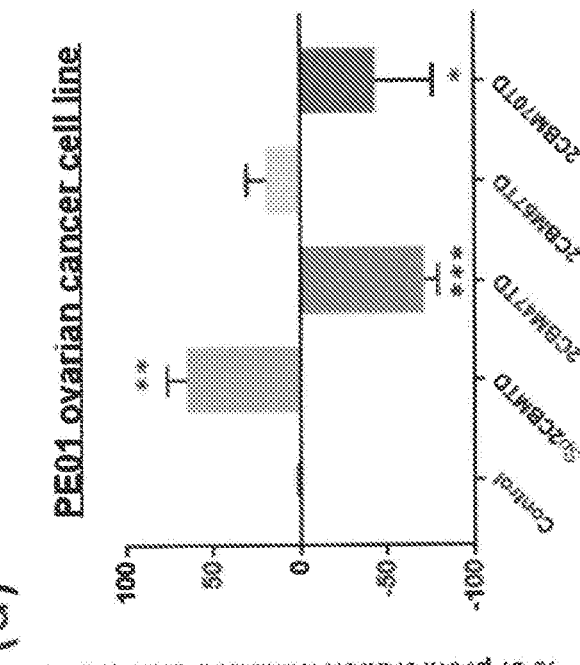
Figure 5:
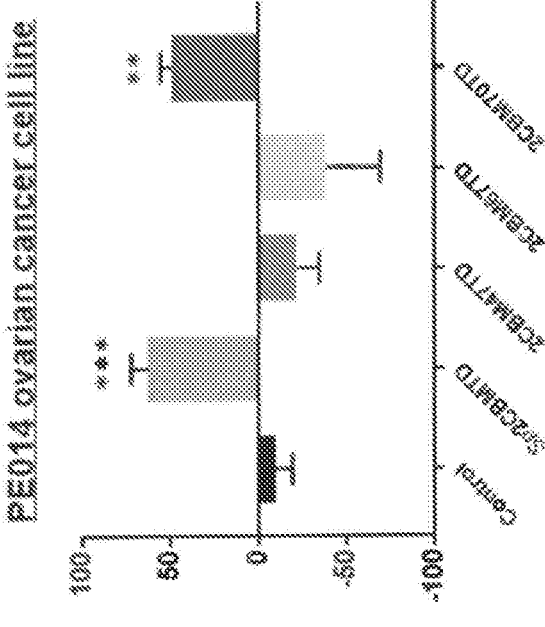

FIG. 5: Proliferation data (BrdU incorporation assay). Different cancer cell lines ((a), Glioma (T98G), Colon ((b), SW620) and Ovarian ((c), PE014, (d) PE01)) were treated with 2CBM47TD (400 µg/mL), 2CBM67TD (400 µg/mL), 2CBM70TD (400 µg/mL), PBS (control) or sialic acid binding CBM40 agent Sp2CBMTD (400 µg/mL) and left for 24 hours. The cells were then subject to a BrdU assay and incubated for 2-6 hrs. An ELISA assay was performed to measure the quantity of BrdU incorporated into the DNA. This assay is a standard assay to measure cell growth/proliferation. A two-way ANOVA was used to show statistical significance vs the control group (p of <0.0001 represented by **, p of <0.001 represented by *, p of <0.01 represented by ** and p of <0.1 represented by *).

Figure 6:
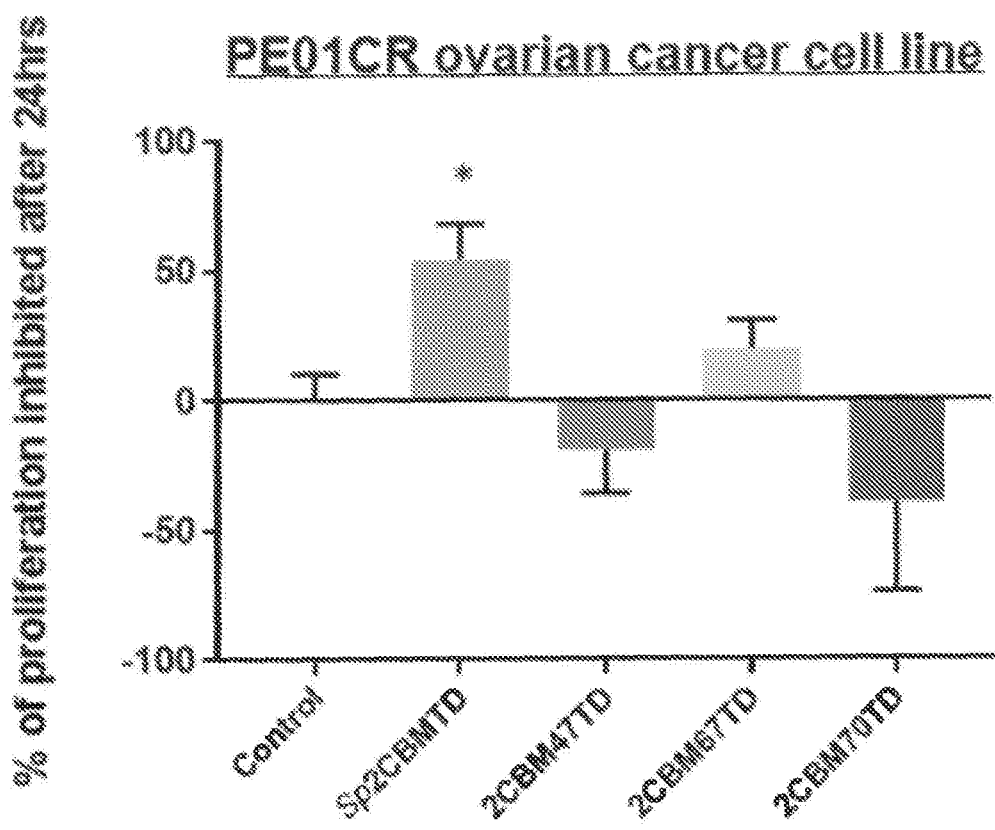

FIG. 6: Proliferation data (BrdU incorporation assay). Ovarian cancer cell (PE01 cisplatin resistant (CR)) was treated with Sp2CBMTD (400 µg/mL), 2CBM47TD (400 µg/mL), 2CBM67TD (400 µg/mL), 2CBM70TD (400 µg/mL) or PBS (control) and left for 24 hours. The cells were then subject to a BrdU assay and incubated for 2-6 hrs. An ELISA assay was performed to measure the quantity of BrdU incorporated into the DNA. This assay is a standard assay to measure cell growth/proliferation. A two-way ANOVA was used to show statistical significance vs the control group (p of <0.0001 represented by **, p of <0.001 represented by *, p of <0.01 represented by ** and p of <0.1 represented by *).

Figure 7A:
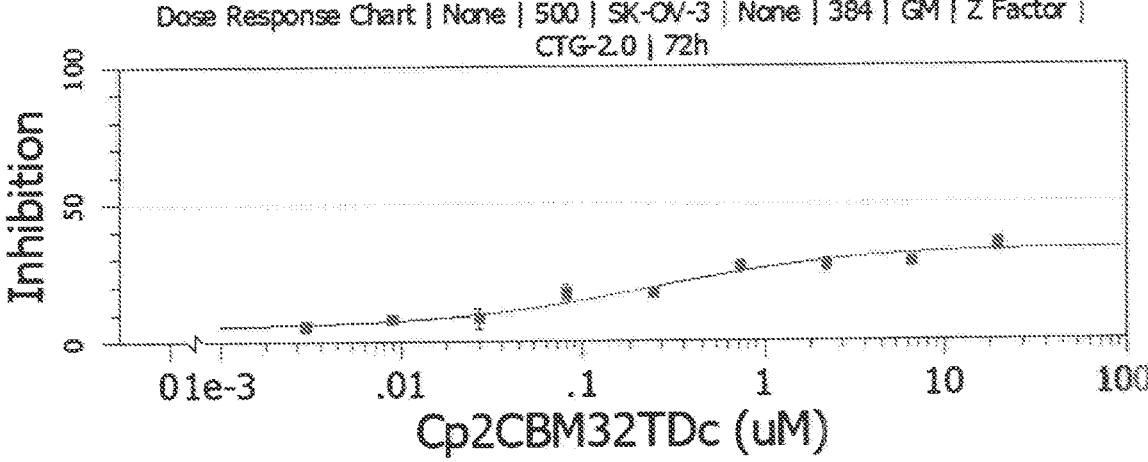
Figure 7B:
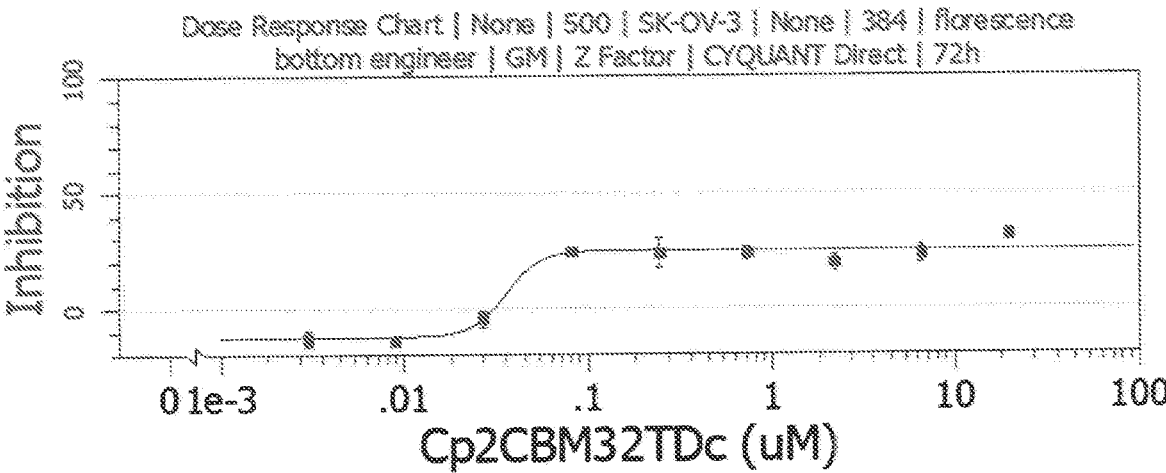

FIG. 7: Proliferation data obtained from (a) CellTiter Glo® 2.0 Assay (CTG2.0); and (b) CyQUANT® Direct Cell Proliferation Assay. Ovarian cancer cell line (SK-OV-3) was treated with Cp2CBM32TD and left for 72 hours as outlined below. A dose response curve was generated with nine different concentrations using a 3-fold dilution series from 3 mg/mL to 0.457 µg/mL. After treatment, the plates were developed for endpoint analysis using either the CellTiter-Glo® 2.0 Assay or the CyQUANT® Direct Cell Proliferation Assay.

Figure 8A:
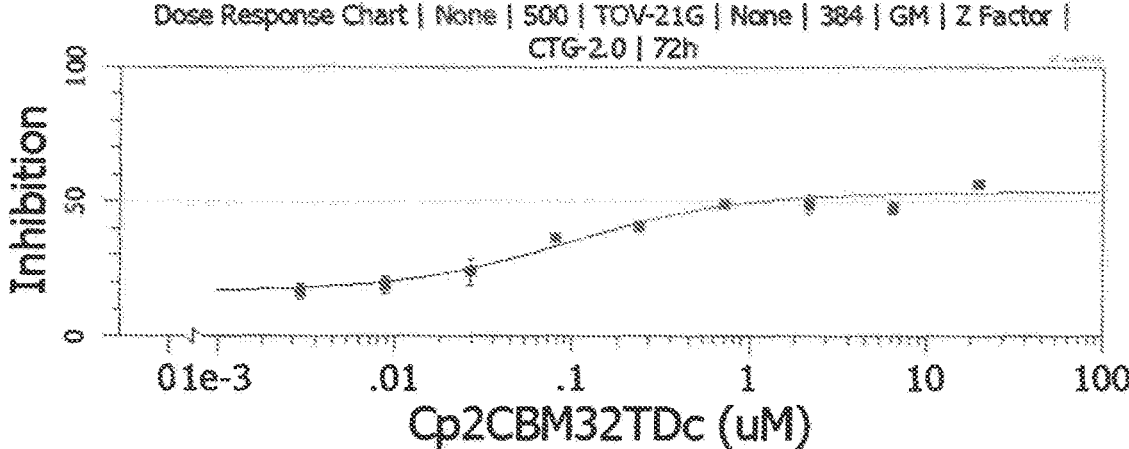
Figure 8B:
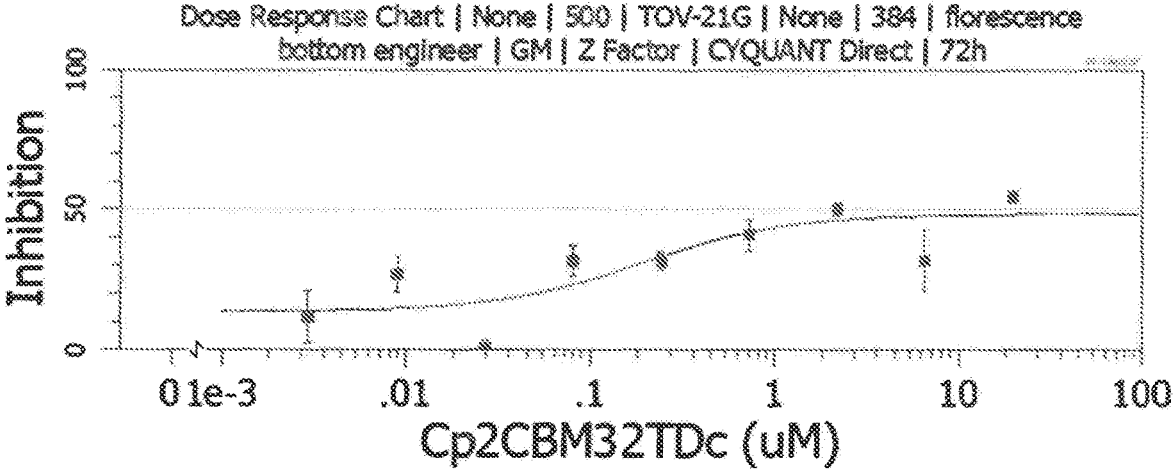

FIG. 8: Proliferation data obtained from (a) CellTiter Glo® 2.0 Assay (CTG2.0); and (b) CyQUANT® Direct Cell Proliferation Assay. Ovarian cancer cell line (TOV-21G) was treated with Cp2CBM32TD and left for 72 hours as outlined below. A dose response curve was generated with nine different concentrations using a 3-fold dilution series from 3 mg/mL to 0.457 µg/mL. After treatment, the plates were developed for endpoint analysis using either the Cell-Titer-Glo® 2.0 Assay or the CyQUANT® Direct Cell Proliferation Assay.

Figure 9A:
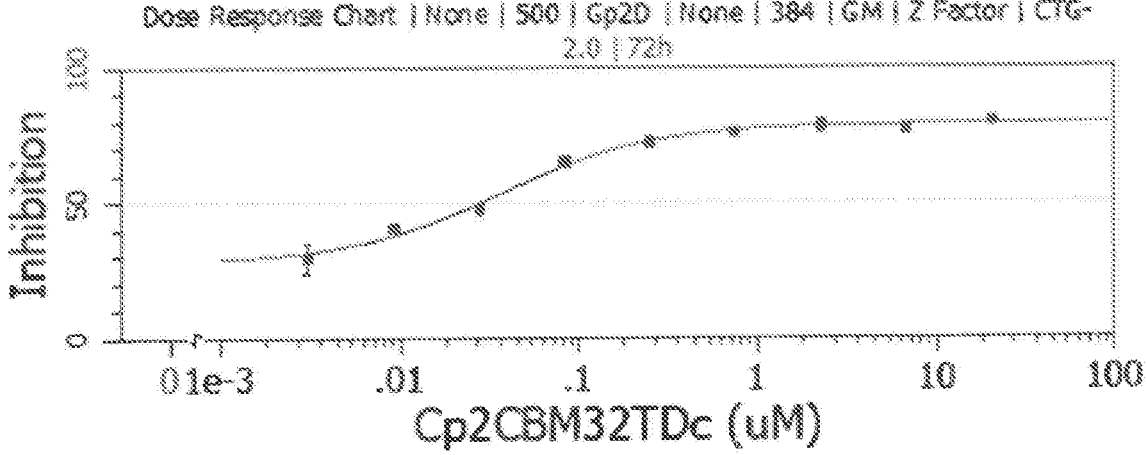
Figure 9B:
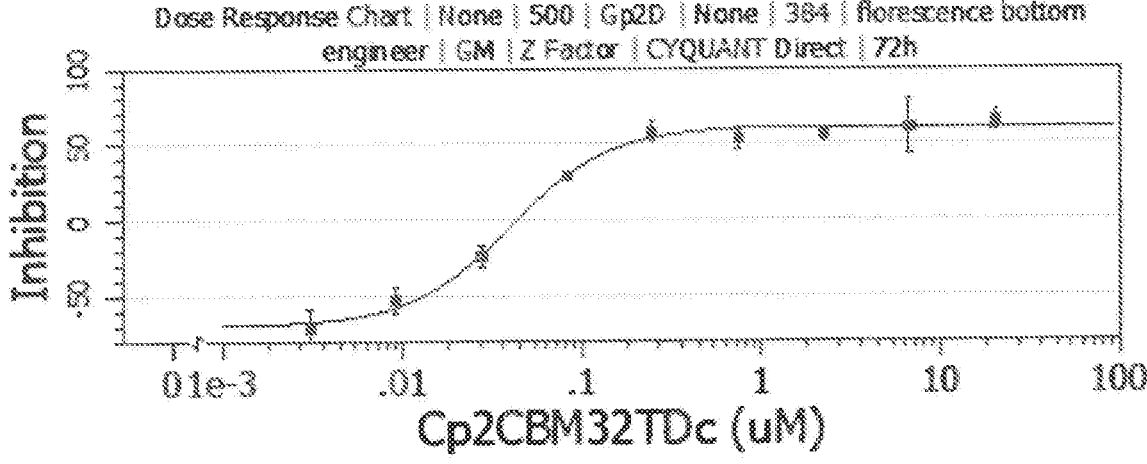

FIG. 9: Proliferation data obtained from (a) CellTiter Glo® 2.0 Assay (CTG2.0); and (b) CyQUANT® Direct Cell Proliferation Assay. Colorectal cancer cell line (Gp2D) was treated with Cp2CBM32TD and left for 72 hours as outlined below. A dose response curve was generated with nine different concentrations using a 3-fold dilution series from 3 mg/mL to 0.457 µg/mL. After treatment, the plates were developed for endpoint analysis using either the CellTiter-Glo® 2.0 Assay or the CyQUANT® Direct Cell Proliferation Assay.

Figure 10A:
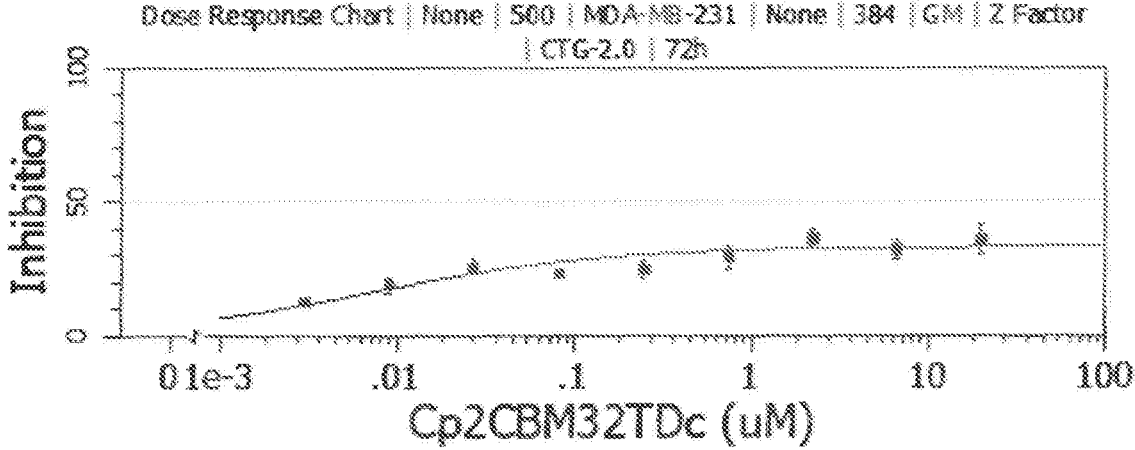
Figure 10B:
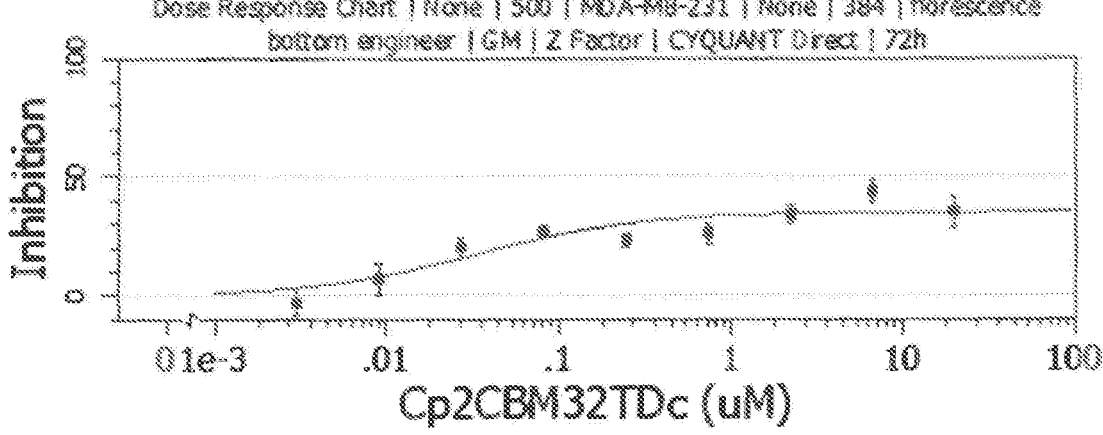

FIG. 10: Proliferation data obtained from (a) CellTiter Glo® 2.0 Assay (CTG2.0); and (b) CyQUANT® Direct Cell Proliferation Assay. Breast cancer cell line (MDA-MB-231) was treated with Cp2CBM32TD and left for 72 hours as outlined below. A dose response curve was generated with nine different concentrations using a 3-fold dilution series from 3 mg/mL to 0.457 µg/mL. After treatment, the plates were developed for endpoint analysis using either the Cell-Titer-Glo® 2.0 Assay or the CyQUANT® Direct Cell Proliferation Assay.

FIG. 11: Proliferation data obtained from (a) CellTiter Glo® 2.0 Assay (CTG2.0); and (b) CyQUANT® Direct Cell Proliferation Assay. Breast cancer cell line (CAMA-1) was treated with Cp2CBM32TD and left for 72 hours as outlined below. A dose response curve was generated with nine different concentrations using a 3-fold dilution series from 3 mg/mL to 0.457 µg/mL. After treatment, the plates were developed for endpoint analysis using either the CellTiter-Glo® 2.0 Assay or the CyQUANT® Direct Cell Proliferation Assay.

Figure 12A:
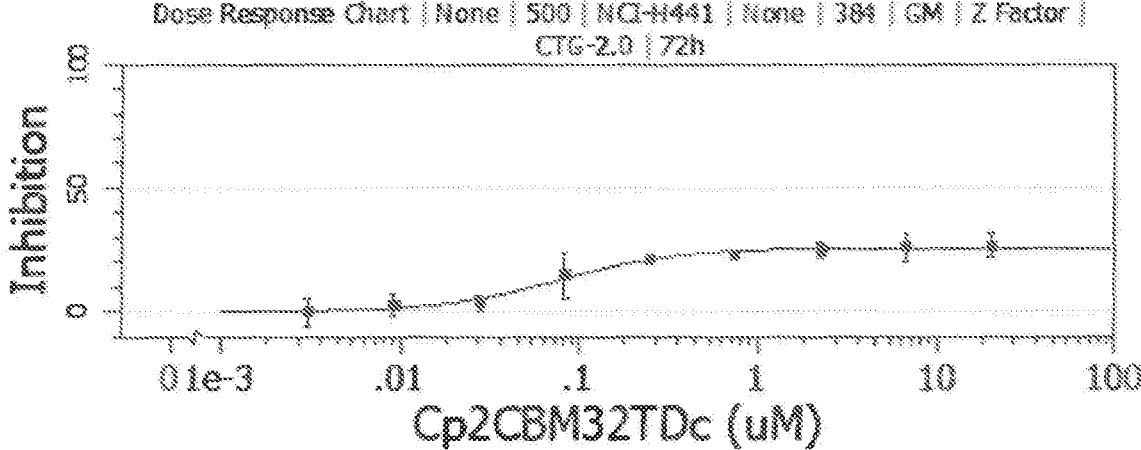
Figure 12B:
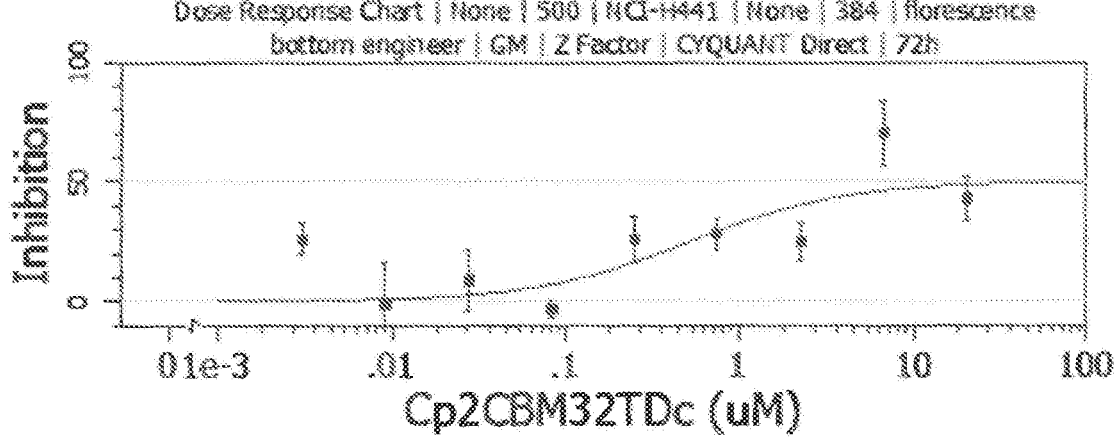

FIG. 12: Proliferation data obtained from (a) CellTiter Glo® 2.0 Assay (CTG2.0); and (b) CyQUANT® Direct Cell Proliferation Assay. Lung cancer cell line (NCI-H441) was treated with Cp2CBM32TD and left for 72 hours as outlined below. A dose response curve was generated with nine different concentrations using a 3-fold dilution series from 3 mg/mL to 0.457 µg/mL. After treatment, the plates were developed for endpoint analysis using either the CellTiter-Glo® 2.0 Assay or the CyQUANT® Direct Cell Proliferation Assay.

EXPERIMENTAL

Part A

A number of different cancer cell lines were treated with various CBM test agents, each comprising one or more molecules comprising a CBM selected from the group consisting of CBM32, CBM40, CBM47, CBM67 and CBM70.

These test agents were assessed in the BrdU cell proliferation assays as outlined above under each of FIGS. 1 to 6.

The results of these assays are shown in FIGS. 1 to 6.

Part B

The CBM Cp2CBM32TD was selected for further investigation using the following assays:

(i) CellTiter Glo® 2.0 Assay (CTG2.0); and (ii) CyQUANT® Direct Cell Proliferation Assay.

The CellTiter-Glo® 2.0 Assay provides a homogeneous method to determine the number of viable cells in culture by quantitating the amount of ATP present, which indicates the presence of metabolically active cells. The CyQUANT® Direct Cell Proliferation Assay relies on the use of a cell-permeant DNA-binding dye in combination with a background suppression reagent. These procedures are fully described in the Promega CellTiter-Glo® 2.0 Assay Technical Manual TM403 (October 2018) and the CyQUANT® Direct Cell Proliferation Assay Molecular Probes manual MP 35011 (20 Jul. 2009).

Cell lines that have been preserved in liquid nitrogen are thawed and expanded in growth media. Once cells have reached expected doubling times, screening begins. 25 µL of cells in growth media are seeded in black 384-well tissue culture treated plates at 500-1500 cells per well. Assay plates were equilibrated via centrifugation and incubated for 24 hours at 37° C. prior to compound treatment. At the time of treatment, a set of timepoint 0 (To) assay plates (which do not receive treatment) are collected and readings for DNA-content and viability measured using CyQUANT® Direct (ThermoFisher) Cell Proliferation Assay and CellTitre-Glo® 2.0 (Promega) metabolic-based assay, respectively. 15 µL/well of assay reagents are added to assay plates. Nine different concentrations were assessed using a 3-fold dilution series from 3 mg/mL to 0.457 µg/mL.

Timepoint 0 (To) plates are either read for fluorescence (CyQUANT®) or absorbance (CellTitre-Glo® 2.0) on Envision plate readers (Perkin Elmer). Assay plates are incubated with compound for 72 hours and are then analysed using CyQUANT® Direct Cell Proliferation Assay and CellTitre-Glo® 2.0 metabolic-based assay.

Growth Inhibition (GI) was used as a measure of cell growth. The GI percentages are calculated by applying the following test and equation:

$$\text{If } T < V_0 : 100 * \left(1 - \frac{T - V_0}{V_0}\right)$$

$$\text{If } T \geq V_0 : 100 * \left(1 - \frac{T - V_0}{V - V_0}\right)$$

where T is the signal measure for a test article, V is the untreated/vehicle-treated control measure, and $V_o$ is the untreated/vehicle control measure at time zero (also colloquially referred as $T_0$ plates). This formula is derived from the Growth Inhibition calculation used in the National Cancer Institute's NCI-60 high throughput screen.

A GI reading of 0% represents no growth inhibition and would occur in instances where the T reading at 72 hours is comparable to the V reading at the respective time period. A GI of 100% represents complete growth inhibition (cytostasis) and in this case cells treated with compound for 72 hours would have the same endpoint reading as $T_0$ control cells. A GI of 200% represents complete death (cytotoxicity) of all cells in the culture well and in this case the T reading at 72 hours will be lower than the $T_0$ control.

Inhibition was also provided as a measure of cell viability. Inhibition levels of 0% represent no inhibition of cell growth by treatment. Inhibition of 100% represents no doubling of cell numbers during the treatment window. Both cytostatic and cytotoxic treatments can yield an Inhibition percentage of 100%. Inhibition percentage is calculated using the following formula:

$$I = 1 - T/U$$

where T is the treated and U is the untreated/vehicle control.

In each case, cells were seeded in growth media in black 384-well tissue culture treated plates and equilibrated via centrifugation. The treated assay plates were incubated with the test compound for 72 hours. After treatment, the plates were developed for endpoint analysis using either the Cell-Titer-Glo® 2.0 Assay or the CyQUANT® Direct Cell Proliferation Assay.

The results are shown in FIGS. 7 to 12.

Figure 11A:
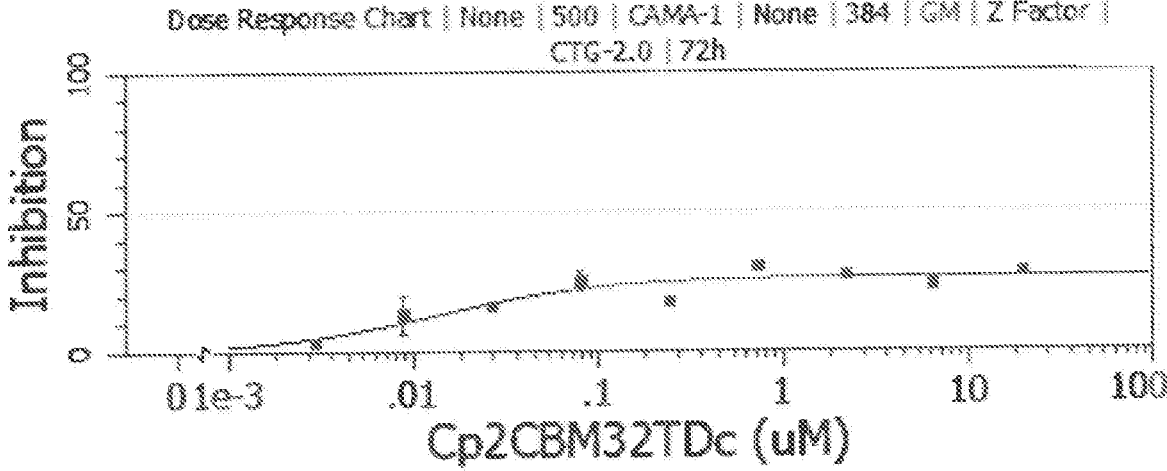
Figure 11B:
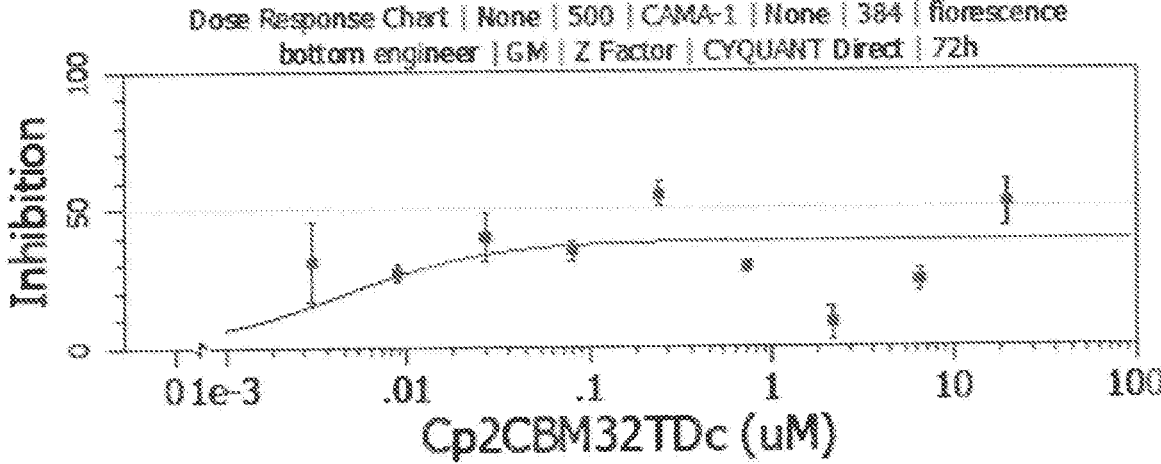

During these further investigations, the inventors identified that Cp2CBM32TD did show anti-proliferative activity against the breast cancer cell line MDA.MB.231 (see FIGS. 10*a* and 10*b*) and also the breast cancer cell line CAMA-1 (see FIGS. 11*a* and 11*b*). This same level of activity against MDA.MB.231 cancer cells was not observed in the BrdU assay.

Without being bound by theory, the inventors hypothesize that this difference may be attributable to the population doubling time of MDA.MB.231 cells (which is approximately 36 hrs). Therefore, it is believed that the shorter treatment period in the BrdU assay (which had a duration of 24 hours) was not sufficient to properly demonstrate the anti-proliferative activity of Cp2CBM32TD against MDA.MB.231 cells.

The invention claimed is:

1. A method for the treatment of cancer, the method comprising administering a carbohydrate binding module to a subject in need thereof, wherein the carbohydrate binding module is a carbohydrate binding module of carbohydrate binding module Family 32 (CBM32).

2. The method of claim 1, wherein the carbohydrate binding module of carbohydrate binding module Family 32 (CBM32) comprises SEQ ID NO: 1 or SEQ ID NO: 2 or a carbohydrate binding portion thereof.

3. The method of claim 1, wherein the cancer is selected from the group consisting of:
   (a) ovarian cancer;
   (b) lung cancer;
   (c) colon cancer; and
   (d) breast cancer.

4. The method according to claim 1, wherein the carbohydrate binding module comprises a single CpCBM32, or two or more CBMs selected from the group consisting of:
   (i) a CBM32; and
   (ii) a CpCBM32.

5. The method according to claim 1, wherein the carbohydrate binding module comprises Cp2CBM32TD.

6. The method of claim 1, wherein the carbohydrate binding module is selected from the group consisting of:
   (i) a molecule comprising two or more CBM32 (s);
   (ii) a molecule comprising one, two or more CpCBM32 (s);
   (iii) a molecule comprising one, two or more peptide(s) or protein(s) comprising a sequence of SEQ ID NO: 1, 2, or a carbohydrate binding portion thereof, and
   (iv) a molecule comprising Cp2CBM32TD.

7. The method of claim 6, wherein the cancer is selected from the group consisting of:
   (a) ovarian cancer;
   (b) lung cancer;
   (c) colon cancer; and
   (d) breast cancer.

8. A method of treating a refractory cancer, the method comprising administering to a subject in need thereof a carbohydrate binding module classified as a CBM32 or a molecule comprising a carbohydrate binding module classified as a CBM32.

9. The method according to claim 8, wherein the refractory cancer is refractory ovarian cancer.

* * * * *